(12) United States Patent
Lui et al.

(10) Patent No.: US 11,800,794 B2
(45) Date of Patent: Oct. 24, 2023

(54) COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

(71) Applicant: SAMSUNG SDI CO., LTD., Yongin-si (KR)

(72) Inventors: Jihyun Lui, Suwon-si (KR); Changwoo Kim, Suwon-si (KR); Dong Wan Ryu, Suwon-si (KR); Chang Ju Shin, Suwon-si (KR); Hyung Sun Kim, Suwon-si (KR); Seungjae Lee, Suwon-si (KR); Jihun Shin, Suwon-si (KR); Sung-Hyun Jung, Suwon-si (KR); Ho Kuk Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 0 days.

(21) Appl. No.: 16/930,406

(22) Filed: Jul. 16, 2020

(65) Prior Publication Data
US 2020/0350501 A1 Nov. 5, 2020

Related U.S. Application Data

(60) Division of application No. 16/285,711, filed on Feb. 26, 2019, now abandoned, which is a continuation of application No. 16/269,700, filed on Feb. 7, 2019, now Pat. No. 11,217,756, and a continuation-in-part of application No. PCT/KR2018/006794, filed on Jun. 15, 2018.

(30) Foreign Application Priority Data

Jun. 22, 2017 (KR) .................. 10-2017-0079209
May 4, 2018 (KR) .................. 10-2018-0052121
Jun. 19, 2018 (KR) .................. 10-2018-0070145

(51) Int. Cl.
| | | |
|---|---|---|
| H10K 85/60 | (2023.01) | |
| C07D 405/14 | (2006.01) | |
| H10K 50/11 | (2023.01) | |
| H10K 85/30 | (2023.01) | |
| H10K 101/10 | (2023.01) | |
| H10K 101/00 | (2023.01) | |

(52) U.S. Cl.
CPC ......... *H10K 85/654* (2023.02); *C07D 405/14* (2013.01); *H10K 85/6572* (2023.02); *H10K 85/6574* (2023.02); *H10K 50/11* (2023.02); *H10K 85/342* (2023.02); *H10K 2101/10* (2023.02); *H10K 2101/90* (2023.02)

(58) Field of Classification Search
CPC ............. H01L 51/0067; H01L 51/0072; H01L 51/0073; H01L 51/0074; H01L 51/5012; H01L 51/5056; H01L 51/5072; H01L 51/5088; C07D 405/14; C07D 409/14; H10K 50/11; H10K 50/15; H10K 50/16; H10K 50/17; H10K 85/654; H10K 85/6572; H10K 85/6574; H10K 85/6576
USPC ................... 428/690, 691, 917; 427/58, 66; 313/500–512; 257/40, 88–104, 257/E51.001–E51.052; 252/301.16–301.35
See application file for complete search history.

(56) References Cited

U.S. PATENT DOCUMENTS

| | | |
|---|---|---|
| 5,061,569 A | 10/1991 | VanSlyke et al. |
| 8,946,697 B1 | 2/2015 | Ma et al. |
| 9,397,307 B2 | 7/2016 | Nishimura |

(Continued)

FOREIGN PATENT DOCUMENTS

| | | |
|---|---|---|
| CN | 103435597 A | 12/2013 |
| CN | 106029831 A | 10/2016 |

(Continued)

OTHER PUBLICATIONS

Jung et al., machine translation of WO 2018/016724 (2018) pp. 1-21. (Year: 2018).*

(Continued)

*Primary Examiner* — Dylan C Kershner
(74) *Attorney, Agent, or Firm* — Lee IP Law, P.C.

(57) ABSTRACT

Disclosed are the compound for an organic optoelectronic device, the compound being represented by Chemical Formula 1, a composition for an organic optoelectronic device including the compound for an organic optoelectronic device, an organic optoelectronic device, and a display device.

[Chemical Formula 1]

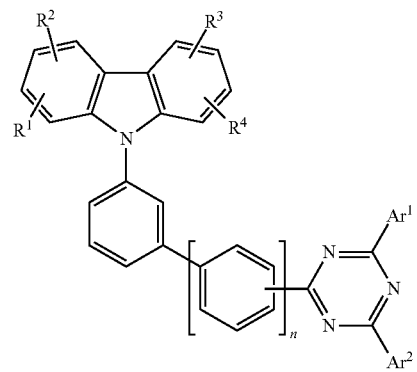

In Chemical Formula 1, each substituent is the same as defined in the specification.

11 Claims, 1 Drawing Sheet

(56) References Cited

U.S. PATENT DOCUMENTS

| | | |
|---|---|---|
| 9,847,501 B2 | 12/2017 | Mizutani |
| 10,985,329 B2 | 4/2021 | Lee |
| 11,217,756 B2 | 1/2022 | Lui |
| 11,223,019 B2 | 1/2022 | Lui |
| 2002/0121860 A1 | 9/2002 | Seo ............... H01L 51/0096 313/506 |
| 2002/0182441 A1 | 12/2002 | Lamansky et al. |
| 2006/0022590 A1 | 2/2006 | Aziz et al. |
| 2006/0078757 A1 | 4/2006 | Boerner |
| 2006/0088728 A1 | 4/2006 | Kwong et al. |
| 2007/0252516 A1 | 11/2007 | Kondakova et al. |
| 2012/0273764 A1 | 11/2012 | Yu et al. |
| 2014/0131676 A1 | 5/2014 | Beers |
| 2014/0231769 A1 | 8/2014 | Nishimura |
| 2014/0312338 A1 | 10/2014 | Mizutani ............ C07D 491/048 257/40 |
| 2015/0171340 A1 | 6/2015 | Lee et al. |
| 2015/0207079 A1 | 7/2015 | Cho et al. |
| 2016/0049597 A1 | 2/2016 | Ma |
| 2016/0088728 A1 | 3/2016 | Wang et al. |
| 2016/0093808 A1 | 3/2016 | Adamovich et al. |
| 2016/0141521 A1 | 5/2016 | Watanabe et al. |
| 2017/0047527 A1 | 2/2017 | Lee et al. |
| 2017/0069848 A1 | 3/2017 | Zeng |
| 2017/0170408 A1 | 6/2017 | Park et al. |
| 2017/0213968 A1 | 7/2017 | Park ..................... H05B 33/20 |
| 2017/0317293 A1 | 11/2017 | Kim et al. |
| 2019/0198771 A1 | 6/2019 | Lui et al. |
| 2019/0198772 A1 | 6/2019 | Lui |
| 2019/0363261 A1* | 11/2019 | Lee .................... H01L 51/0072 |
| 2020/0127213 A1 | 4/2020 | Jang |
| 2020/0161560 A1 | 5/2020 | Jang |
| 2020/0161563 A1* | 5/2020 | Jang .................... H01L 51/0073 |
| 2020/0350501 A1 | 11/2020 | Lui |
| 2021/0135118 A1* | 5/2021 | Son ..................... C07D 405/14 |
| 2022/0140251 A1 | 5/2022 | Lui |

FOREIGN PATENT DOCUMENTS

| | | |
|---|---|---|
| CN | 106575663 A | 4/2017 |
| CN | 107337650 A | 11/2017 |
| JP | 05-09471 A | 1/1993 |
| JP | 05-25473 A | 2/1993 |
| JP | 07126615 A | 5/1995 |
| JP | 1095973 A | 4/1998 |
| JP | 2003-133075 A | 5/2003 |
| JP | 5206907 B2 | 6/2013 |
| JP | 5338184 B2 | 11/2013 |
| JP | 5707665 B2 | 4/2015 |
| JP | 2017-503338 A | 1/2017 |
| JP | 2017-513220 A | 5/2017 |
| JP | 2017/175099 A | 9/2017 |
| KR | 10-2013-0074765 | 7/2013 |
| KR | 10-2013-0131230 | 12/2013 |
| KR | 10-2014-0046541 | 4/2014 |
| KR | 20140083897 A * | 7/2014 |
| KR | 10-2014-0144550 | 12/2014 |
| KR | 10-2015-0042335 | 4/2015 |
| KR | 10-2015-0070860 | 6/2015 |
| KR | 10-2016-0010333 | 1/2016 |
| KR | 10-2016-0010373 | 1/2016 |
| KR | 10-2016-0011036 | 1/2016 |
| KR | 10-2016-0060539 | 5/2016 |
| KR | 10-2016-0064955 | 6/2016 |
| KR | 10-2016-0069934 | 6/2016 |
| KR | 10-2017-0037276 | 4/2017 |
| KR | 10-1744248 | 5/2017 |
| KR | 10-2017-0113318 | 10/2017 |
| KR | 10-2018-0007617 | 1/2018 |
| KR | 10-2018-0010808 | 1/2018 |
| KR | 10-2018-0013449 | 2/2018 |
| KR | 10-2018-0069475 | 6/2018 |
| KR | 10-2019-0045436 A | 5/2019 |
| KR | 10-2019-0058748 A | 5/2019 |
| WO | WO 9509147 A1 | 4/1995 |
| WO | WO 2004/055921 A2 | 7/2004 |
| WO | WO 2012/070233 A1 | 5/2012 |
| WO | WO 2012/108881 A1 | 8/2012 |
| WO | WO 2013/077352 A1 | 5/2013 |
| WO | WO 2013/077362 A1 | 5/2013 |
| WO | WO 2014/054912 A1 | 4/2014 |
| WO | WO 2016-013867 A1 | 1/2016 |
| WO | WO/2016010402 A1 | 1/2016 |
| WO | WO 2016-080791 A1 | 5/2016 |
| WO | WO 2016-208873 A1 | 12/2016 |
| WO | WO 2018/016724 A1 | 1/2018 |
| WO | WO 2018/038400 A1 | 3/2018 |
| WO | WO 2018/048074 A1 | 3/2018 |
| WO | WO 2018/110958 A1 | 6/2018 |
| WO | WO-2018194278 A2 * | 10/2018 ............. C09K 11/06 |
| WO | WO-2018236093 A1 * | 12/2018 ........... C07D 405/14 |
| WO | WO-2019083215 A1 * | 5/2019 ............. H01L 51/00 |
| WO | WO 2020157204 A1 | 8/2020 |
| WO | WO-2020157204 A1 | 8/2020 ......... H01L 51/0072 |

OTHER PUBLICATIONS

Son et al., machine translation of WO 2019/083215 (2019) pp. 1-230. (Year: 2019).*
Lee et al., machine translation of KR-20140083897-A (2014) pp. 1-49. (Year: 2014).*
Bum S H et al., machine translation of WO-2018194278-A2 (2018) pp. 1-14. (Year: 2018).*
Jang K et al., machine translation of WO-2018236093-A1 (2018) pp. 1-23. (Year: 2018).*
European Office action dated Nov. 13, 2020.
Japanese Office action dated Dec. 15, 2020.
Gong et al. "Tuning the Photophysical Properties and Energy Levels by Linking Spacer and Topology, etc . . . ", J. Phys. Chem. C. 2010/114, 5193-5198, Mar. 1, 2010.
Kim, et al., Machine Translation of WO 2018/110958 A1 (2018), pp. 1-53.
Tominaga, et al. Machine Translation of JP 2003-133075 A (2003) pp. 109.
Zheng, Caijun, et al., Machine Translation of CN 103435597 A (2013), pp. 1-13.
Office Action dated Dec. 20, 2019 in U.S. Appl. No. 16/269,700.
Office Action dated Jan. 13, 2020 in U.S. Appl. No. 16/285,617.
USPTO Advisory action dated Mar. 30, 2020 for U.S. Appl. No. 16/269,700.
Chinese Office action dated Mar. 24, 2020.
U.S. Office action received in co pending related U.S. Appl. No. 16/285,617.
U.S. Office action received in co pending related U.S. Appl. No. 16/269,700 dated Apr. 22, 2021.
U.S. Office action received in co pending related U.S. Appl. No. 16/285,711 dated Mar. 4, 2021.
Office action received in co pending U.S. Appl. No. 16/285,617 dated Nov. 13, 2020.
Office action received in co pending U.S. Appl. No. 16/269,700 dated Oct. 29, 2020.
U.S. Appl. No. 16/285,617, filed Feb. 26, 2019.
U.S. Office action received in copending U.S. Appl. No. 16/285,711 dated Sep. 20, 2021.
U.S. Office action received in co pending U.S. Appl. No. 16/619,677 dated Jun. 8, 2022.
U.S. Office action received in U.S. Appl. No. 16/619,677, dated Dec. 1, 2022.
Chinese Search Report dated Sep. 9, 2022.
CAS reg. No. 2259709-50-5, Jan. 17, 2019.
U.S. Office action received in co pending related U.S. Appl. No. 16/722,853, dated Sep. 9, 2022.
U.S. Office received in copending related U.S. Appl. No. 17/569,012, dated Mar. 31, 2023.
U.S. Notice of Allowance received in copending related U.S. Appl. No. 16/722,853, dated Feb. 22, 2023.

* cited by examiner

[FIG. 1]
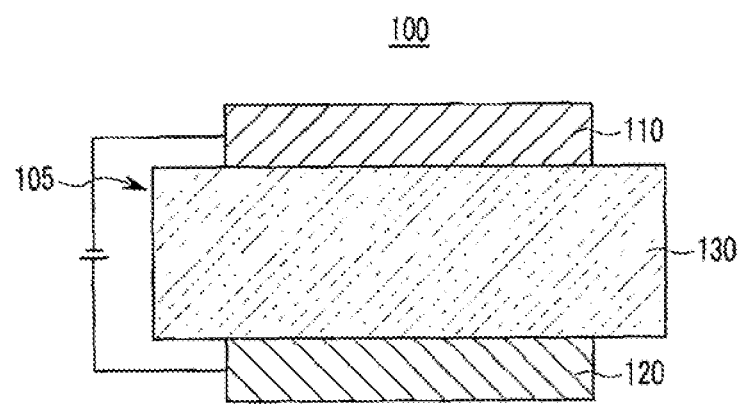
[FIG. 2]
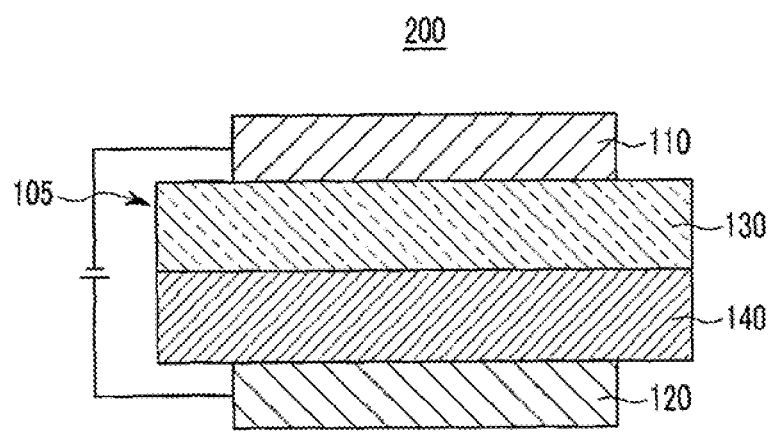

COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

CROSS-REFERENCE TO RELATED APPLICATIONS

This application is a division of pending application Ser. No. 16/285,711, filed Feb. 26, 2019, which in turn is a continuation-in-part of International Application No. PCT/KR2018/006794, filed on Jun. 15, 2018, and claims priority to Korean Patent Application No. 10-2017-0079209 filed on Jun. 22, 2017. Ser. No. 16/285,711 is also a continuation of U.S. application Ser. No. 16/269,700, which was filed on Feb. 7, 2019, and also claims priority to and the benefit of Korean Patent Application Nos. 10-2018-0052121 and 10-2018-0070145 filed in the Korean Intellectual Property Office on May 4, 2018, and Jun. 19, 2018, respectively. The entire contents of all above-referenced applications are incorporated herein by reference.

BACKGROUND OF THE INVENTION

(a) Field of the Invention

Embodiments relate to a compound for an organic optoelectronic device, a composition for an organic optoelectronic device, an organic optoelectronic device, and a display device.

(b) Description of the Related Art

An organic optoelectronic device may be used to convert electrical energy into photo energy or vice versa.

An organic optoelectronic device may be classified as follows in accordance with its driving principles. One is a photoelectric device where excitons are generated by photoenergy, separated into electrons and holes, and are transferred to different electrodes to generate electrical energy. Another is a light emitting device where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

SUMMARY OF THE INVENTION

Embodiments are directed to a compound for an organic optoelectronic device, the compound being represented by Chemical Formula 1:

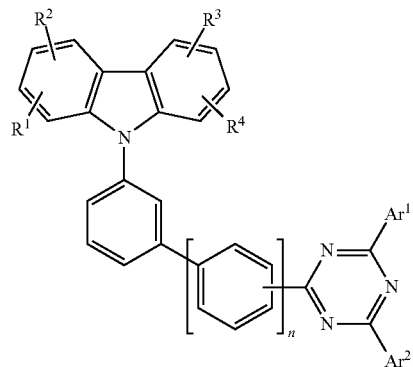

[Chemical Formula 1]

In Chemical Formula 1,
$R^1$ to $R^4$ may each independently be hydrogen, deuterium, a substituted or unsubstituted C1 to C6 alkyl group, or a substituted or unsubstituted phenyl group,
n may be 0, 1, or 2,
$Ar^1$ and $Ar^2$ may each independently be a substituted or unsubstituted C6 to C30 aryl group or a group represented by Chemical Formula A.
At least one of $Ar^1$ and $Ar^2$ is a group represented by Chemical Formula A.

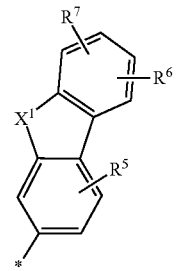

[Chemical Formula A]

In Chemical Formula A,
$X^1$ may be O or S,
$R^5$ to $R^7$ may each independently be hydrogen, deuterium, a substituted or unsubstituted C1 to C6 alkyl group, or a substituted or unsubstituted phenyl group, and
* is a linking point.

Embodiments are also directed to a composition for an organic optoelectronic device, including a first compound for an organic optoelectronic device according to an embodiment, and a second compound for an organic optoelectronic device represented by Chemical Formula 2; or a combination of Chemical Formula 3 and Chemical Formula 4:

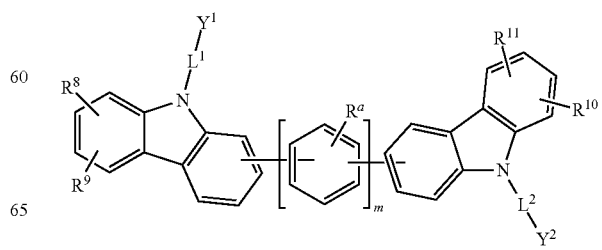

[Chemical Formula 2]

In Chemical Formula 2, $Y^1$ and $Y^2$ may each independently be a substituted or unsubstituted C6 to C20 aryl group, or a substituted or unsubstituted C2 to C30 heterocyclic group, $L^1$ and $L^2$ may each independently be a single bond, or a substituted or unsubstituted C6 to C20 arylene group, $R^a$ and $R^8$ to $R^{11}$ may each independently be hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group, and m may be 0, 1, or 2;

[Chemical Formula 3]

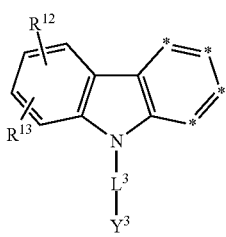

[Chemical Formula 4]

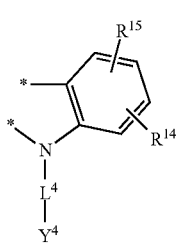

In Chemical Formulae 3 and 4, $Y^3$ and $Y^4$ may each independently be a substituted or unsubstituted C6 to C20 aryl group, or a substituted or unsubstituted C2 to C30 heterocyclic group, adjacent two *'s of Chemical Formula 3 are bonded with Chemical Formula 4, other adjacent two *'s of Chemical Formula 3 not being bonded with Chemical Formula 4* are each independently C-$L^a$-$R^b$, $L^a$, $L^3$, and $L^4$ may each independently be a single bond, or a substituted or unsubstituted C6 to C20 arylene group, and $R^b$ and $R^{12}$ to $R^5$ may each independently be hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group.

Embodiments are also directed to an organic optoelectronic device, including an anode and a cathode facing each other, and at least one organic layer disposed between the anode and the cathode. The organic layer may include a compound for an organic optoelectronic device according to an embodiment or a composition for an organic optoelectronic device according to an embodiment.

Embodiments are also directed to a display device, including an organic optoelectronic device according to an embodiment.

BRIEF DESCRIPTION OF THE DRAWINGS

Features will become apparent to those of skill in the art by describing in detail example embodiments with reference to the attached drawing in which:

FIGS. 1 and 2 are cross-sectional views showing organic light emitting diodes according to embodiments.

DETAILED DESCRIPTION OF THE EMBODIMENTS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

As used herein, when a definition is not otherwise provided, the "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, C1 to C20 alkoxy group, a C1 to C10 trifluoroalkyl group, a cyano group, or a combination thereof.

In one example of the present disclosure, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples of the present disclosure, the "substituted" refers to replacement of at least one hydrogen of a substituent or a compound by deuterium, a C1 to C20 alkyl group, a C6 to C30 aryl group, or a cyano group. In addition, in specific examples of the present disclosure, the "substituted" refers to replacement of at least one hydrogen of a substituent or a compound by deuterium, a C1 to C5 alkyl group, a C6 to C18 aryl group, or a cyano group. In addition, in specific examples of the present disclosure, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, the "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quaterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

As used herein, the "heterocyclic group" is a generic concept of a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to an aryl group including at least one hetero atom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include 1 to 3 hetero atoms.

For example, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or combination thereof, but are not limited thereto.

For example, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or combination thereof, but are not limited thereto.

In the present specification, hole characteristics refer to an ability to donate an electron to form a hole when an electric field is applied, and that a hole formed in the anode may be easily injected into a light emitting layer, and a hole formed in a light emitting layer may be easily transported into an anode and transported in the light emitting layer due to conductive characteristics according to a highest occupied molecular orbital (HOMO) level.

In addition, electron characteristics refer to an ability to accept an electron when an electric field is applied, and that an electron formed in a cathode may be easily injected into a light emitting layer, and an electron formed in a light emitting layer may be easily transported into a cathode and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment may be represented by Chemical Formula 1:

[Chemical Formula 1]

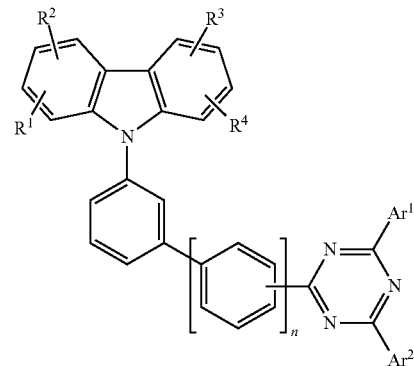

In Chemical Formula 1,
R$^1$ to R$^4$ may each independently be hydrogen, deuterium, a substituted or unsubstituted C1 to C6 alkyl group, or a substituted or unsubstituted phenyl group,
n may be 0, 1, or 2,
Ar$^1$ and Ar$^2$ may each independently be a substituted or unsubstituted C6 to C30 aryl group or a group represented by Chemical Formula A. In an implementation, at least one of Ar$^1$ and Ar$^2$ may be a group represented by Chemical Formula A.

[Chemical Formula A]

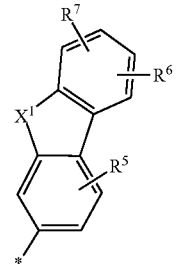

In Chemical Formula A,
X$^1$ may be O or S,
R$^5$ to R$^7$ may each independently be hydrogen, deuterium, a substituted or unsubstituted C1 to C6 alkyl group, or a substituted or unsubstituted phenyl group, and
* is a linking point.

The compound for an organic optoelectronic device represented by Chemical Formula 1 may have an asymmetric molecular structure. The compound for an organic optoelectronic device represented by Chemical Formula 1 may have a structure directly linking at least one 3-dibenzofuranyl group or 3-dibenzothiophenyl group with triazine without a linking group and by directly or indirectly linking a 9-carbazole group to triazine through m-phenylene.

Without being bound by theory, it is believed that, as a 7-bond through C—N bond is broken by substituting carbazole in a N-direction which is a No. 9 position, the electron cloud between HOMO-LUMO is localized, and a meta-phenylene linker is included between triazine and the carbazole group, so the hole transport moiety and the electron transport moiety may be more effectively separated to maximize the life-span improvement effect. In addition, a relatively deep LUMO energy level may be provided by directly linking 3-dibenzofuranyl group or 3-dibenzothiophenyl group with triazine without a linking group, which may be favorable to inject and transport electrons. Thus, as it is favorable to inject and transport hole/electron and effectively localize an electron cloud in a device including the compound for an organic optoelectronic device represented by Chemical Formula 1, it may provide a structure stable for both electron and hole enough to have characteristics more favorable to life-span. For example, it may provide fast electron injection and mobility by including triazine as a center core, so as to provide a carbazole moiety with a strong hole mobility and the charge balance, which may also help long life-span characteristics.

In an example embodiment, n may be an integer of 0 or 1, and for example, Chemical Formula 1 may be represented by Chemical Formula 1-1 or Chemical Formula 1-2.

In Chemical Formula 1-1 and Chemical Formula 1-2, definitions of $R^1$ to $R^4$, $Ar^1$ and $Ar^2$ are the same as described above.

One of $Ar^1$ and $Ar^2$ may be the group represented by Chemical Formula A.

In an example embodiment, one of $Ar^1$ or $Ar^2$ may each independently be a substituted or unsubstituted phenyl group, a substituted or unsubstituted biphenyl group, a substituted or unsubstituted terphenyl group, a substituted or unsubstituted naphthyl group, or the group represented by Chemical Formula A, and the other of $Ar^1$ and $Ar^2$ may be the group represented by Chemical Formula A.

For example, $Ar^1$ and $Ar^2$ may each independently be a substituted or unsubstituted phenyl group, a substituted or unsubstituted biphenyl group, a substituted or unsubstituted terphenyl group, a substituted or unsubstituted naphthyl group, or the group represented by Chemical Formula A, and one of $Ar^1$ and $Ar^2$ may be the group represented by Chemical Formula A.

For example, $Ar^1$ and $Ar^2$ may each independently be one of groups of Group I, and at least one of $Ar^1$ and $Ar^2$ may be the group represented by Chemical Formula A.

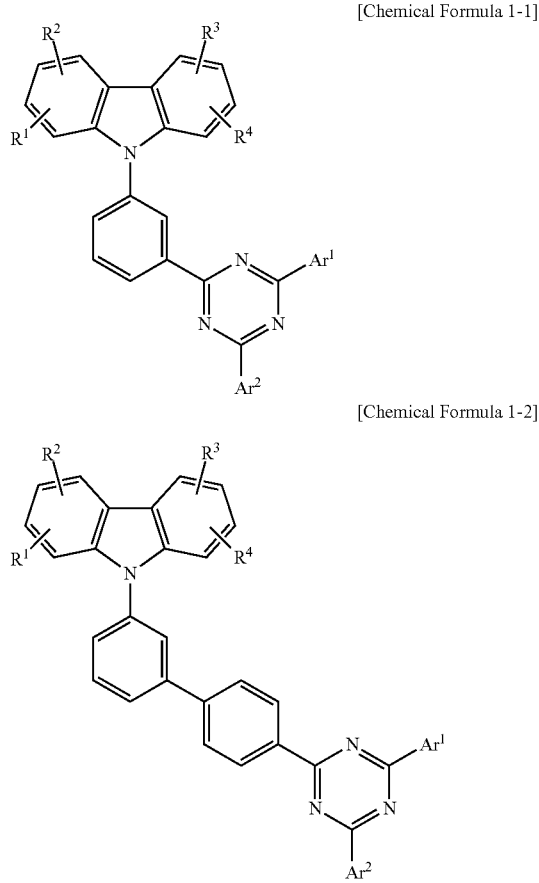

[Chemical Formula 1-1]

[Chemical Formula 1-2]

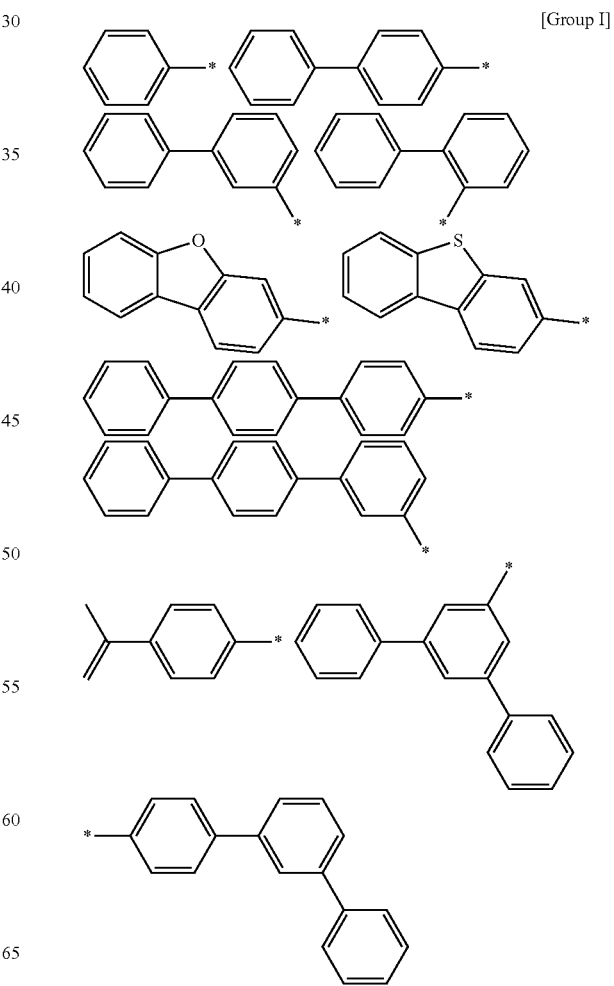

[Group I]

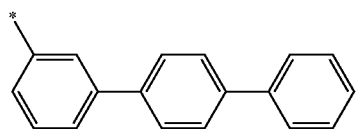

In Group I, * is a linking point.

For example, $R^1$ to $R^4$ may each independently be hydrogen, a phenyl group, or a biphenyl group.

In an example embodiment, $R^1$ to $R^4$ may each independently be hydrogen or at least one of $R^1$ to $R^4$ may be a phenyl group or a biphenyl group.

For example, $R^1$ to $R^4$ may each independently be hydrogen or one of $R^1$ to $R^4$ may be a phenyl group.

For example, the first compound for an organic optoelectronic device may be one of compounds of Group 1.

[Group 1]

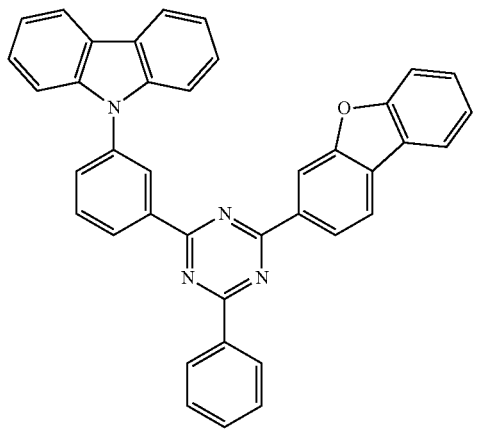
[A-1]

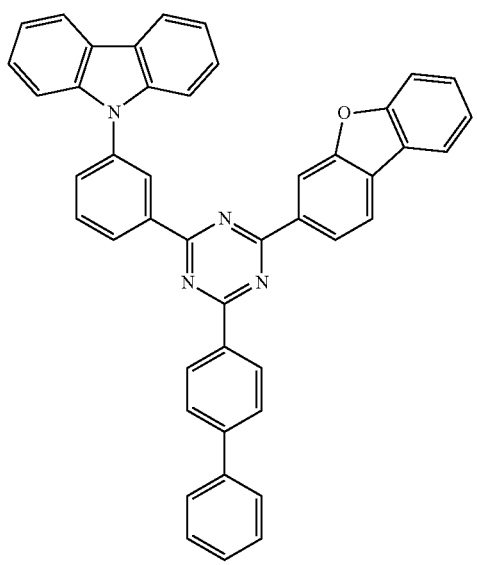
[A-2]

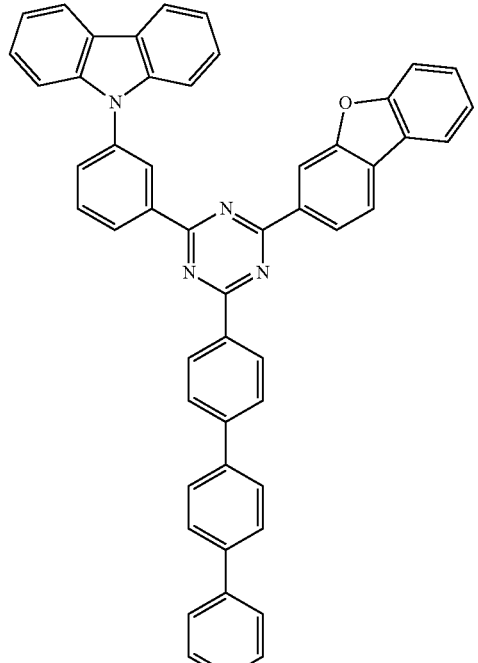
[A-3]

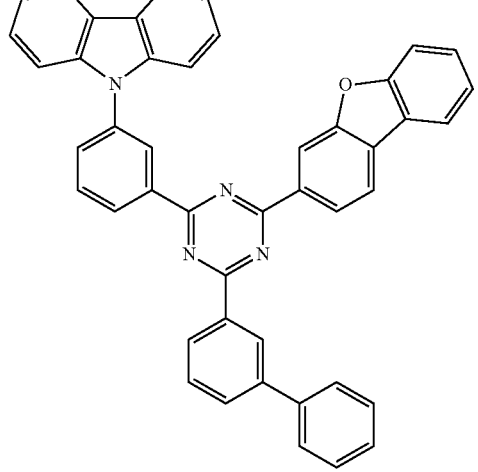
[A-4]

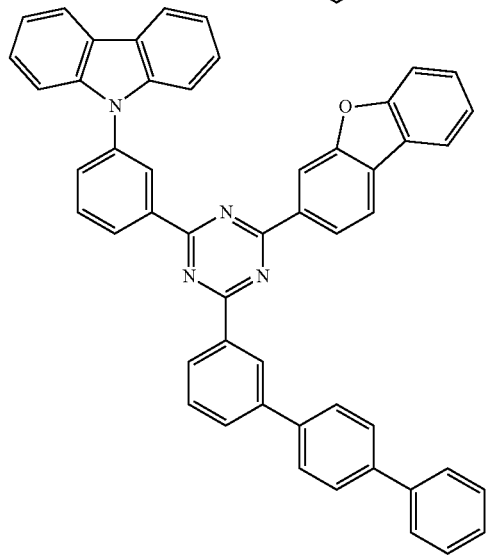
[A-5]

[A-6]
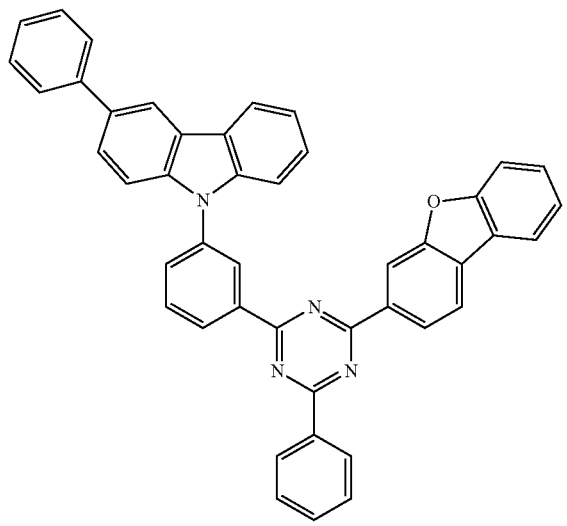
[A-7]
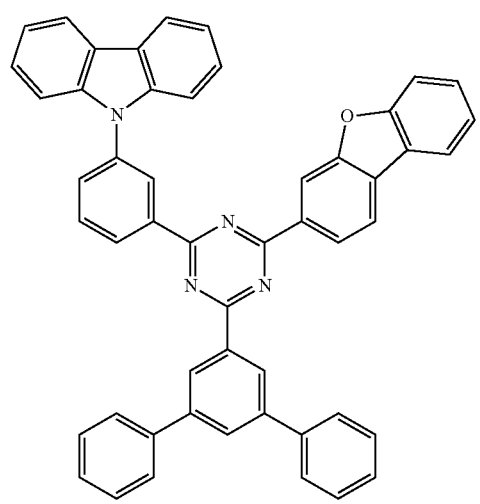
[A-8]
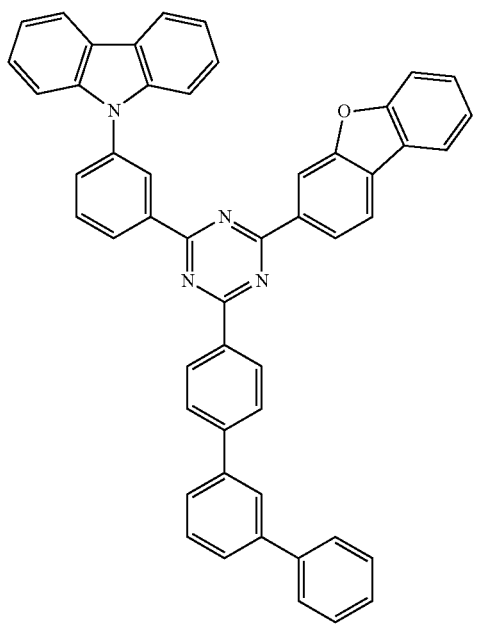
[A-9]
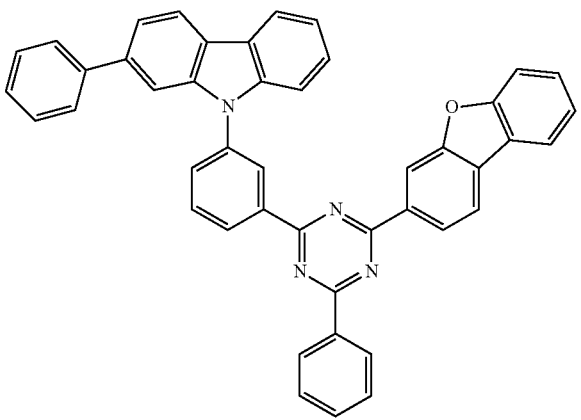
[A-10]
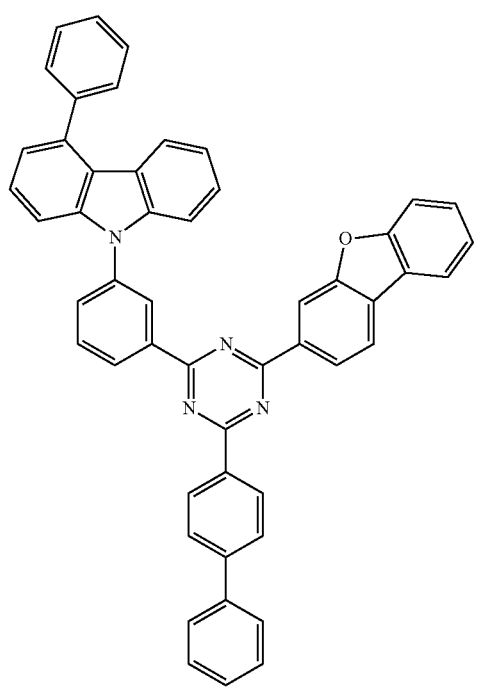
[A-11]
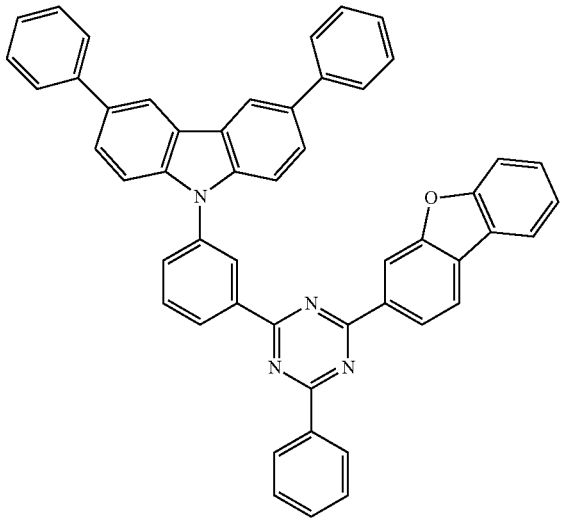

[A-12]
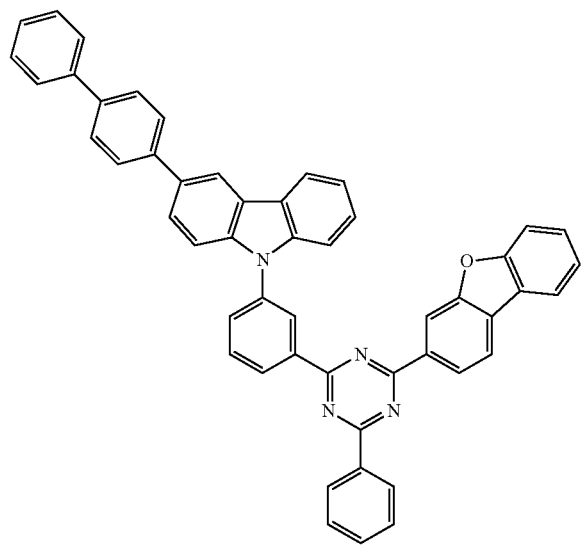
[A-15]
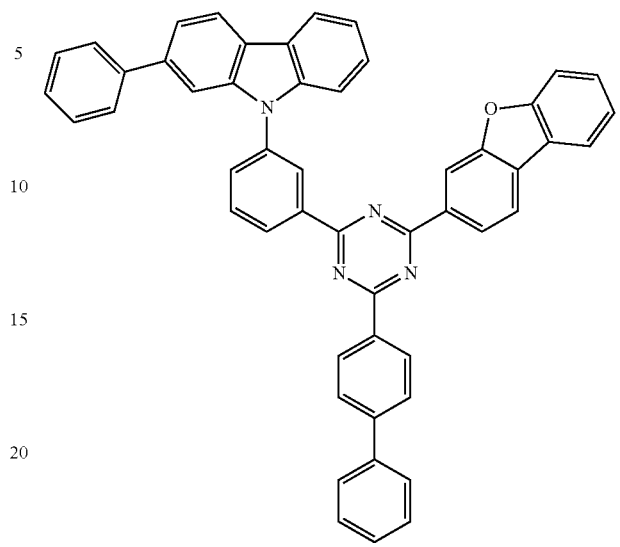
[A-13]
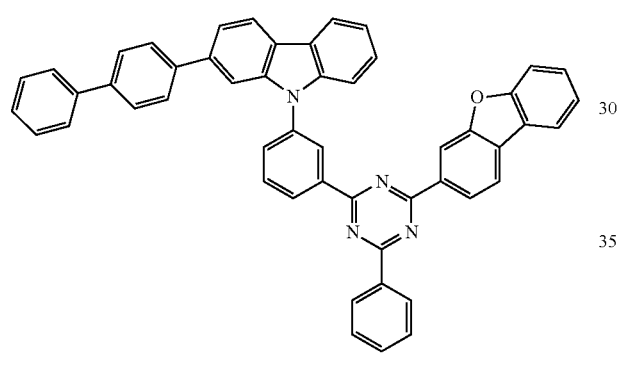
[A-16]
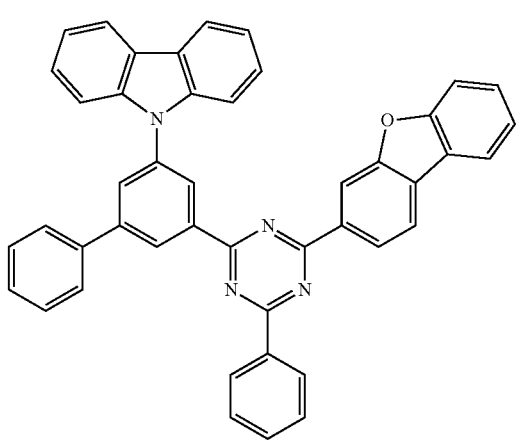
[A-14]
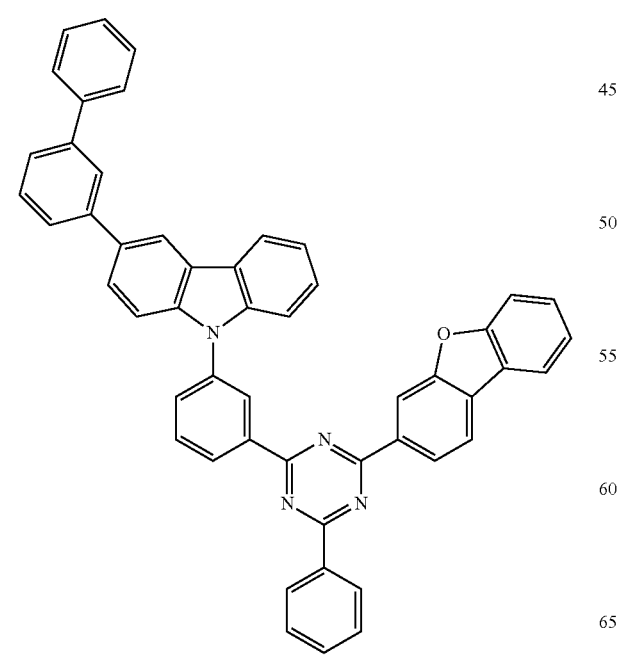
[A-17]
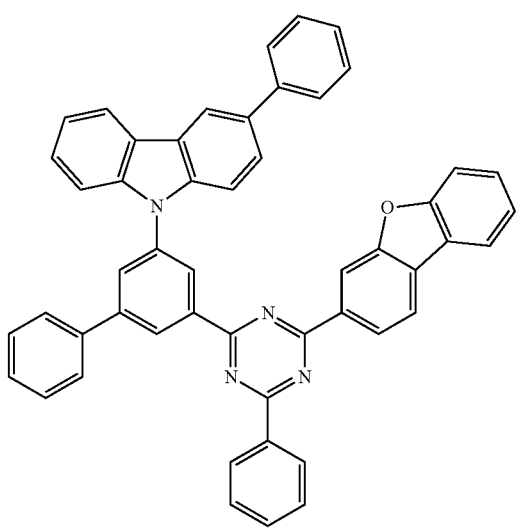

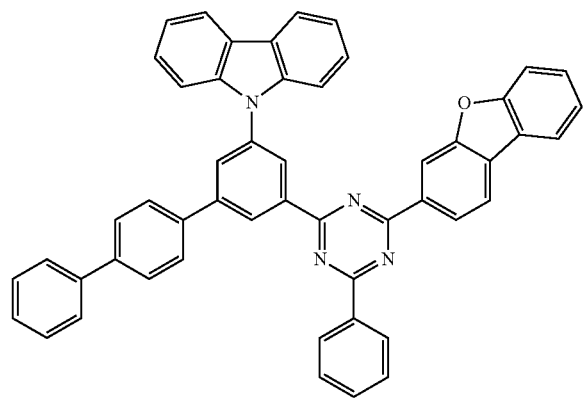
[A-18]
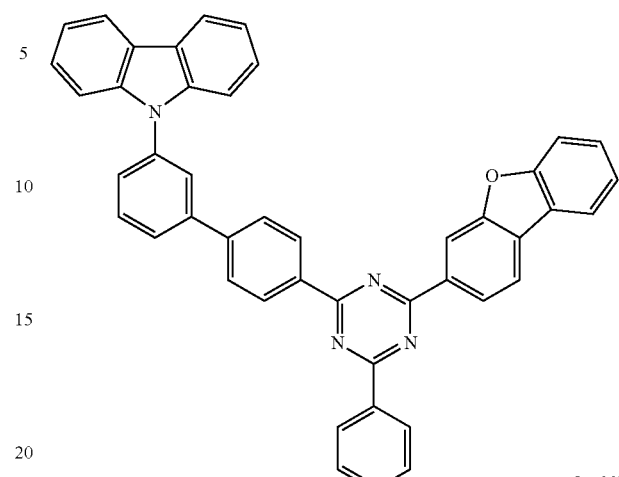
[A-21]
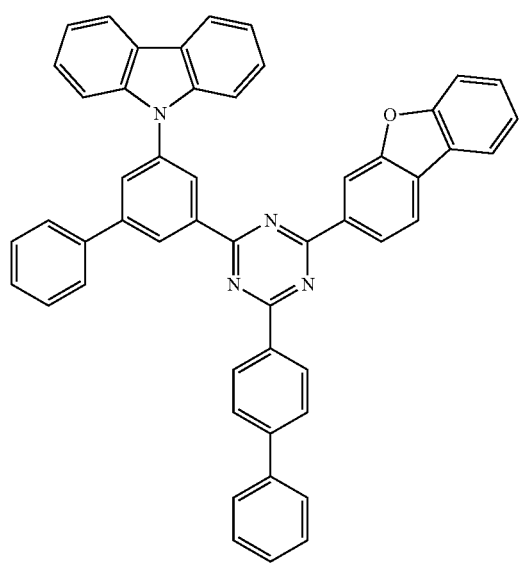
[A-19]
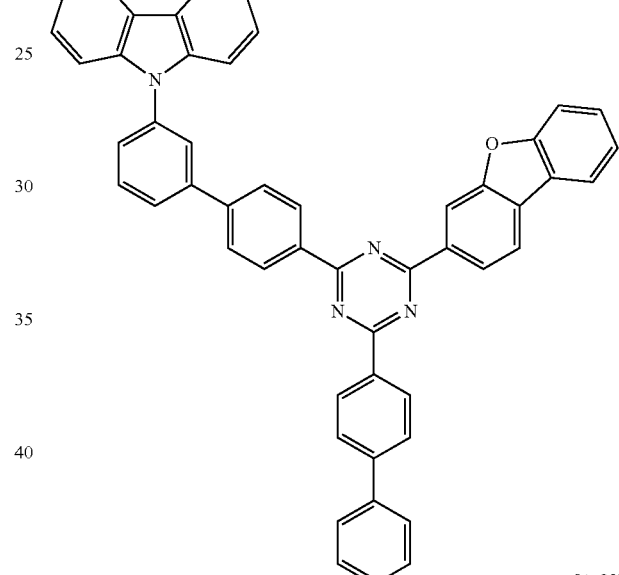
[A-22]
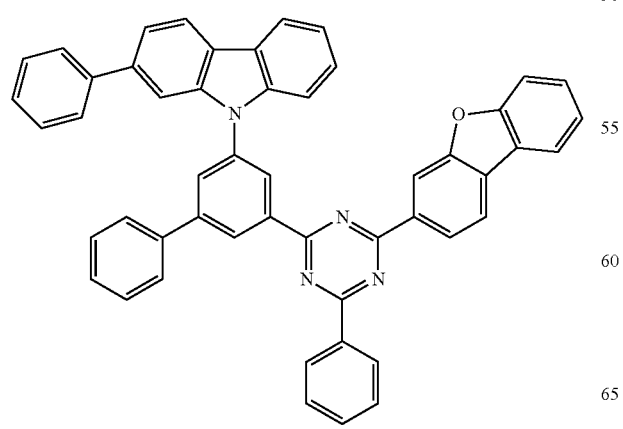
[A-20]
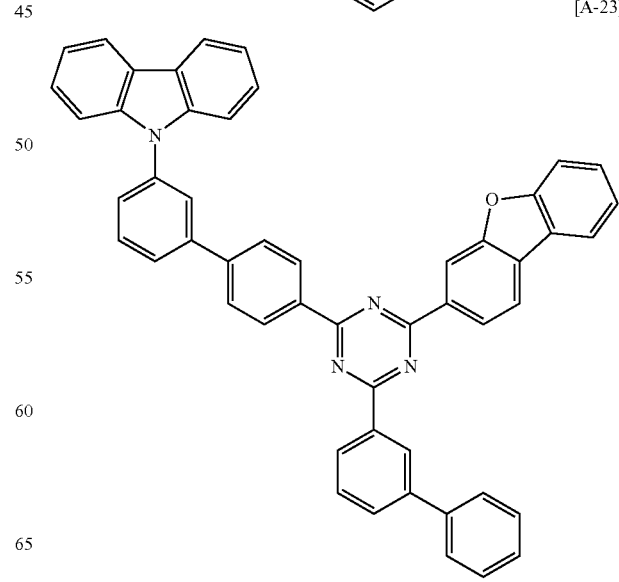
[A-23]

[A-24]
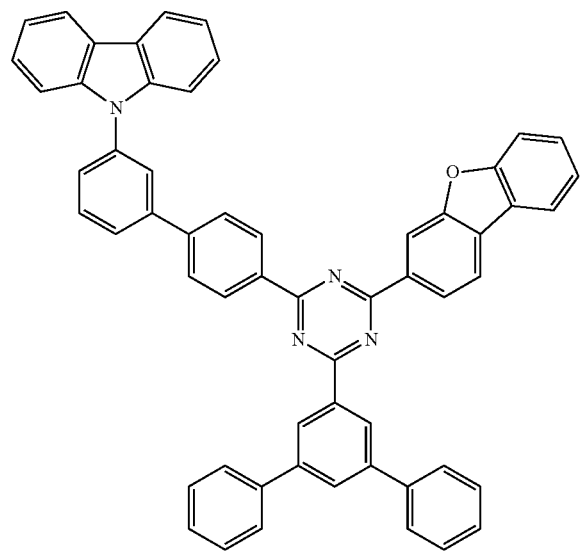
[A-27]
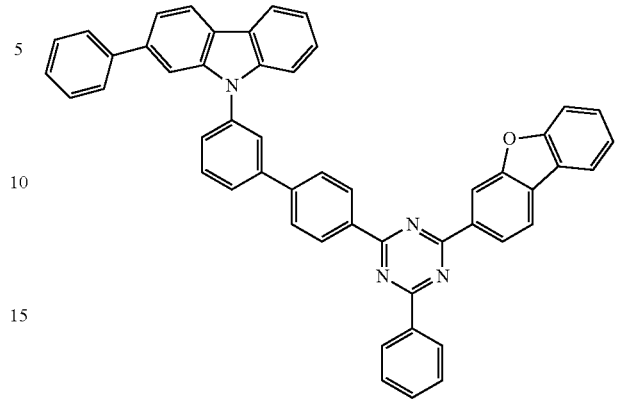
[A-25]
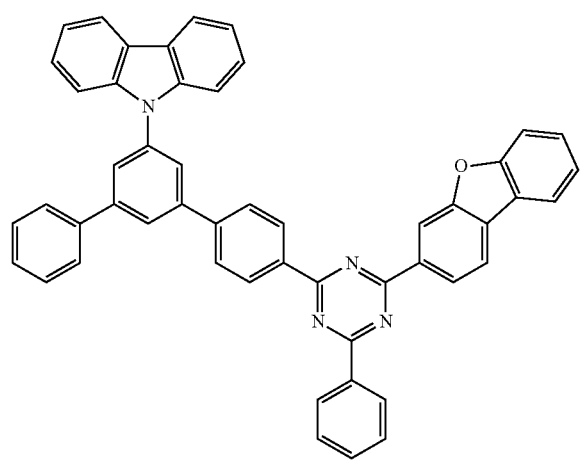
[A-28]
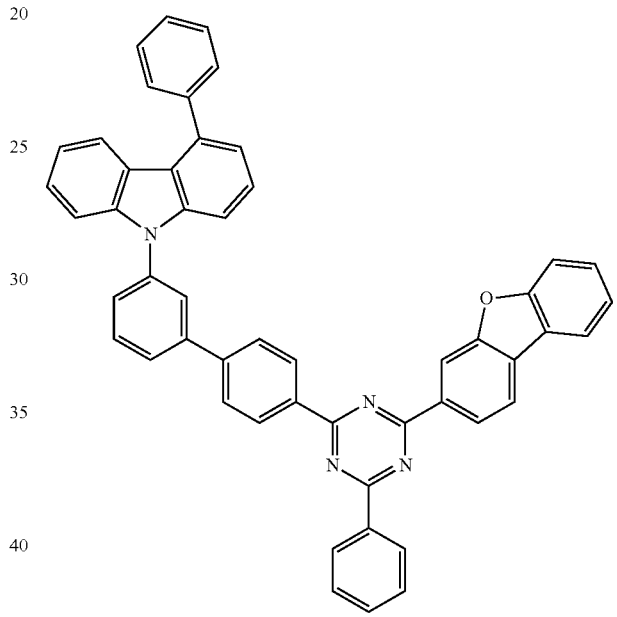
[A-26]
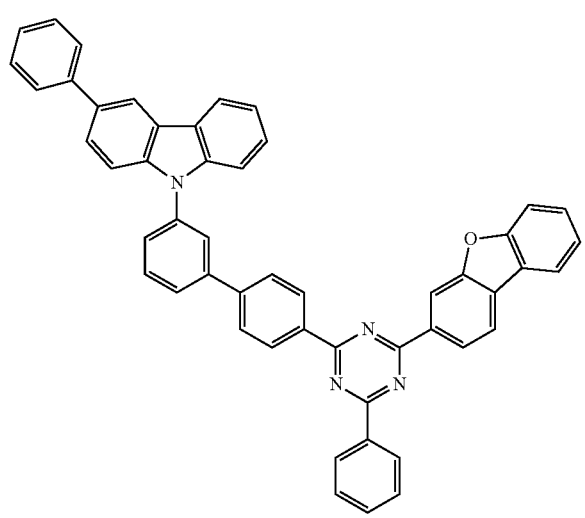
[A-29]
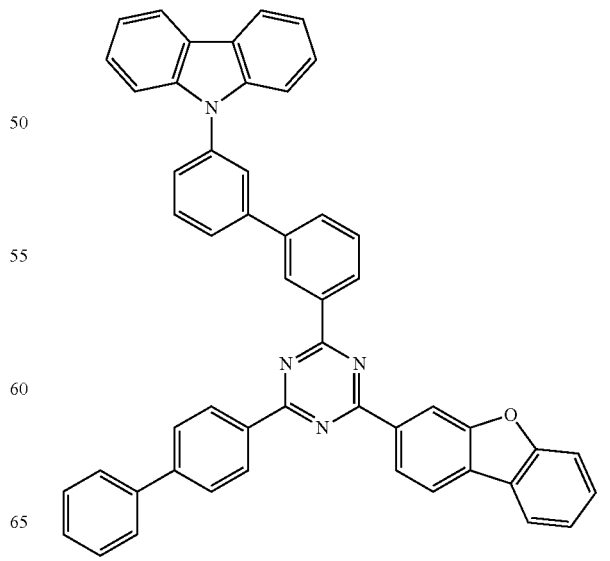

[A-30]
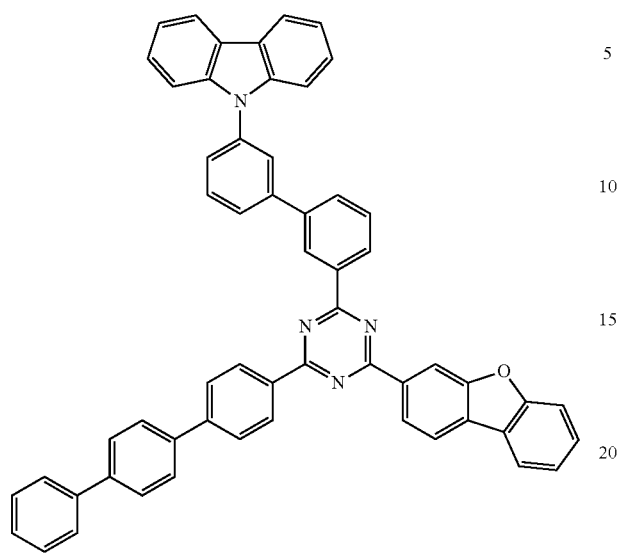
[A-31]
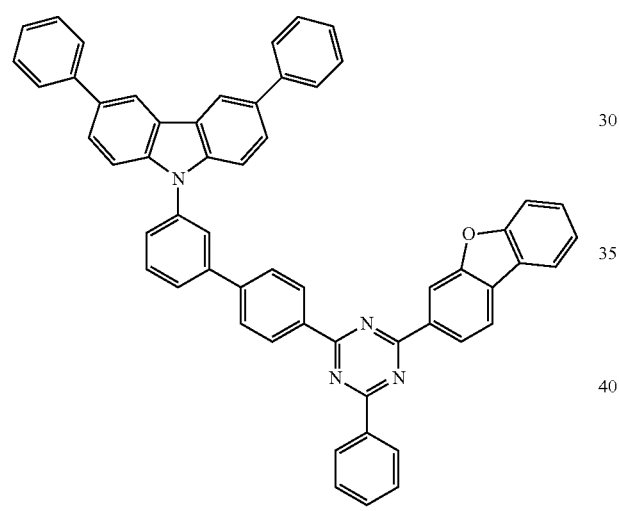
[A-33]
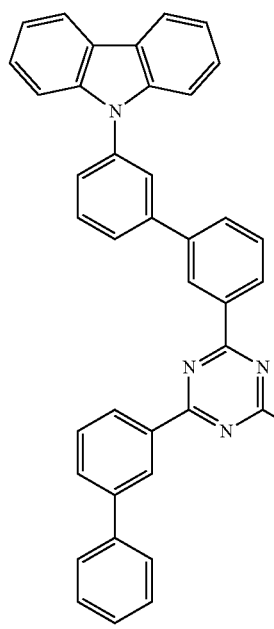
[A-32]
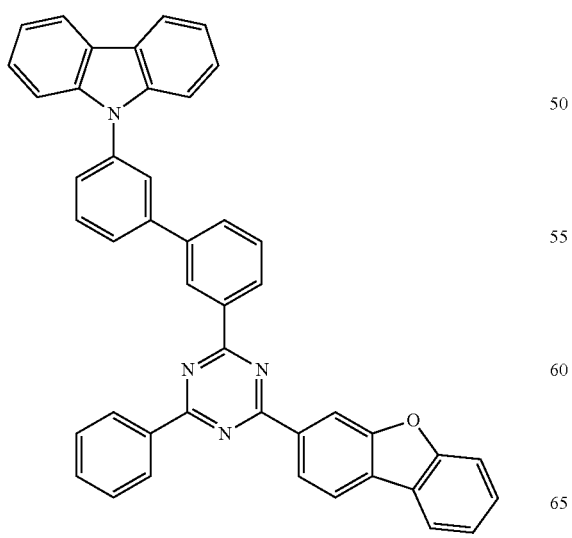
[A-34]
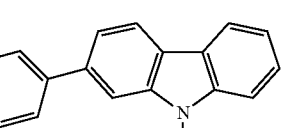

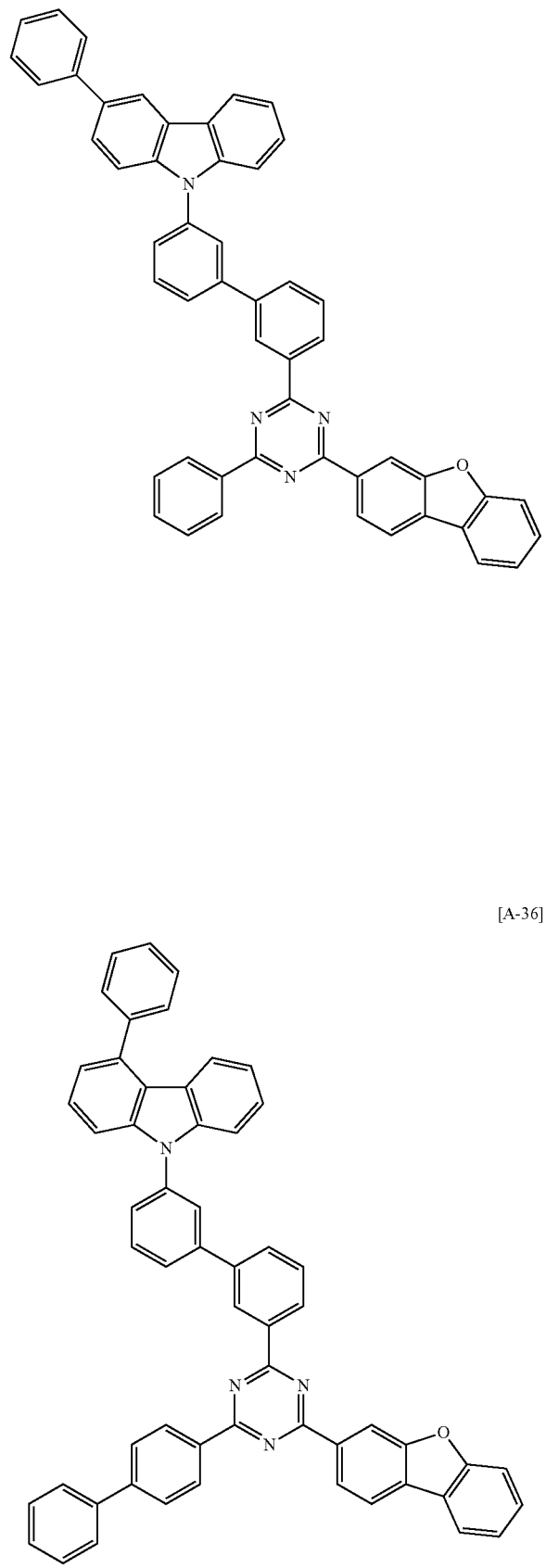
[A-35]
[A-36]
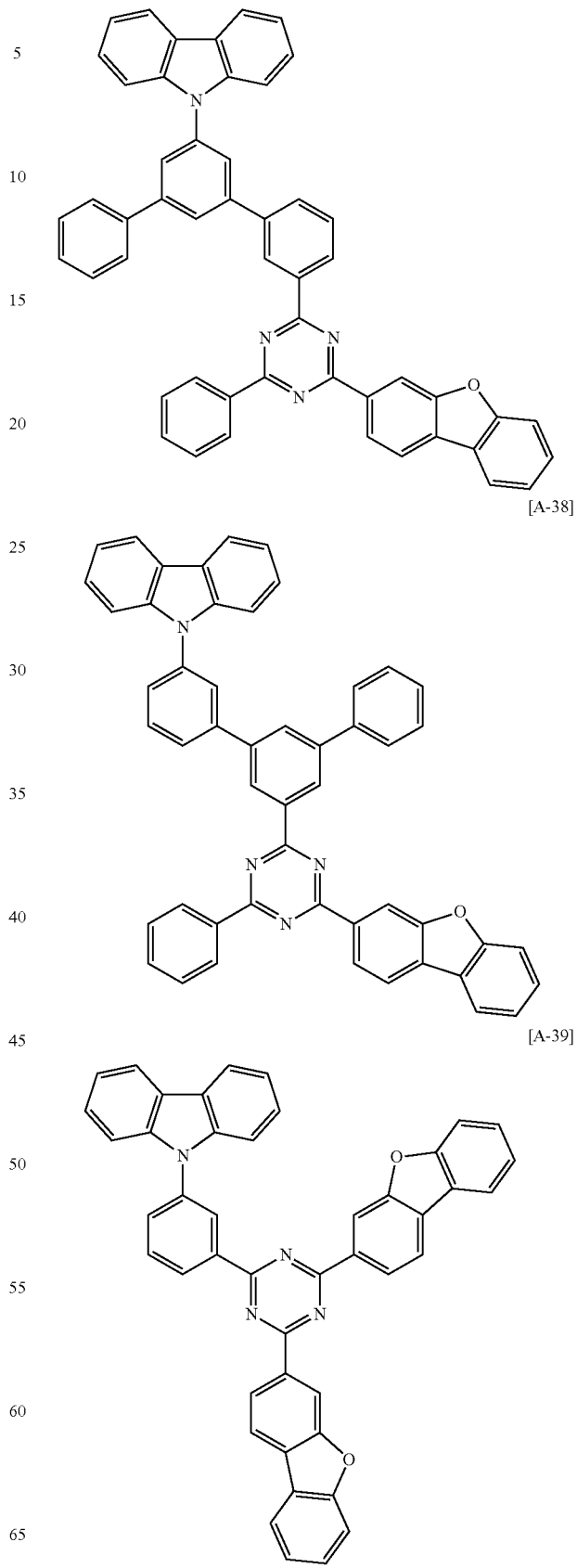
[A-37]
[A-38]
[A-39]

[A-40]
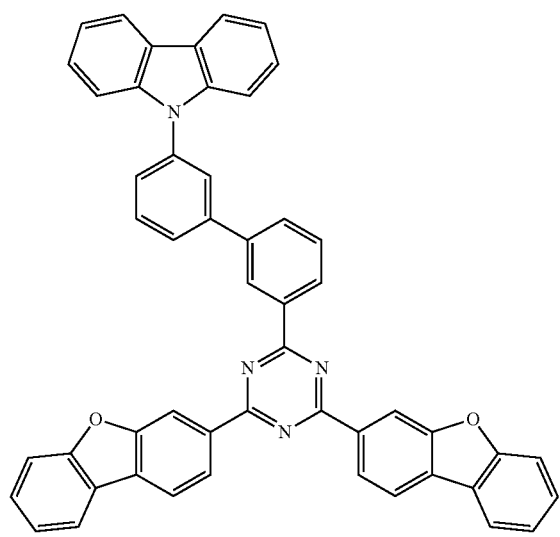
[A-41]
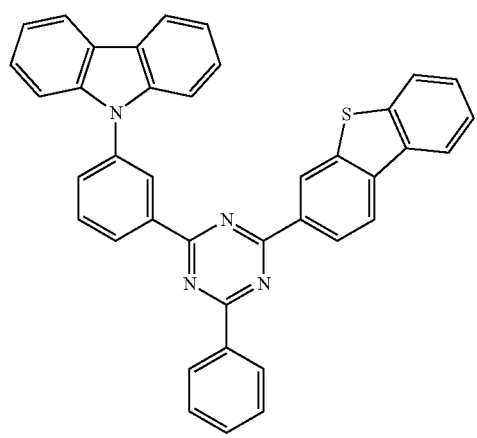
[A-42]
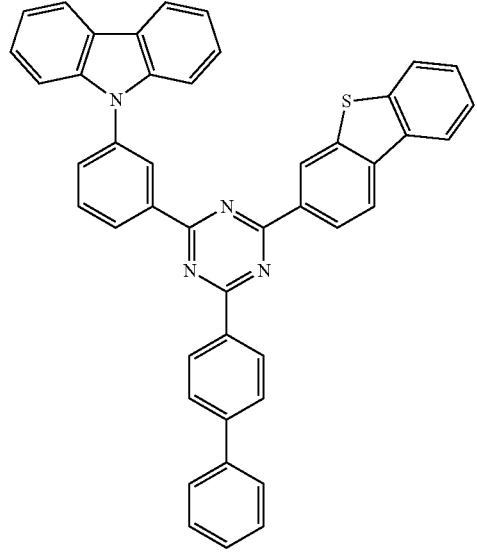
[A-43]
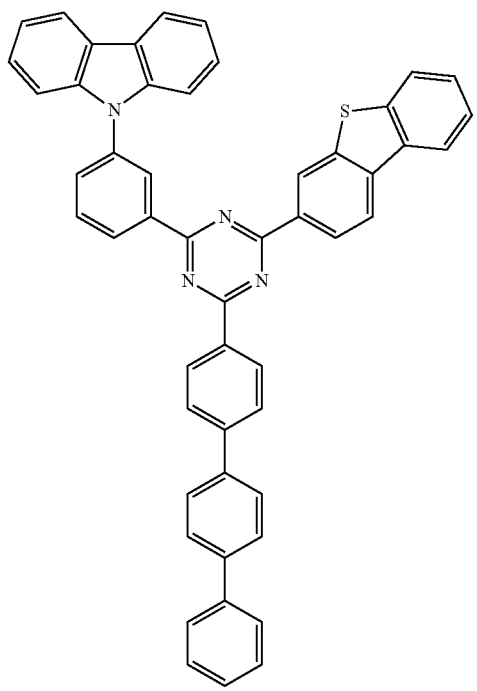
[A-44]
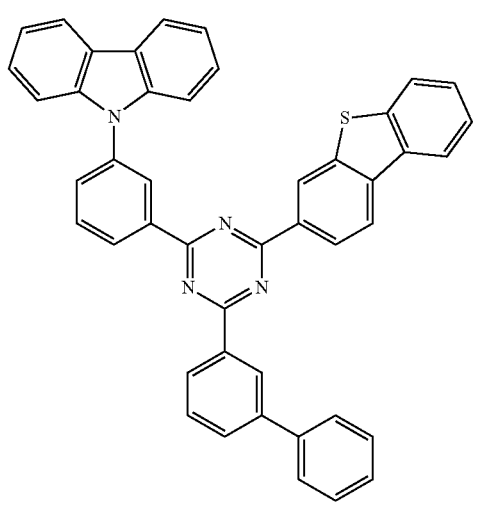

[A-45]
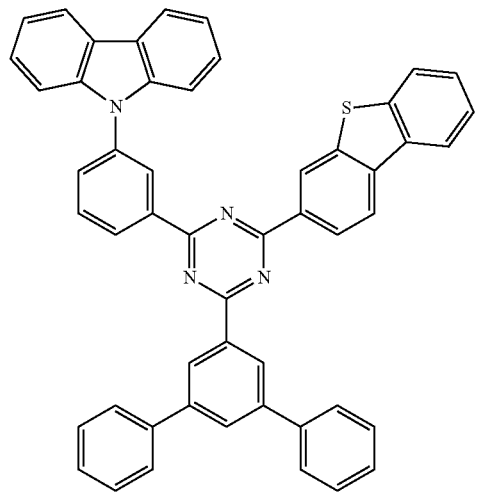
[A-46]
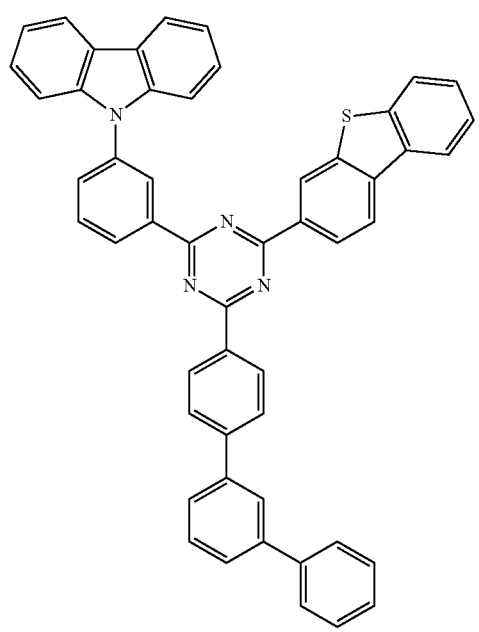
[A-47]
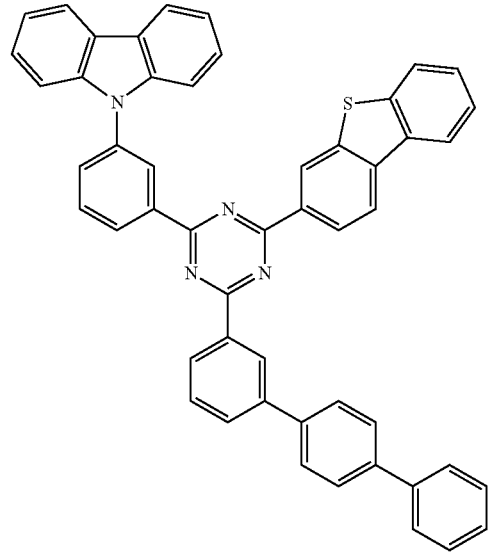
[A-48]
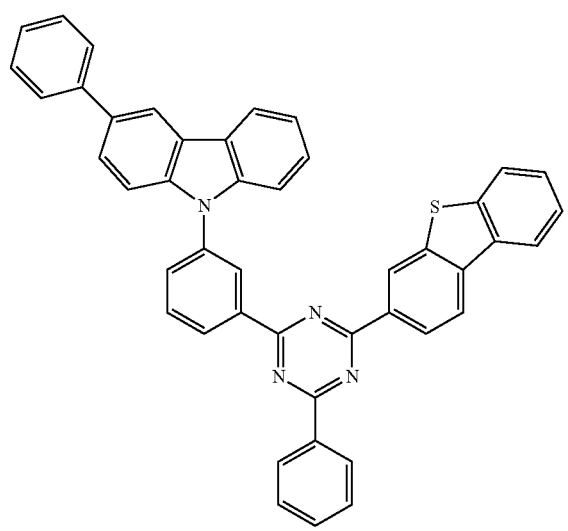
[A-49]
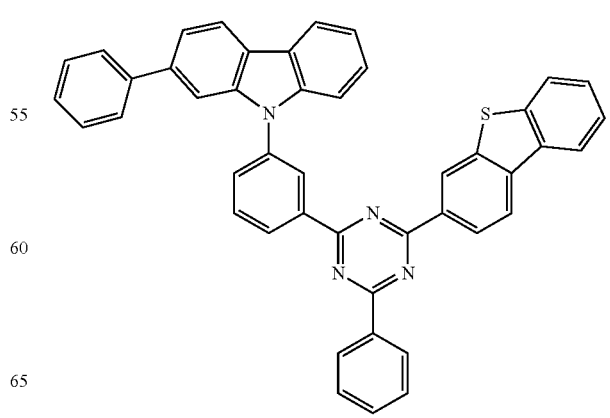

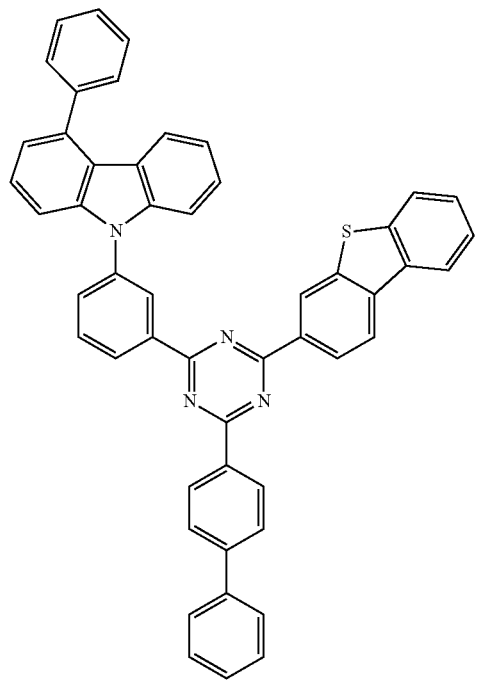
[A-50]
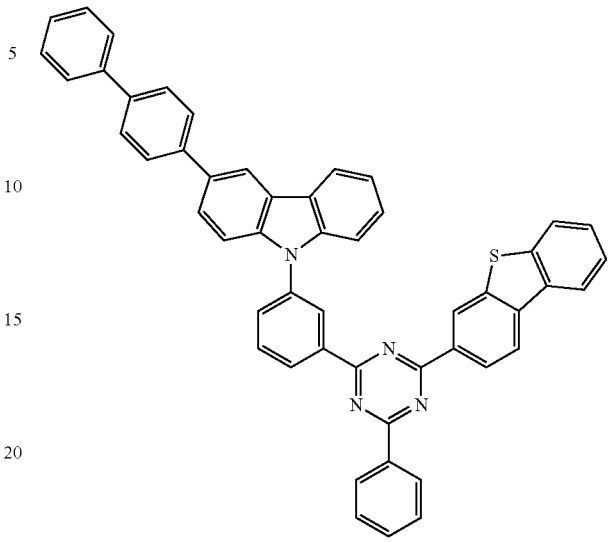
[A-52]
[A-53]
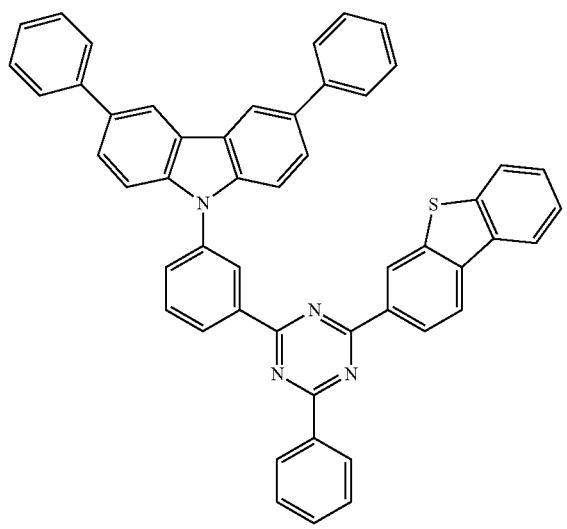
[A-51]
[A-54]

[A-55]
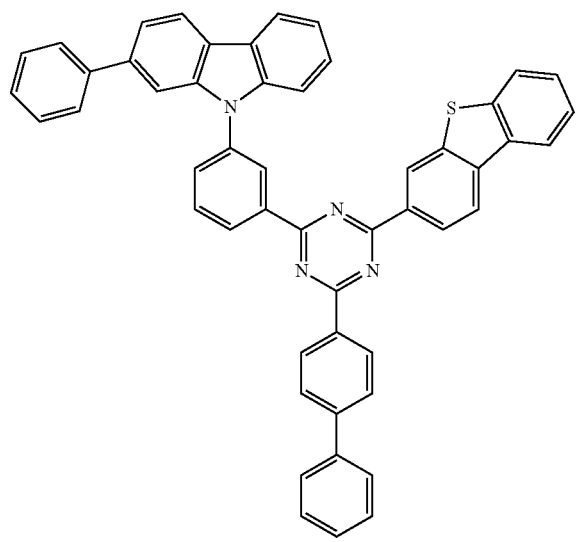
[A-58]
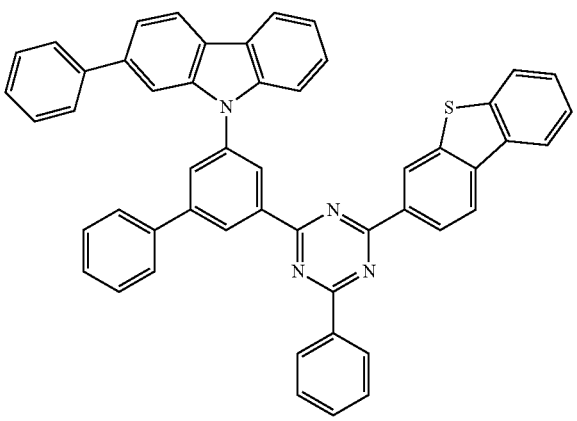
[A-56]
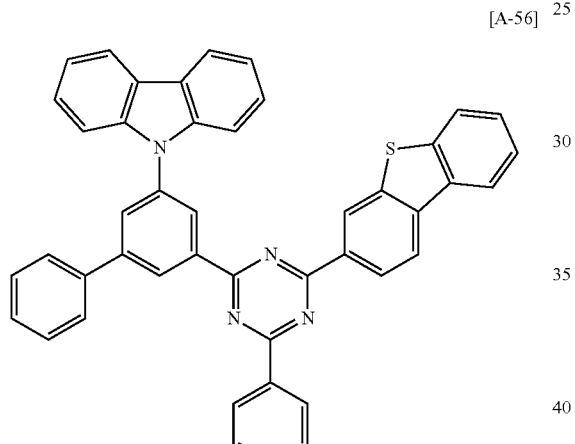
[A-59]
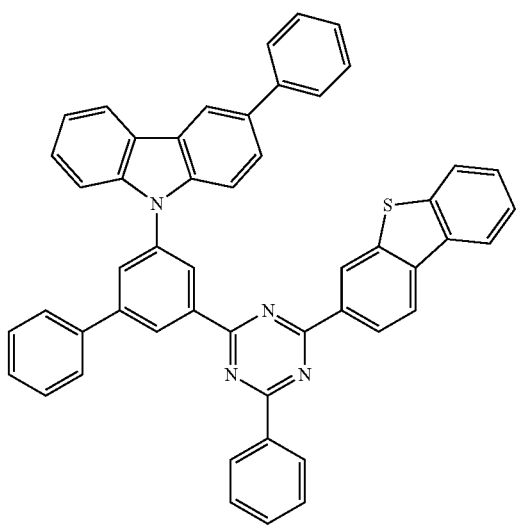
[A-57]
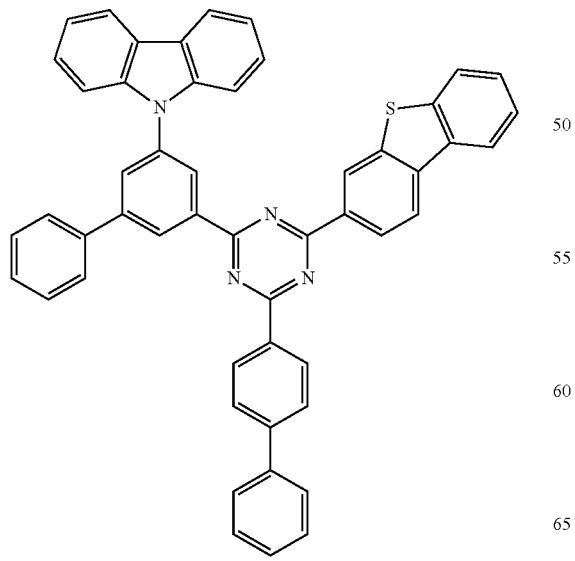
[A-60]
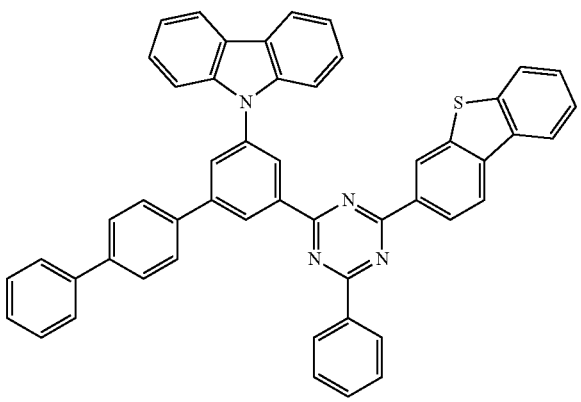

[A-61]
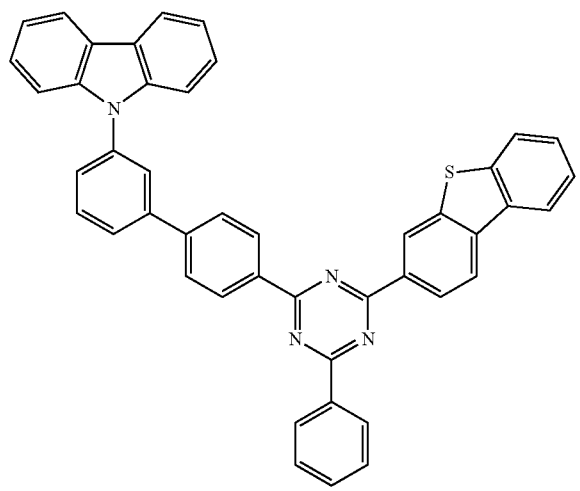
[A-62]
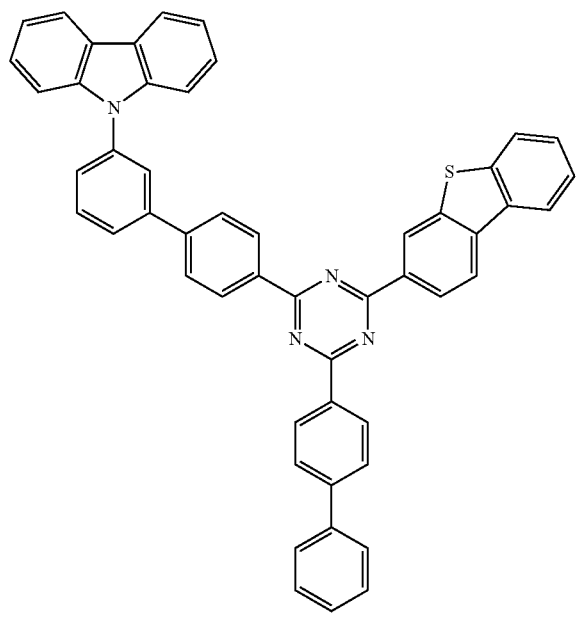
[A-63]
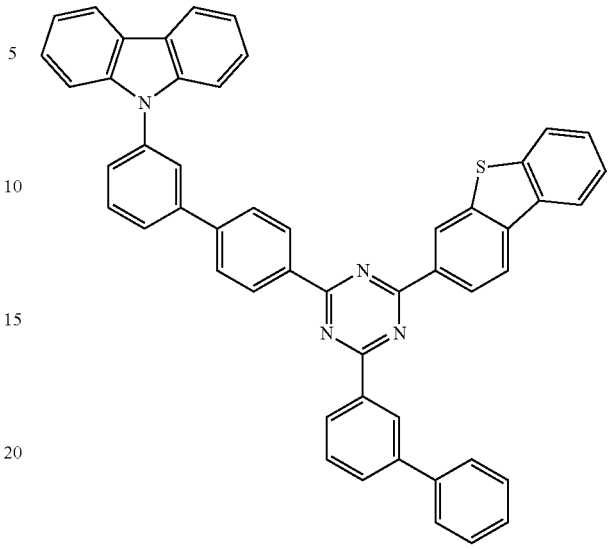
[A-64]
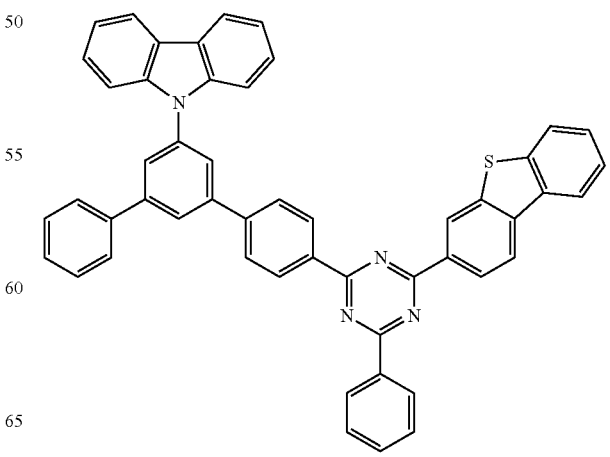
[A-65]

[A-66]
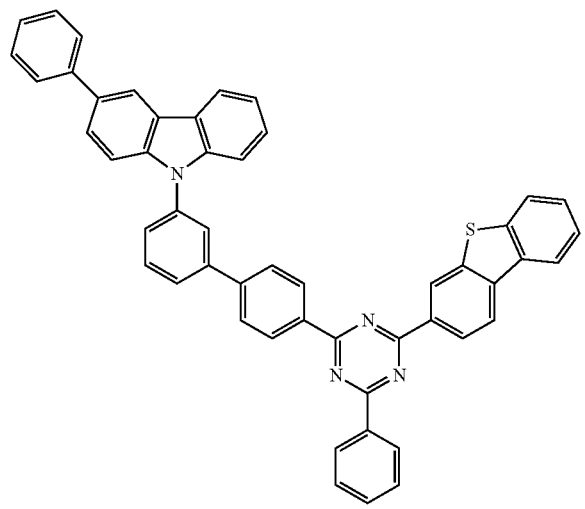
[A-69]
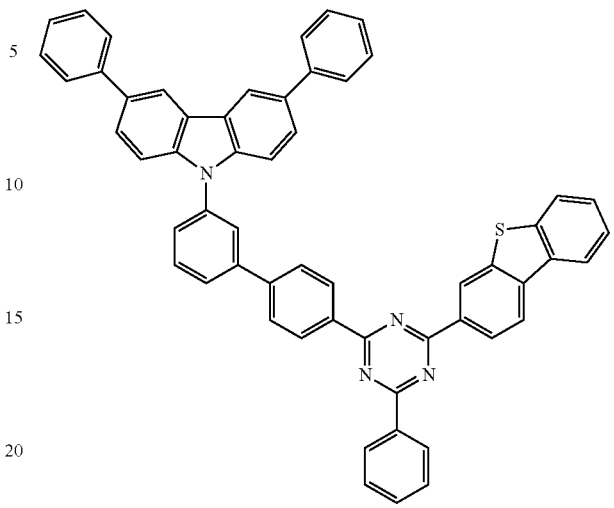
[A-67]
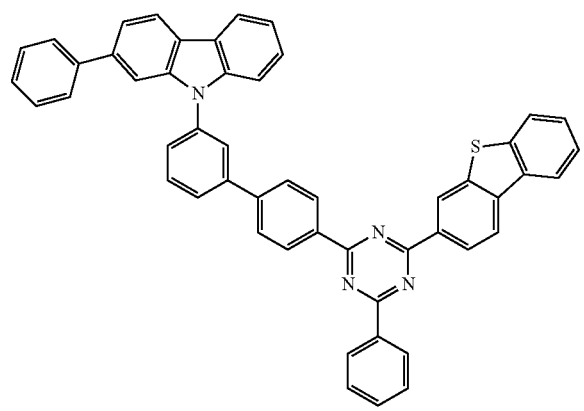
[A-70]
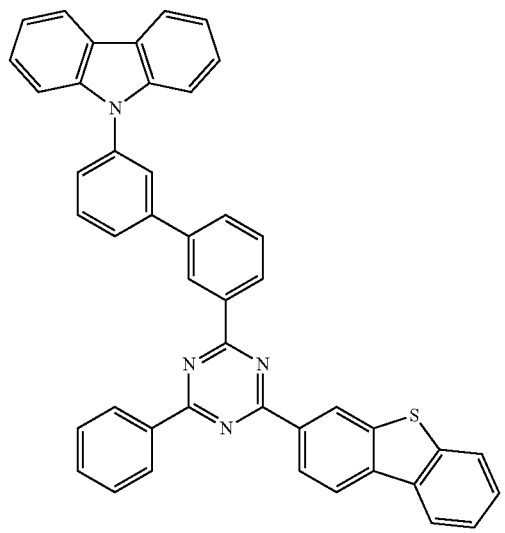
[A-68]
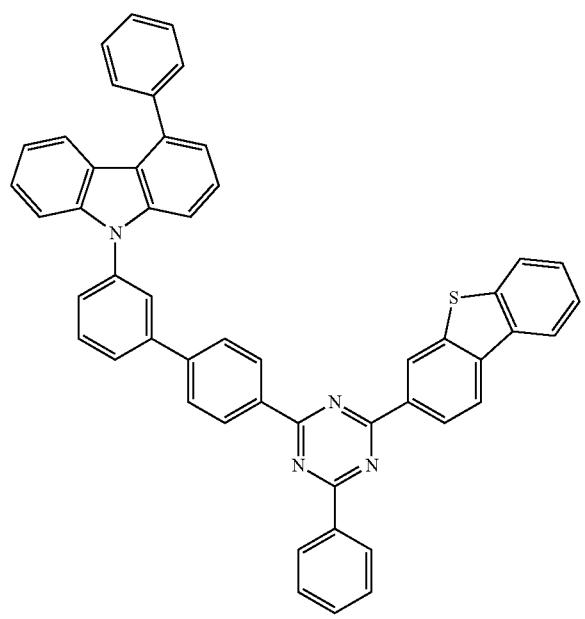
[A-71]
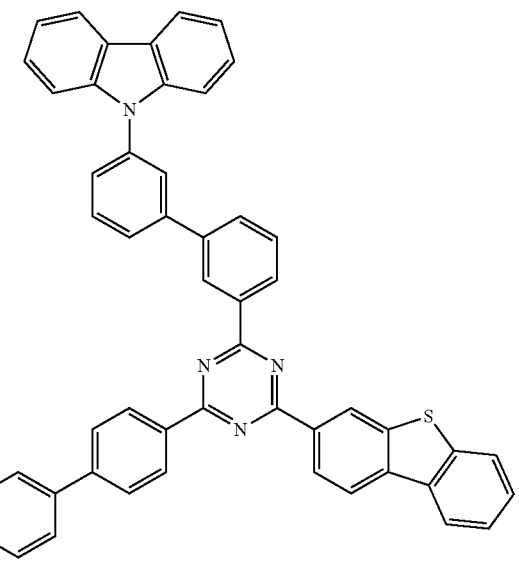

[A-72]
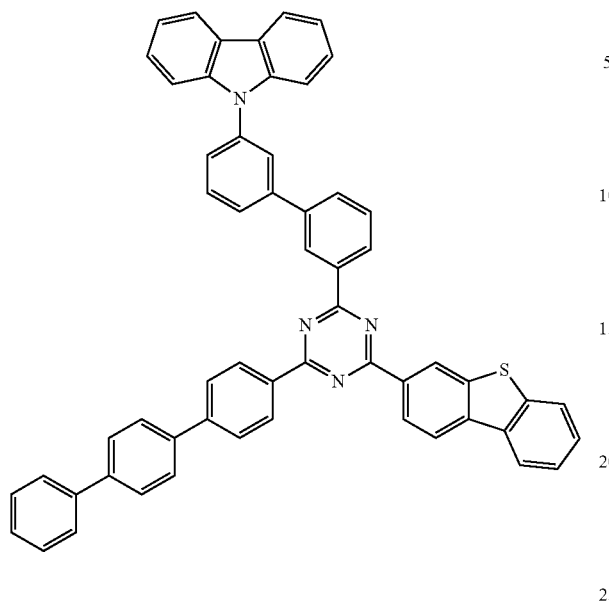
[A-73]
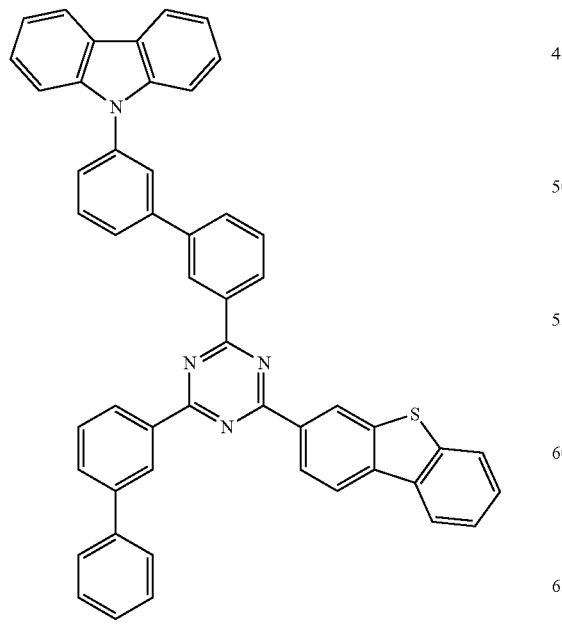
[A-74]
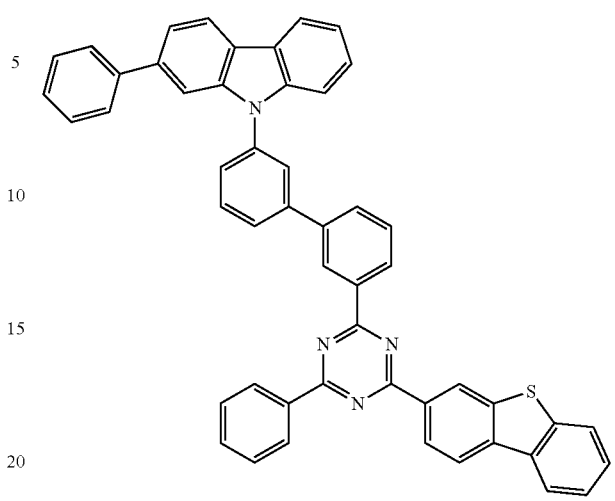
[A-75]
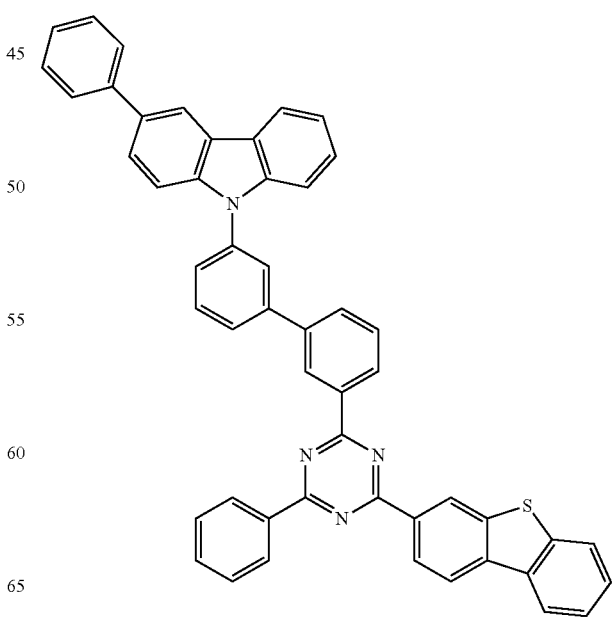

[A-76]
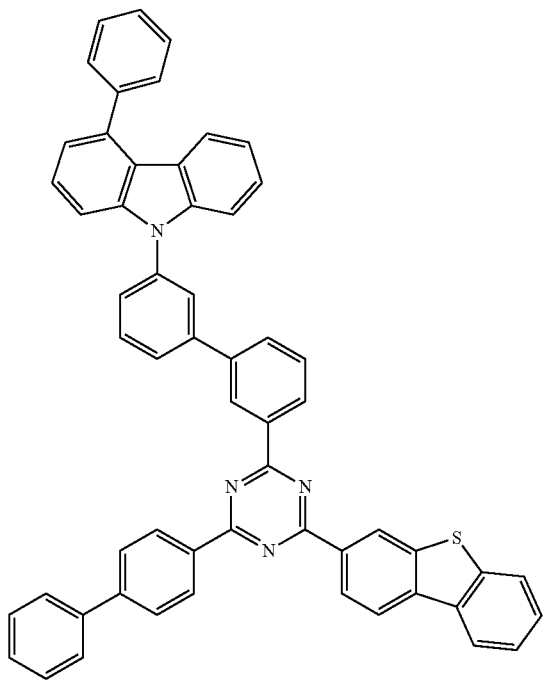
[A-78]
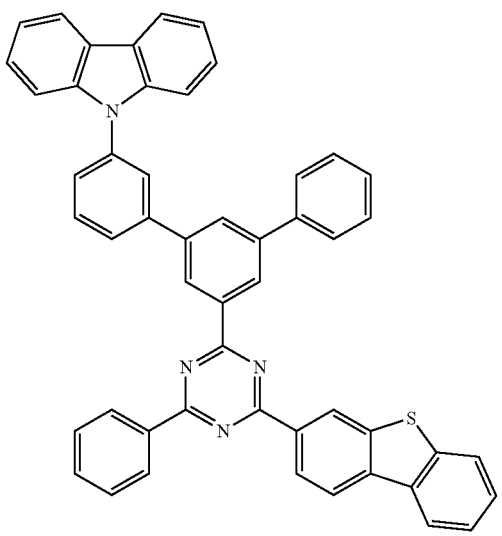
[A-77]
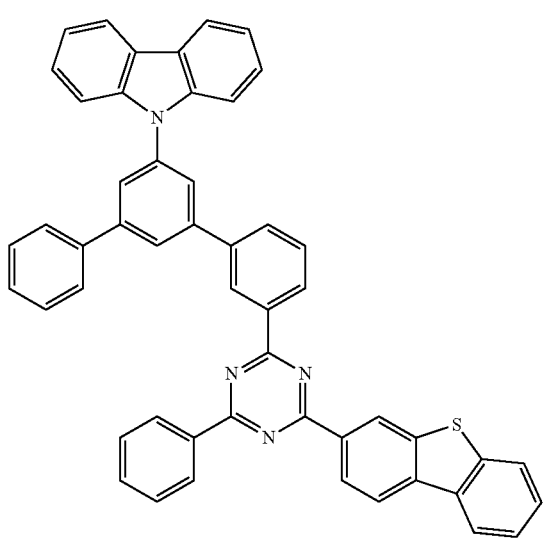
[A-79]
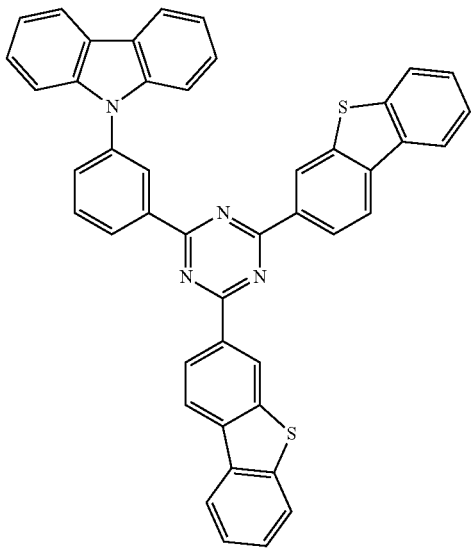

[A-80]

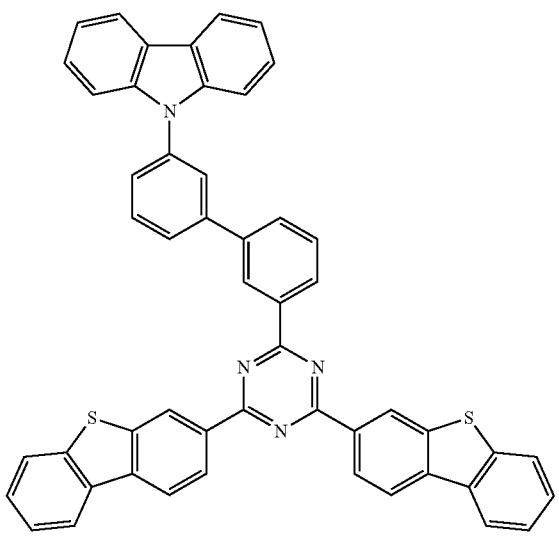

A composition for an organic optoelectronic device according to another embodiment includes the compound for an organic optoelectronic device (hereinafter, "a first compound for an organic optoelectronic device") and a second compound for an organic optoelectronic device represented by Chemical Formula 2; or a combination of Chemical Formula 3 and Chemical Formula 4.

[Chemical Formula 2]

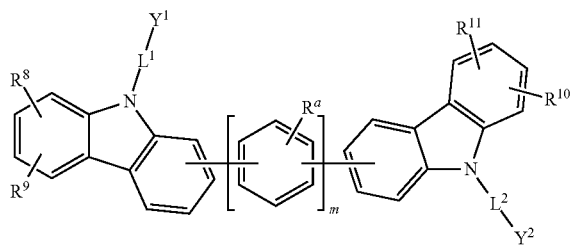

In Chemical Formula 2,
Y$^1$ and Y$^2$ may each independently be a substituted or unsubstituted C6 to C20 aryl group, or a substituted or unsubstituted C2 to C30 heterocyclic group,
L$^1$ and L$^2$ may each independently be a single bond, or a substituted or unsubstituted C6 to C20 arylene group,
R$^a$ and R$^8$ to R$^{11}$ may each independently be hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group, and
m is 0, 1, or 2;

[Chemical Formula 3]

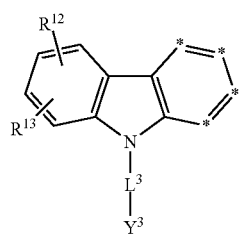

[Chemical Formula 4]

wherein, in Chemical Formulae 3 and 4,
Y$^3$ and Y$^4$ may each independently be a substituted or unsubstituted C6 to C20 aryl group, or a substituted or unsubstituted C2 to C30 heterocyclic group,
adjacent two *'s of Chemical Formula 3 may be bonded with Chemical Formula 4,
other adjacent two *'s of Chemical Formula 3 not being bonded with Chemical Formula 4* may each independently be C-L$^a$-R$^b$,
L$^a$, L$^3$, and L$^4$ may each independently be a single bond, or a substituted or unsubstituted C6 to C20 arylene group, and
R$^b$ and R$^{12}$ to R$^{15}$ may each independently be hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group.

The second compound for an organic optoelectronic device may be used with the first compound for an organic optoelectronic device in the light emitting layer and may help increase charge mobility and stability to improve luminous efficiency and life-span characteristics.

In an example embodiment, Y$^1$ and Y$^2$ of Chemical Formula 2 may each independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group, In an example embodiment, L$^1$ and L$^2$ of Chemical Formula 2 may each independently be a single bond, a substituted or unsubstituted phenylene group, or a substituted or unsubstituted biphenylene group, In an example embodiment, R$^1$ to R$^{11}$ of Chemical Formula 2 may each independently be hydrogen, deuterium, or a substituted or unsubstituted C6 to C12 aryl group, and In an example embodiment, m may be 0 or 1.

In an example embodiment, "substituted" of Chemical Formula 2 may refer to replacement of at least one hydrogen by deuterium, a C1 to C4 alkyl group, a C6 to C18 aryl group, or a C2 to C30 heteroaryl group.

In an example embodiment, Chemical Formula 2 may be one of structures of Group II and *-L$^1$-Y$^1$ and *-L$^2$-Y$^2$ may be one of substituents of Group III.

[Group II]
C-1
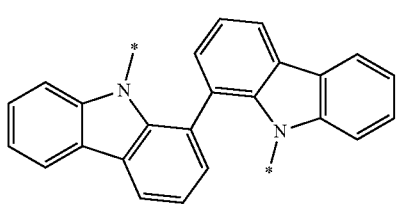
C-2
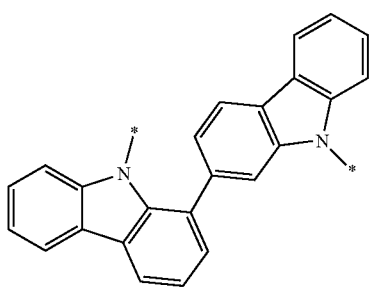
C-3
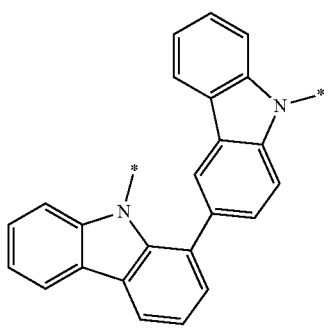
C-4
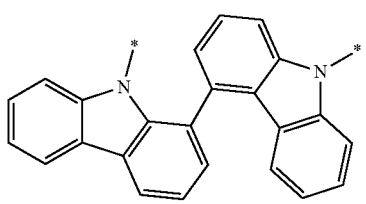
C-5
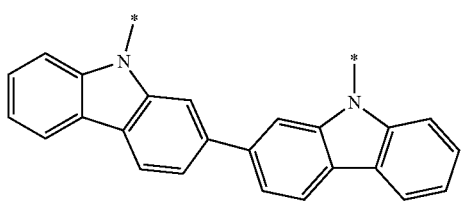
C-6
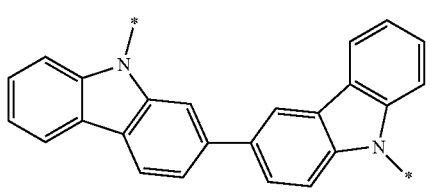
C-7
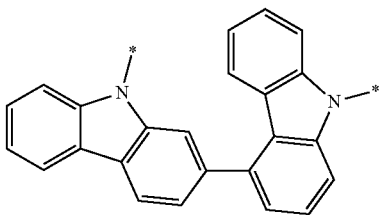
C-8
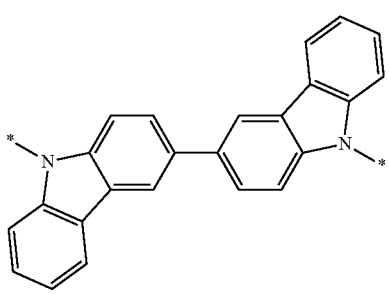
C-9
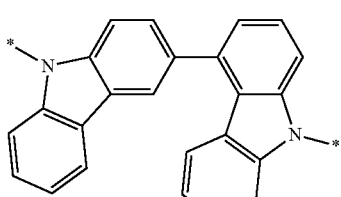
C-10
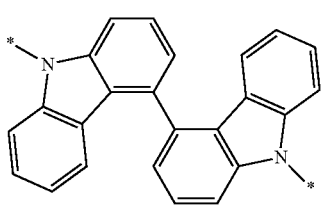
C-11
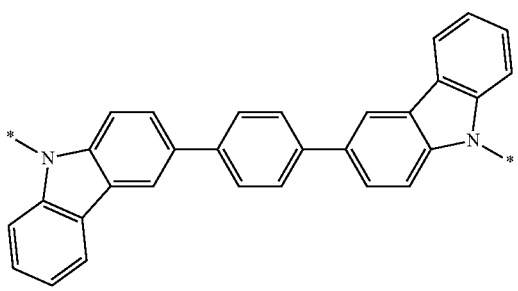
C-12
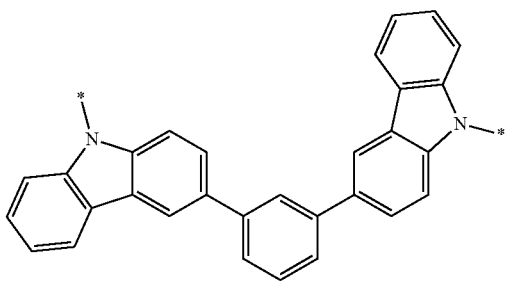

C-13
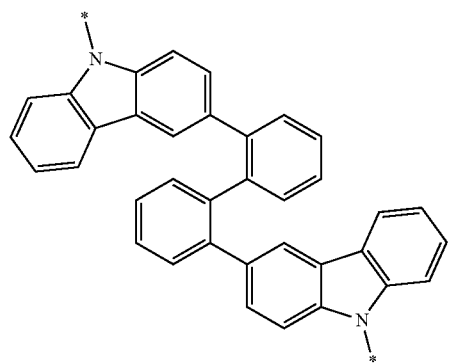
C-14
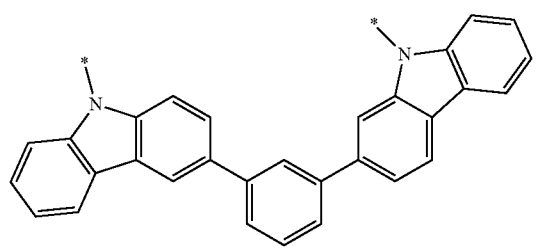
C-15
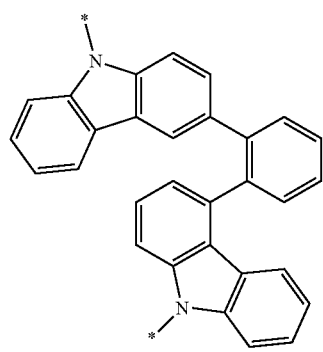
C-16
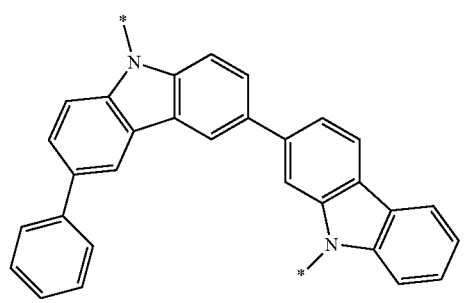
C-17
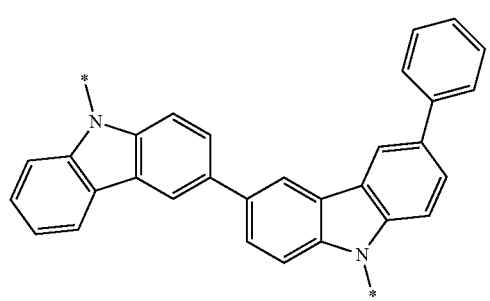
C-18
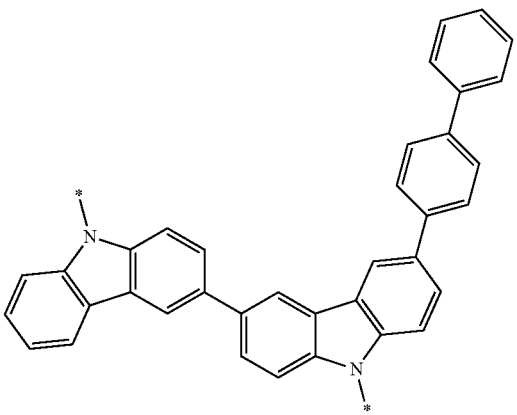
[Group III]
B-1
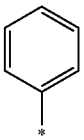
B-2
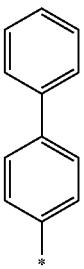
B-3
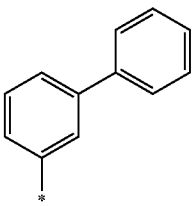
B-4
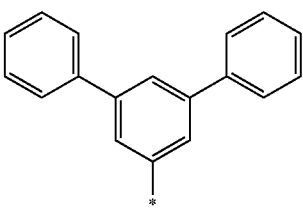
B-5
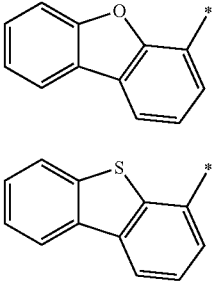
B-6
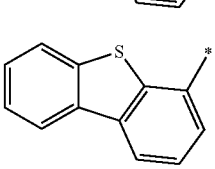

-continued
B-7 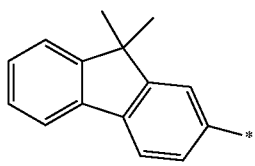
B-8 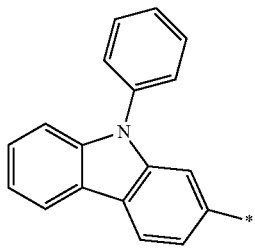
B-9 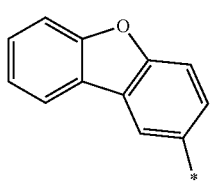
B-10 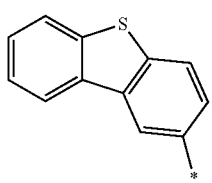
B-11 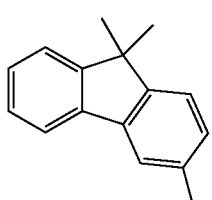
B-12 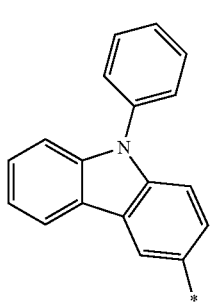
B-13 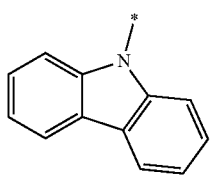
B-14 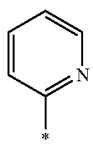
B-15 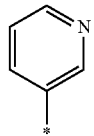
B-16 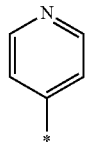
B-17 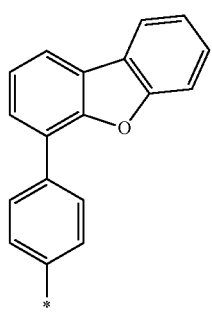
B-18 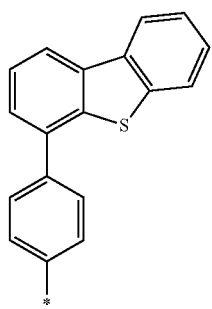
B-19 
B-20 
B-21

B-22 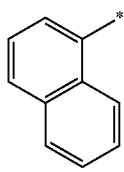

B-23 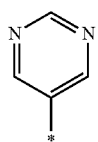

B-24 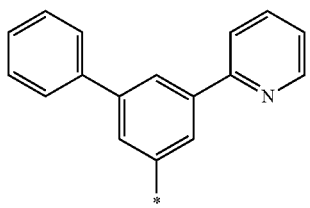

B-25 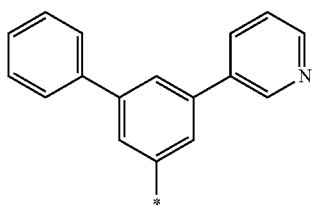

B-26 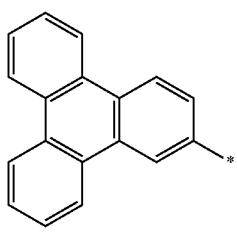

B-27 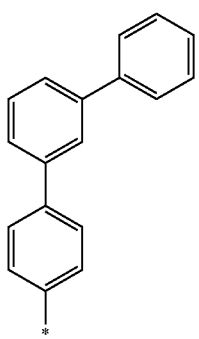

B-28 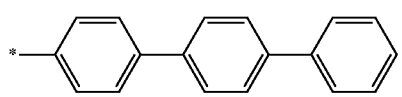

B-29 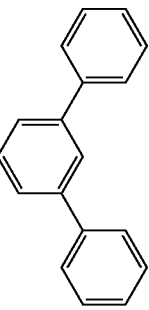

In Group II and Group III, * is a linking point.

In an example embodiment, Chemical Formula 2 may be represented by Chemical Formula C-8 or Chemical Formula C-17 of Group II, and *-L$^1$-Y$^1$ and *-L$^2$-Y$^2$ may be selected from Group III.

For example, Y$^1$ and Y$^2$ of Chemical Formula 2 may each independently be a substituted or unsubstituted phenyl group, a substituted or unsubstituted biphenyl group, a substituted or unsubstituted carbazolyl group, a substituted or unsubstituted dibenzofuranyl group or a substituted or unsubstituted dibenzothiophenyl group, and for example *-L$^1$-Y$^1$ and *-L$^2$-Y$^2$ may be selected from B-1, B-2, and B-3 of Group III.

In an example embodiment, Chemical Formula 2 may be represented by Chemical Formula 2A.

[Chemical Formula 2A]

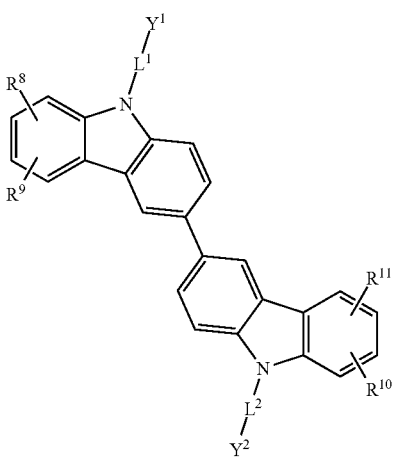

In Chemical Formula 2A, Y$^1$ and Y$^2$, L$^1$ and L$^2$, R$^8$ to R$^{11}$ are the same as described above.

In an example embodiment, the second compound for an organic optoelectronic device represented by a combination of Chemical Formula 3 and Chemical Formula 4 may be represented by one of Chemical Formula 3A, Chemical Formula 3B, Chemical Formula 3C, Chemical Formula 3D, and Chemical Formula 3E.

[Chemical Formula 3A]

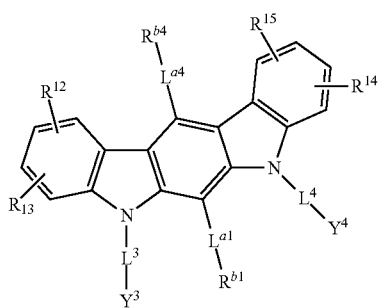

[Chemical Formula 3B]

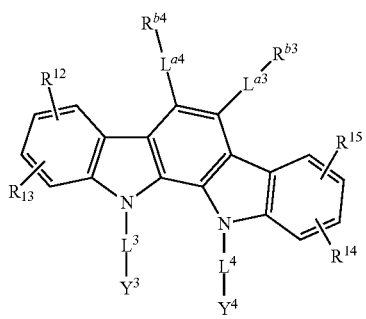

[Chemical Formula 3C]

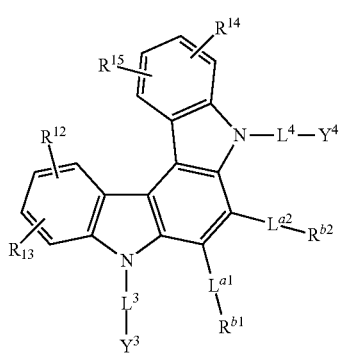

[Chemical Formula 3D]

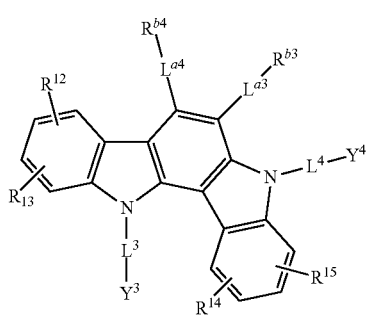

[Chemical Formula 3E]

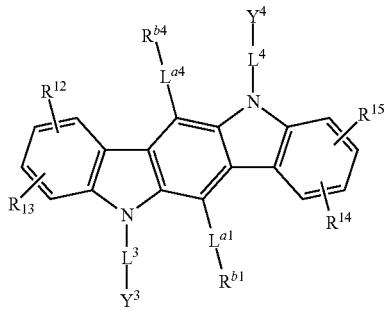

In Chemical Formula 3A to Chemical Formula 3E, $Y^3$ and $Y^4$, $L^3$ and $L^4$ and $R^{12}$ to $R^{15}$ are the same as described above, $L^{a1}$ to $L^{a4}$ are the same as definitions of $L^3$ and $L^4$, and $R^{b1}$ to $R^{b4}$ are the same as definitions of $R^{12}$ to $R^{15}$.

In an example embodiment, $Y^3$ and $Y^4$ of Chemical Formulae 3 and 4 may each independently be a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, $R^{b1}$ to $R^{b4}$ and $R^{12}$ to $R^{15}$ may each independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an example embodiment, $Y^3$ and $Y^4$ of Chemical Formulae 3 and 4 may each independently be selected from substituents of Group IV.

[Group IV]

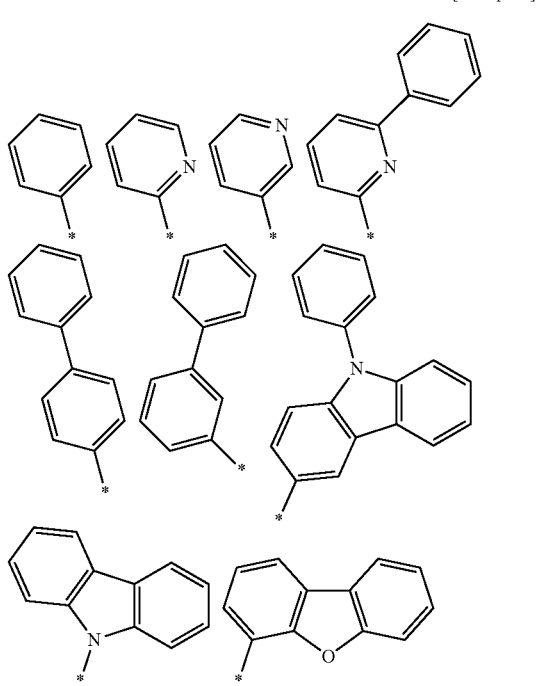

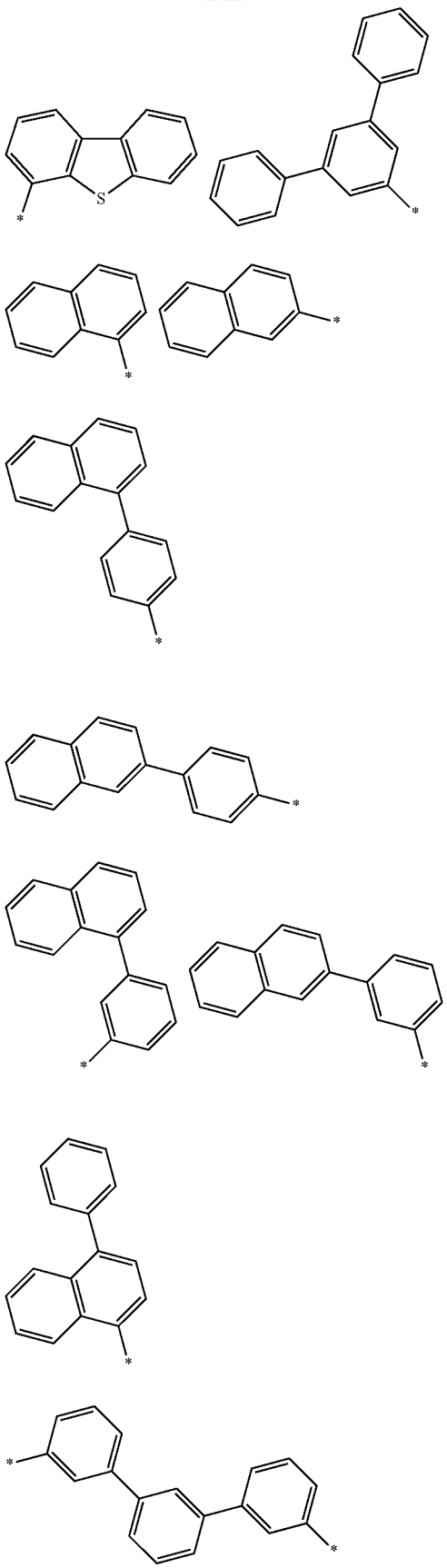
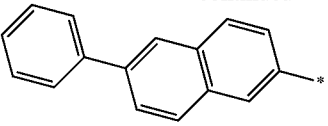

In Group IV, * is a linking point with $L^3$ and $L^4$.

In an example embodiment, $R^{b1}$ to $R^{b4}$ and $R^{12}$ to $R^{15}$ may each independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an example embodiment, $R^{b1}$ to $R^{b4}$ and $R^{12}$ to $R^{15}$ may each independently be hydrogen, deuterium, a cyano group, or a substituted or unsubstituted phenyl group, In an example embodiment, $R^{b1}$ to $R^{b4}$ may be hydrogen and $R^{12}$ to $R^{15}$ may each independently be hydrogen or a phenyl group.

In an example embodiment, the first compound for an organic optoelectronic device may be represented by Chemical Formula 1-1 or Chemical Formula 1-2 and the second compound for an organic optoelectronic device may be represented by Chemical Formula 2A or Chemical Formula 3C.

In an example embodiment, $R^1$ to $R^4$ of Chemical Formula 1-1 and Chemical Formula 1-2 may each independently be hydrogen, deuterium, a substituted or unsubstituted C1 to C6 alkyl group, or a substituted or unsubstituted phenyl group, the $Ar^1$ and $Ar^2$ may each independently be a substituted or unsubstituted phenyl group, a substituted or unsubstituted biphenyl group, a substituted or unsubstituted terphenyl group, a substituted or unsubstituted naphthyl group, or the group represented by Chemical Formula A, provided that one of $Ar^1$ and $Ar^2$ is the group represented by Chemical Formula A, In an example embodiment, $Y^1$ to $Y^4$ of Chemical Formula 2A and Chemical Formula 3C may each independently be a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, $L^1$ to $L^4$, $L^{a1}$, and $L^{a2}$ may each independently be a single bond, or a substituted or unsubstituted C6 to C20 arylene group, and $R^{b1}$, $R^{b2}$, and $R^8$ to $R^{15}$ may each independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an example embodiment, the second compound for an organic optoelectronic device may be one of compounds of Group 2.

[Group 2]
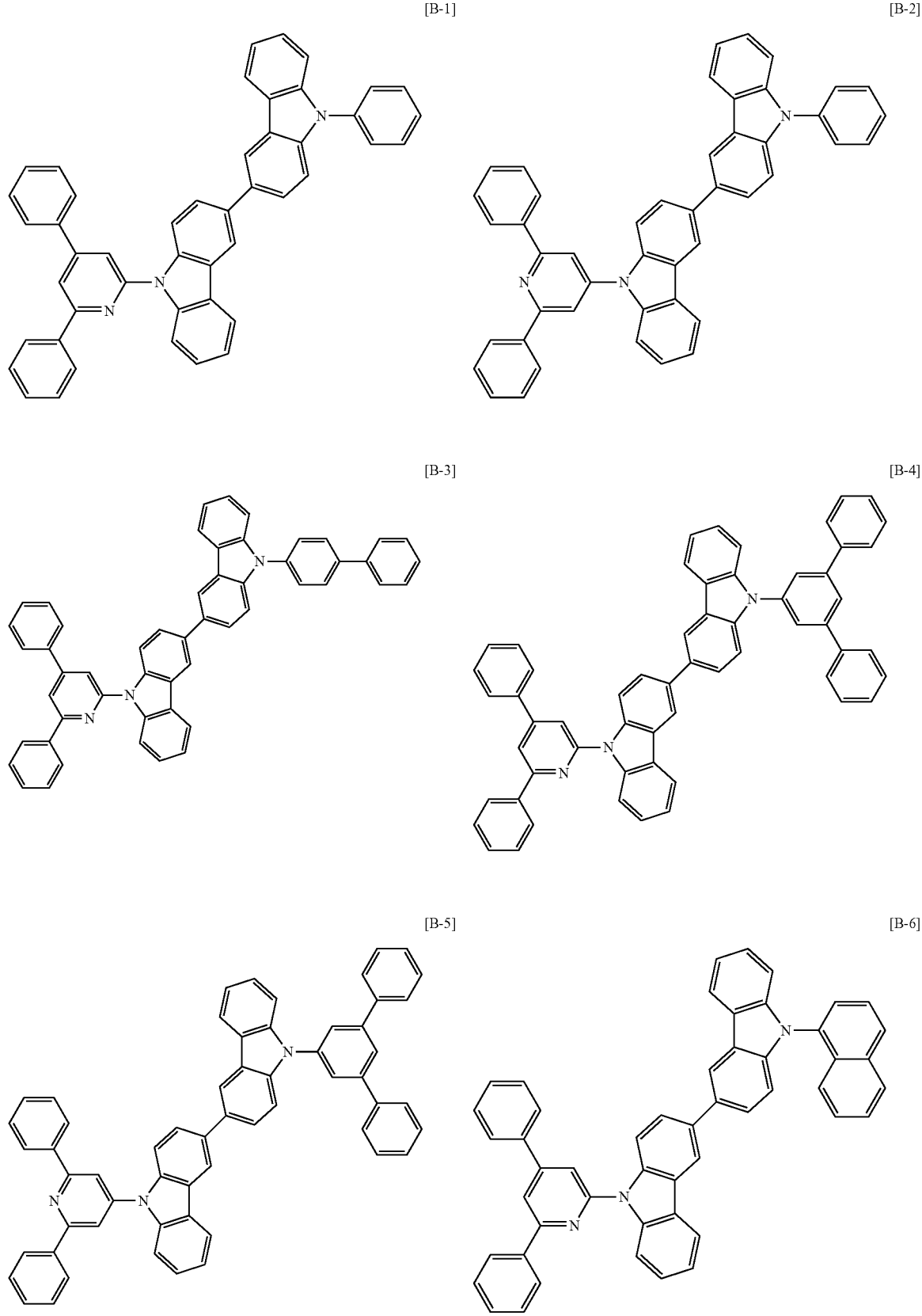

-continued
[B-7]
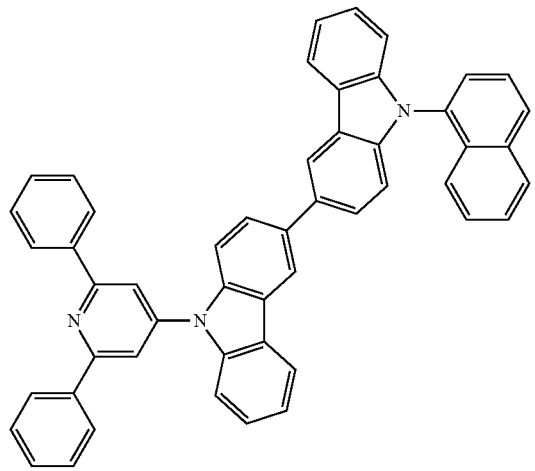
[B-8]
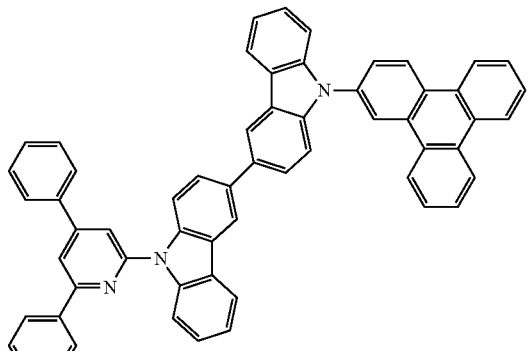
[B-9]
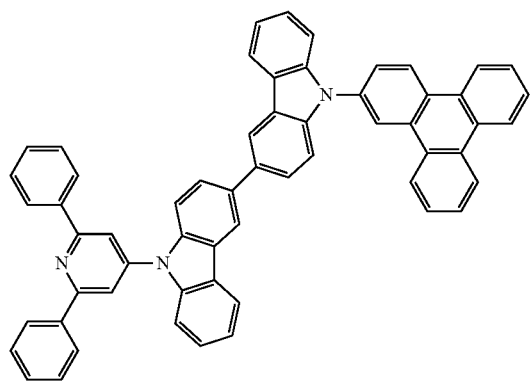
[B-10]
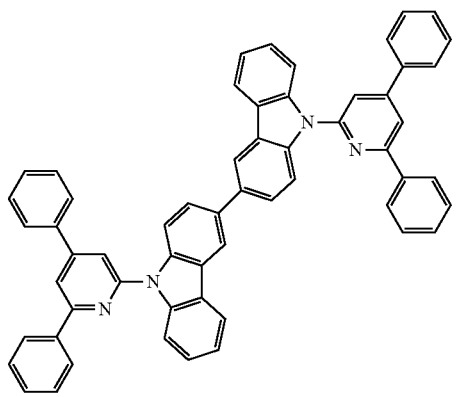
[B-11]
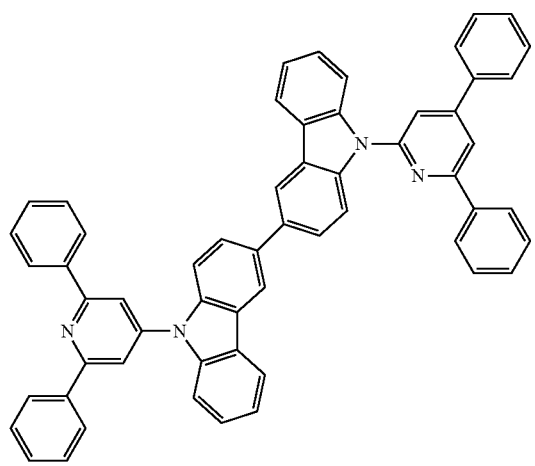
[B-12]
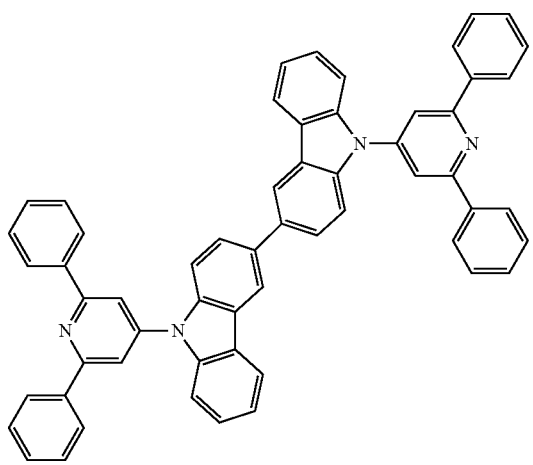

-continued
[B-13]
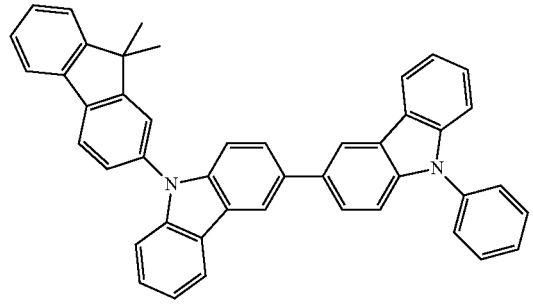
[B-14]
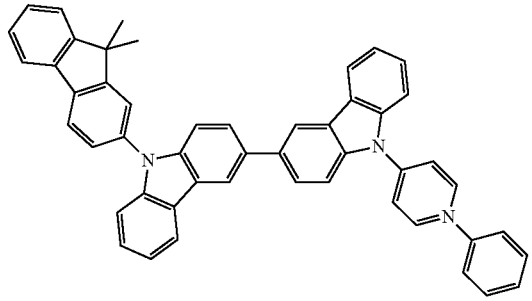
[B-15]
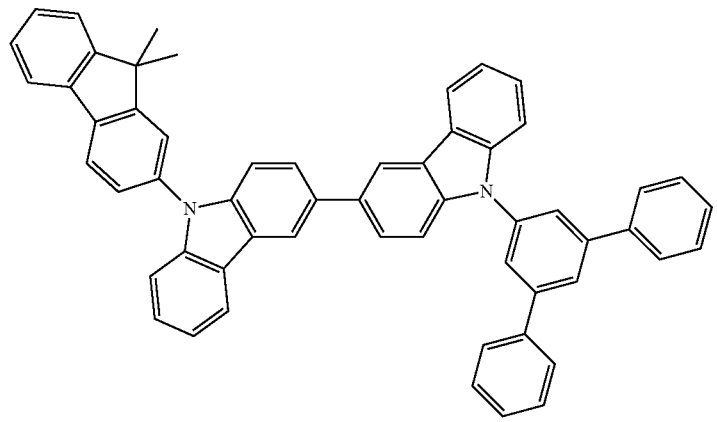
[B-16]
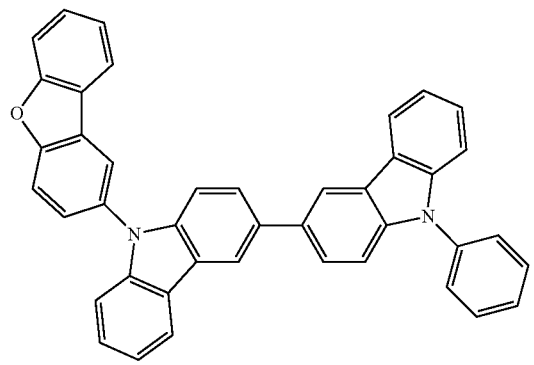
[B-17]
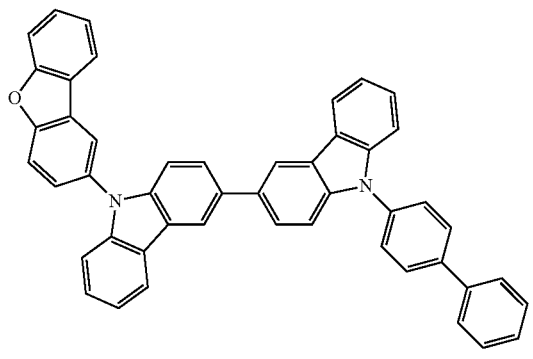
[B-18]
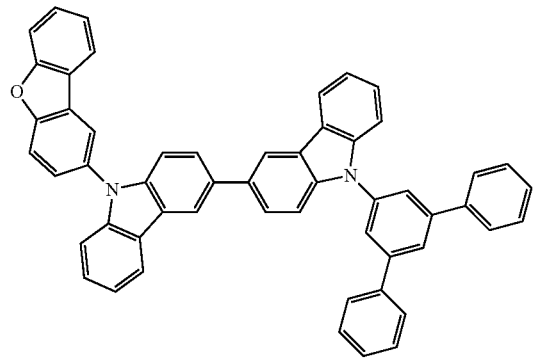
[B-19]
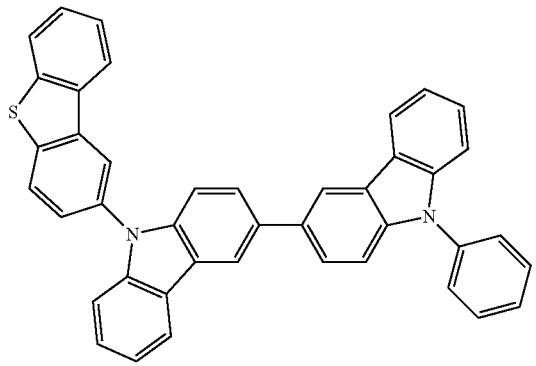

-continued
[B-20]
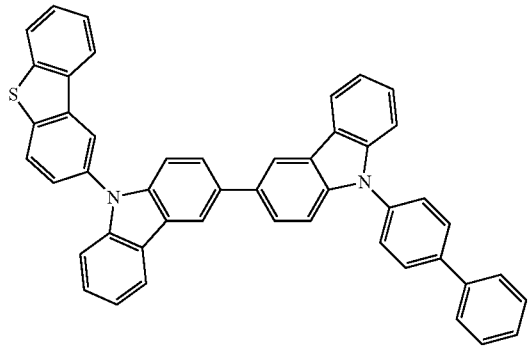
[B-21]
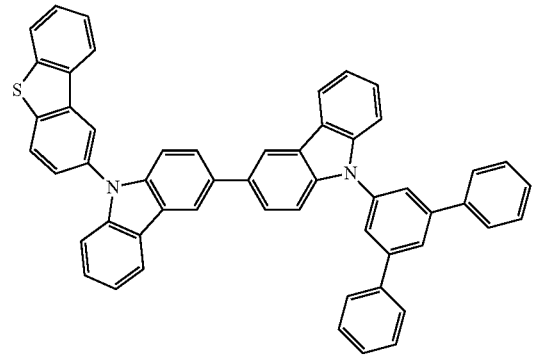
[B-22]
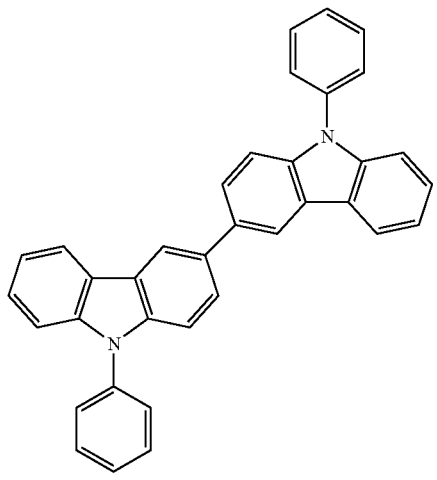
[B-23]
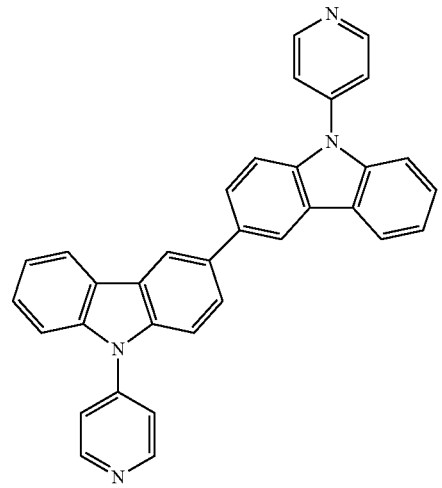
[B-24]
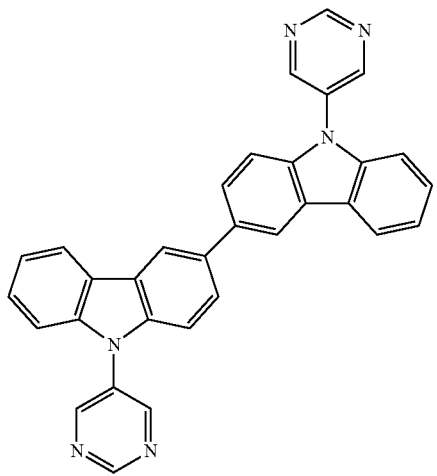
[B-25]
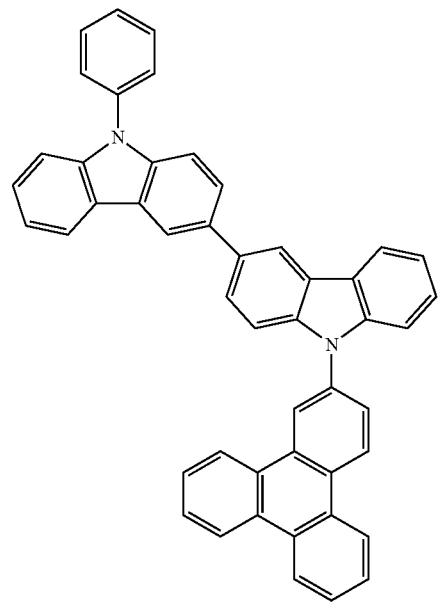

-continued
[B-26]
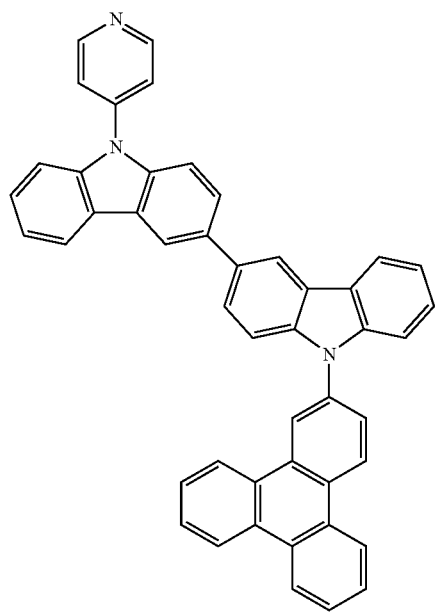
[B-27]
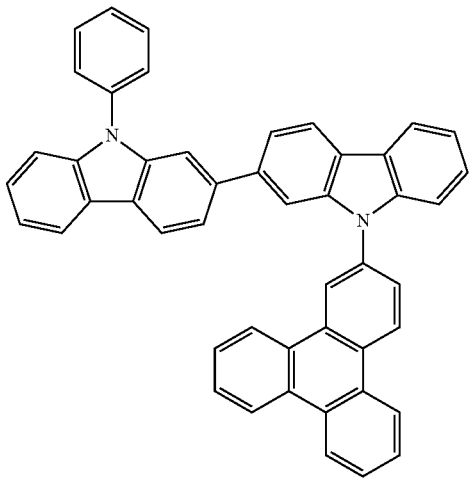
[B-28]
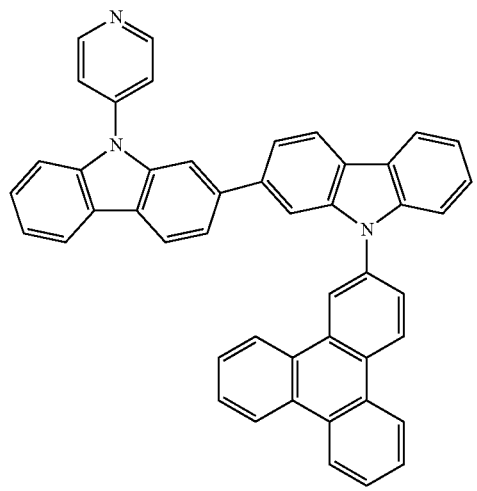
[B-29]
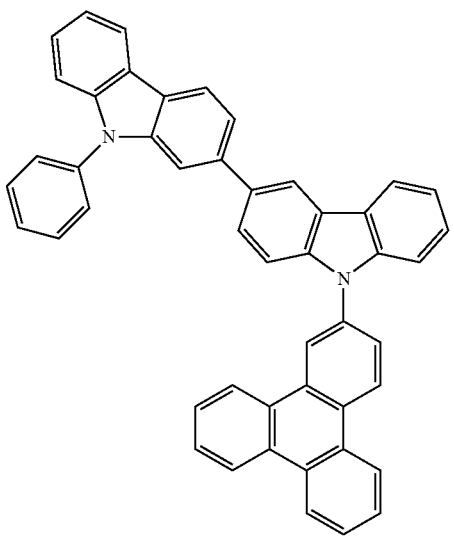

-continued
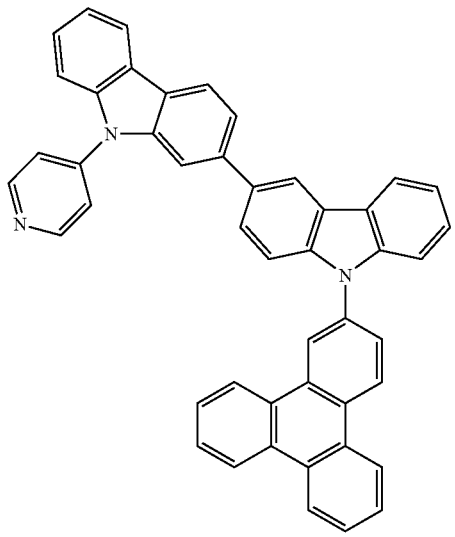
[B-30]
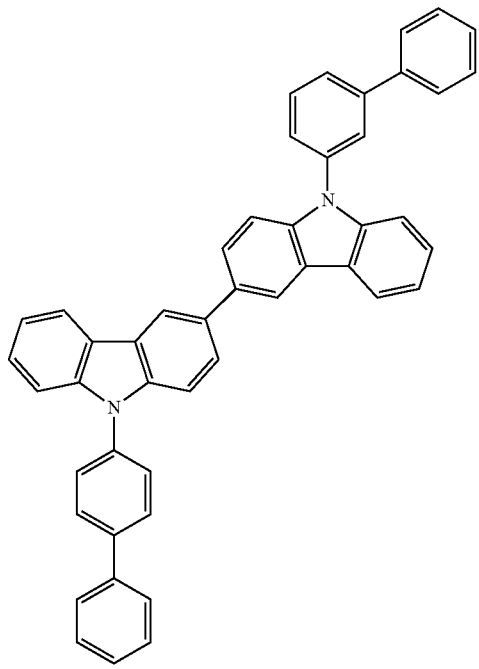
[B-31]
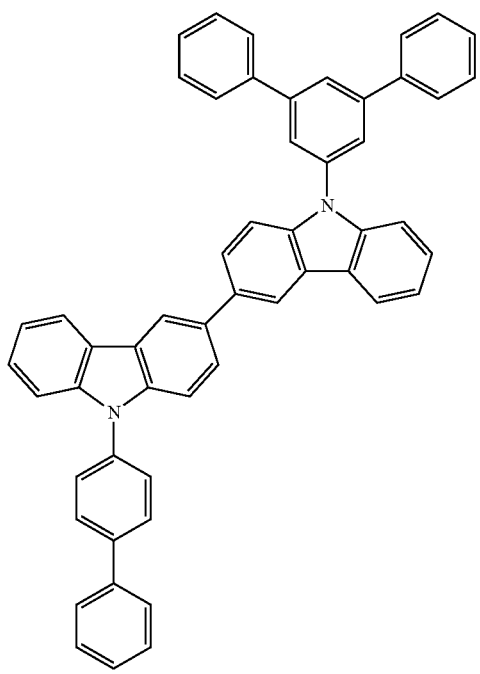
[B-32]
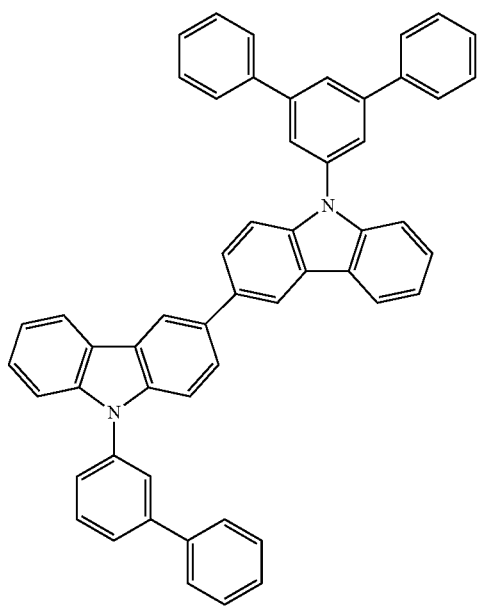
[B-33]

-continued
[B-34]
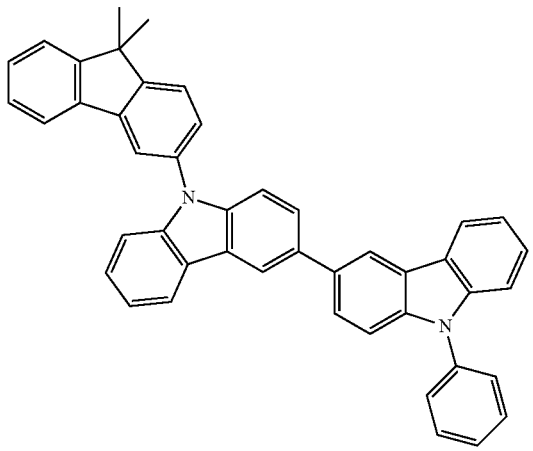
[B-35]
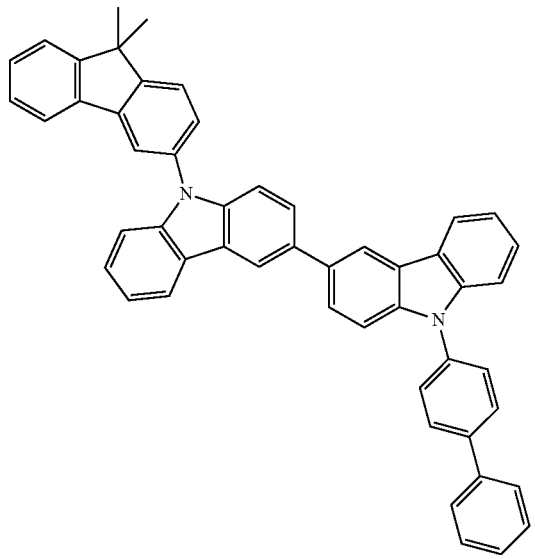
[B-36]
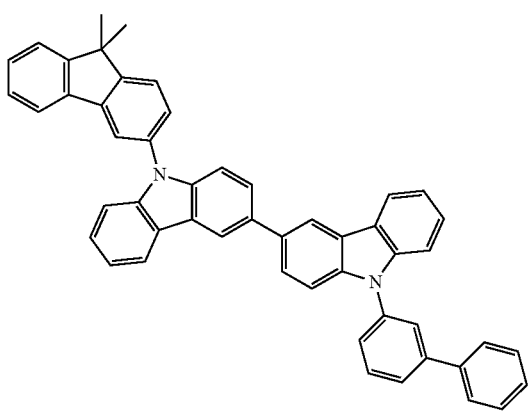
[B-37]
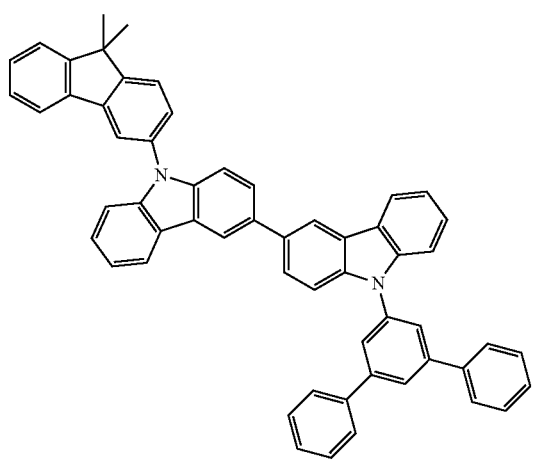
[B-38]
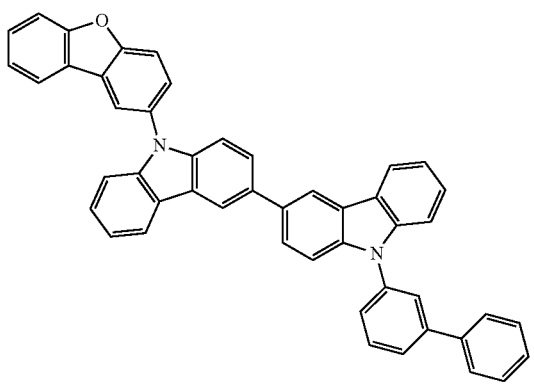
[B-39]
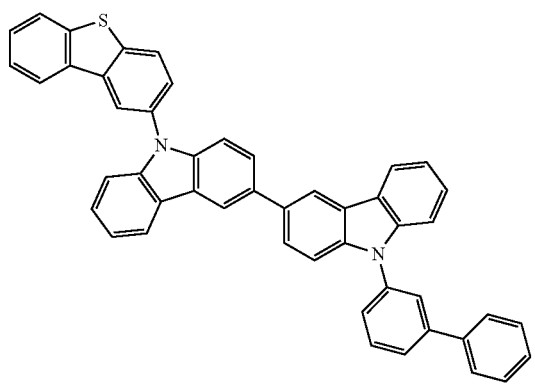

-continued
[B-40]
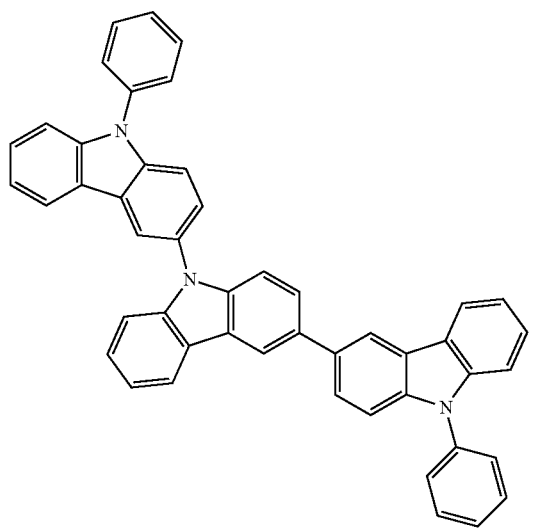
[B-41]
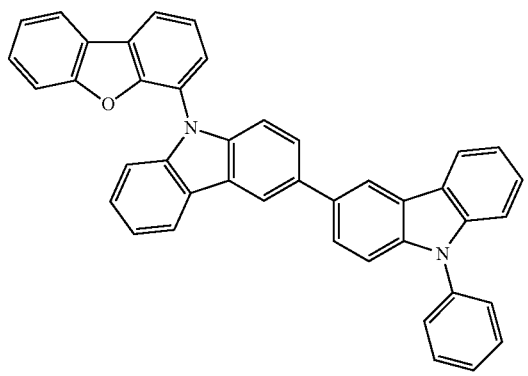
[B-42]
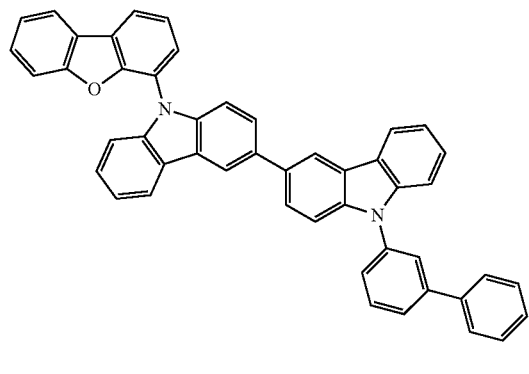
[B-43]
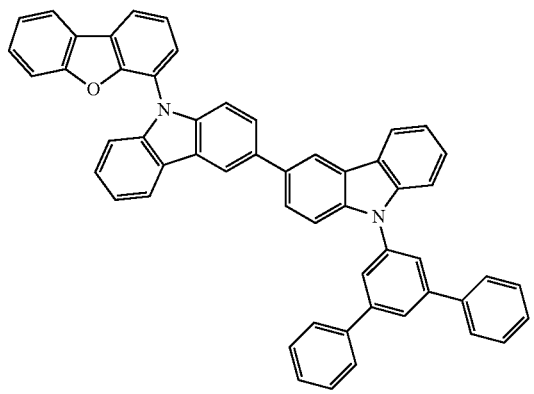
[B-44]
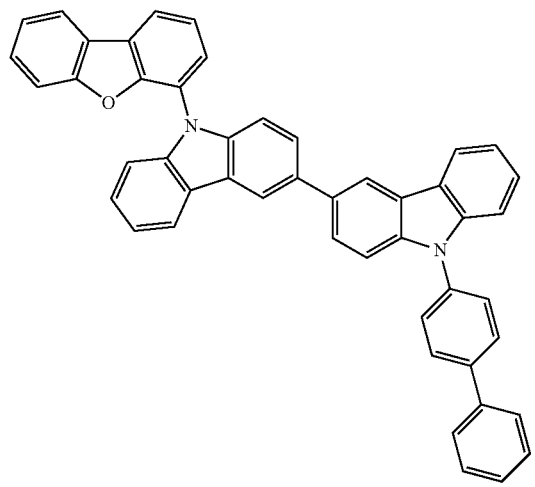
[B-45]
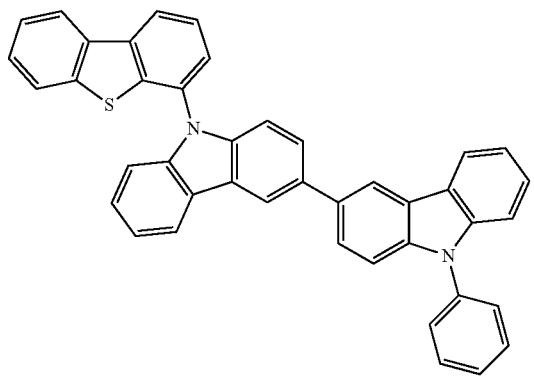

-continued
[B-46]
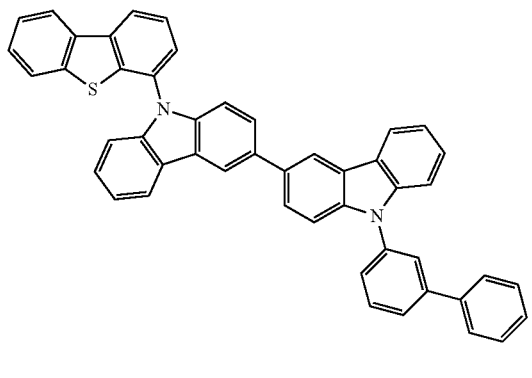
[B-47]
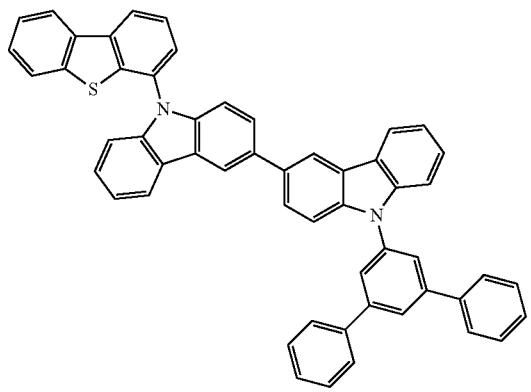
[B-48]
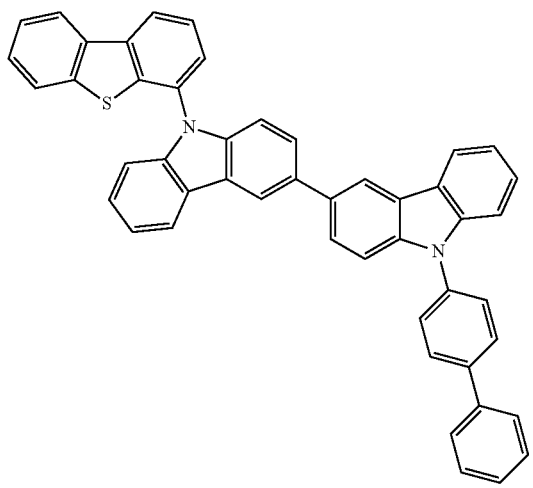
[B-49]
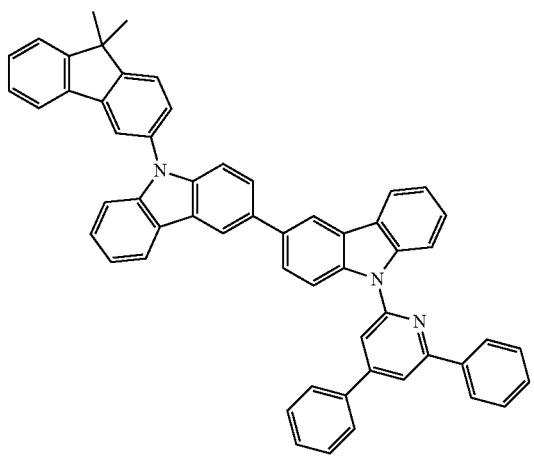
[B-50]
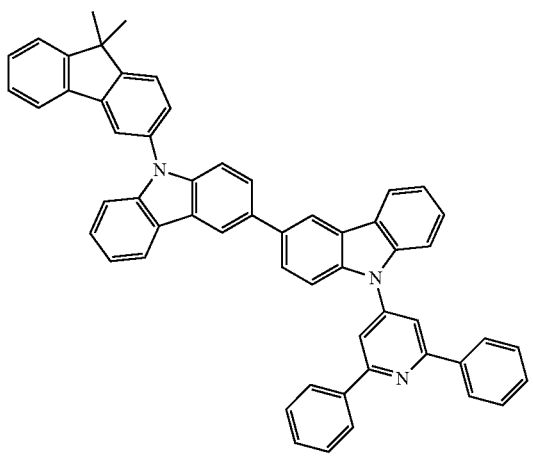
[B-51]
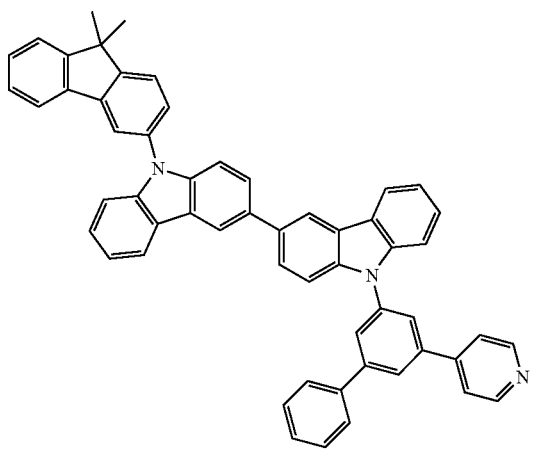

-continued
[B-52]
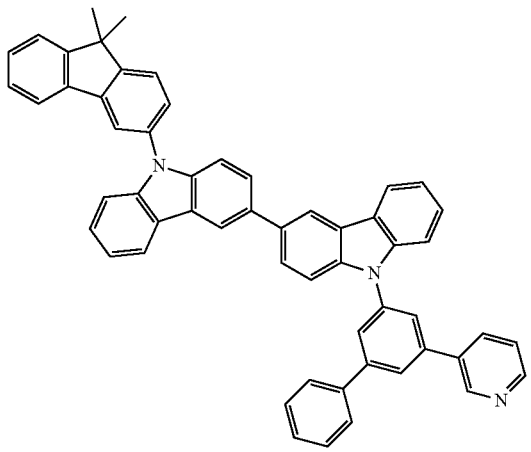
[B-53]
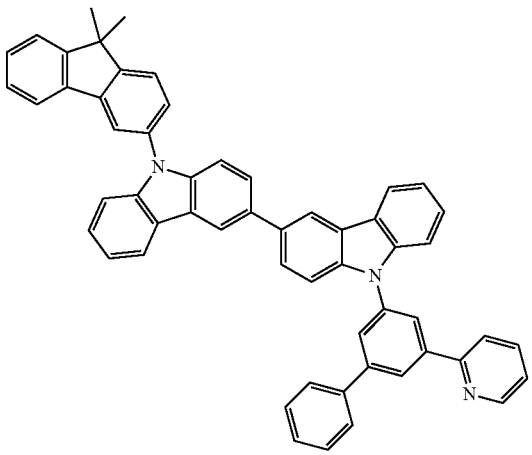
[B-54]
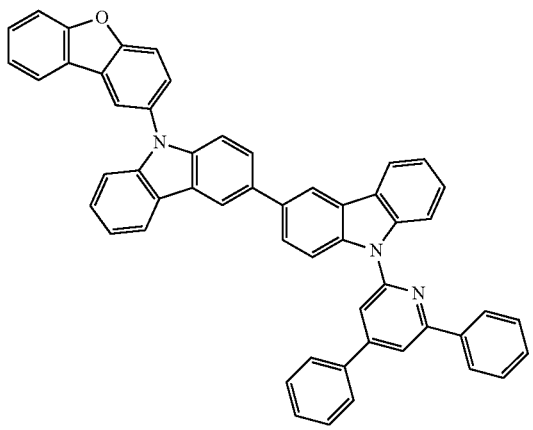
[B-55]
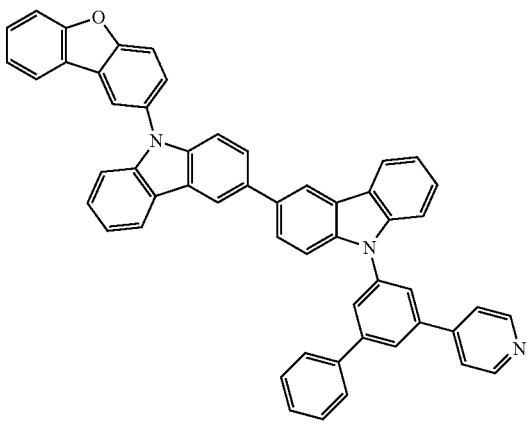
[B-56]
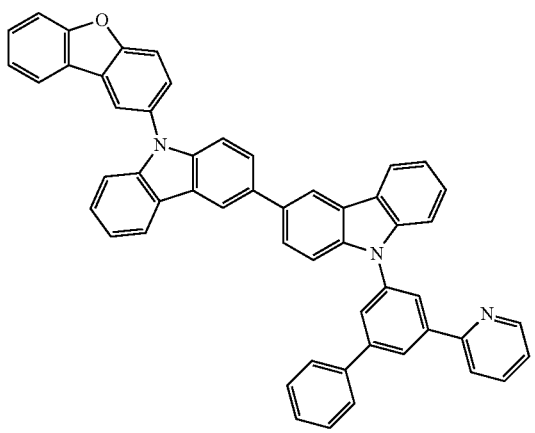
[B-57]
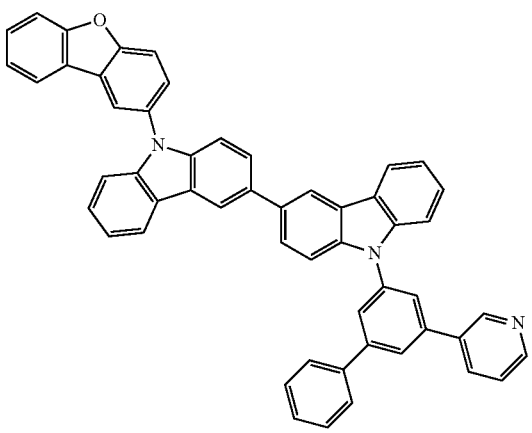

-continued
[B-58]
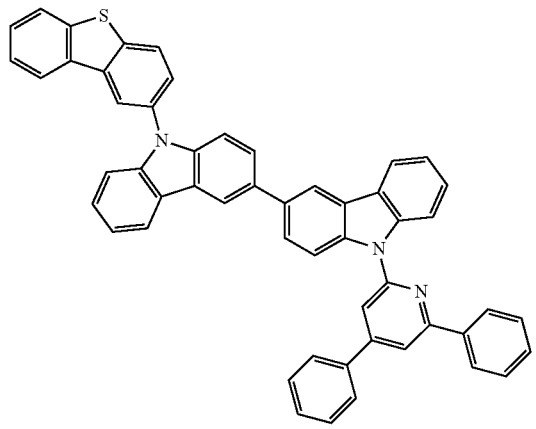
[B-59]
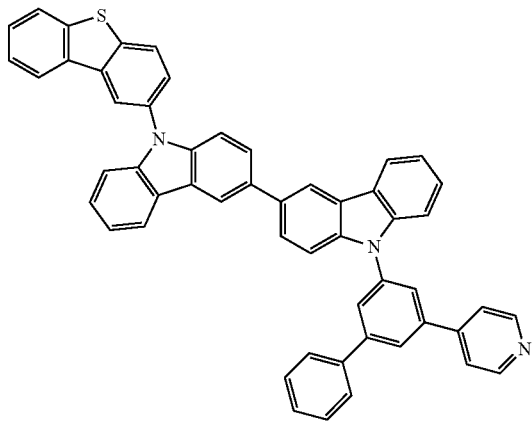
[B-60]
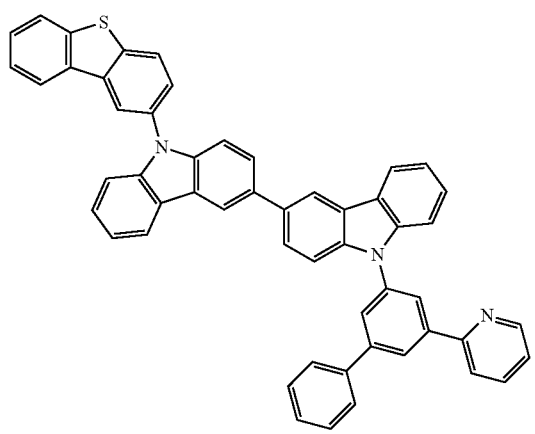
[B-61]
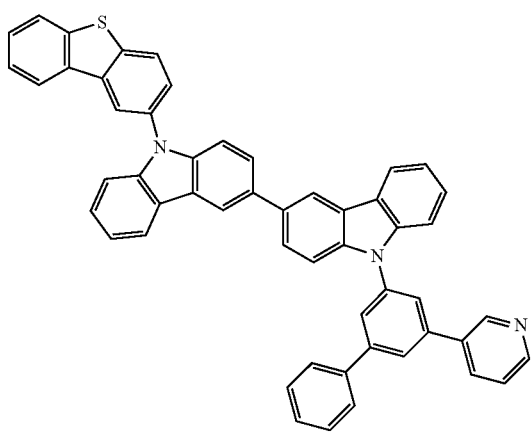
[B-62]
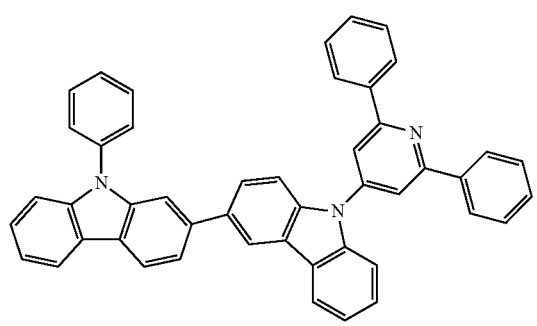
[B-63]
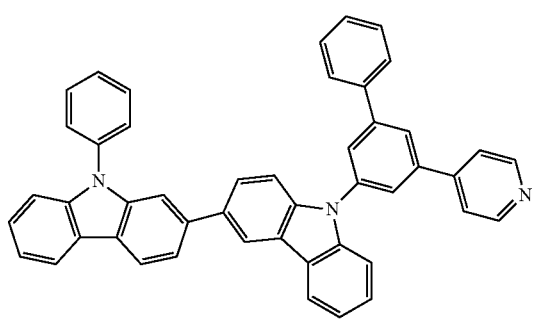
[B-64]
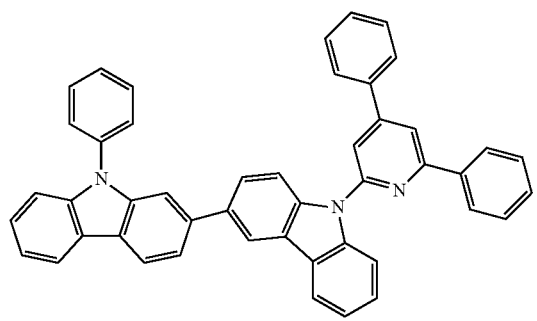
[B-65]
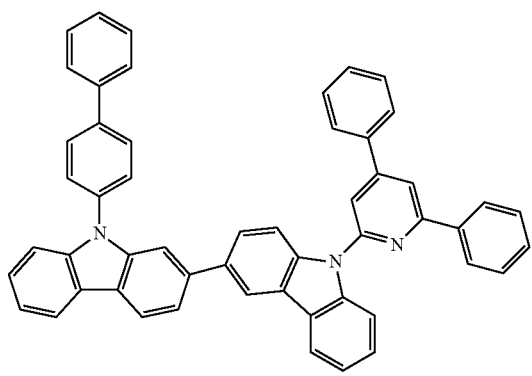

-continued
[B-66]
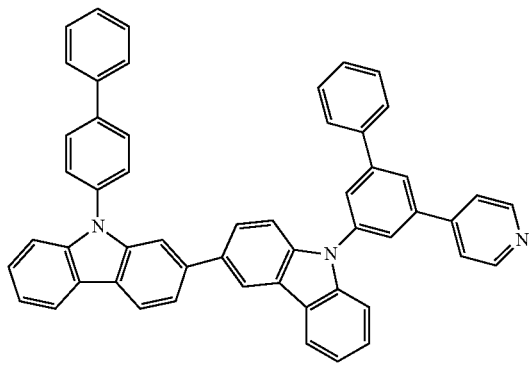
[B-67]
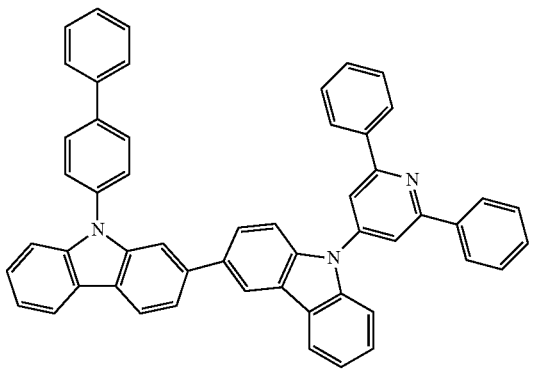
[B-68]
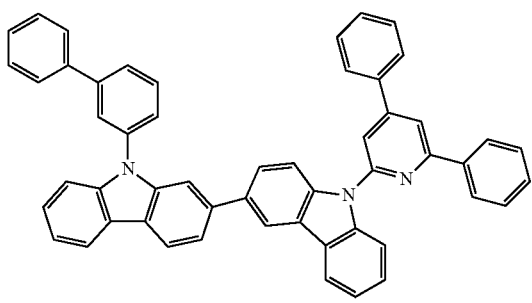
[B-69]
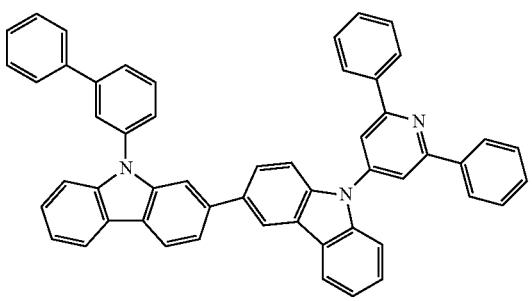
[B-70]
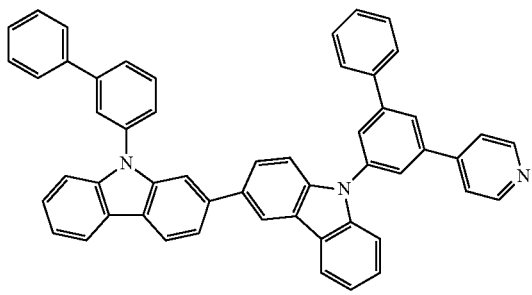
[B-71]
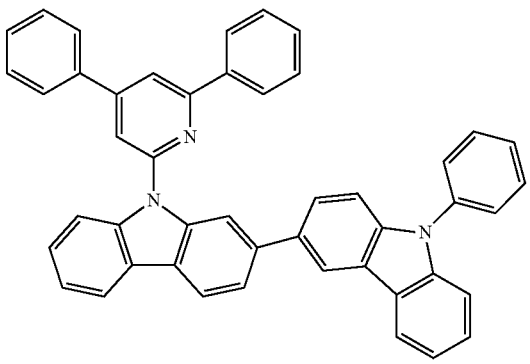
[B-72]
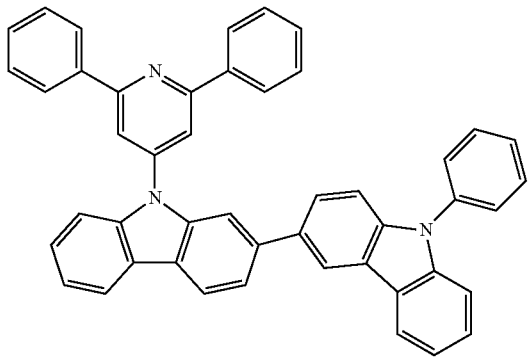
[B-73]
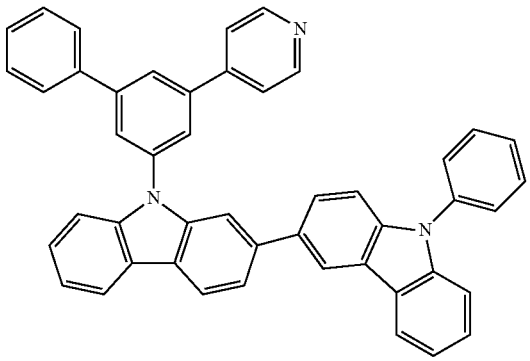

-continued
[B-74]
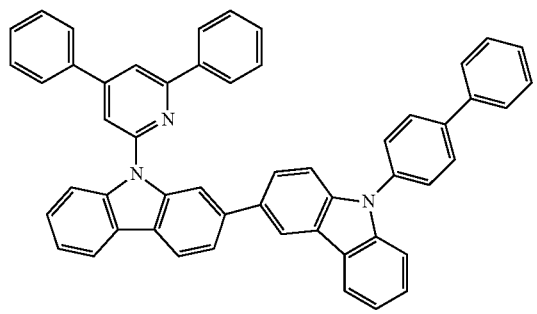
[B-75]
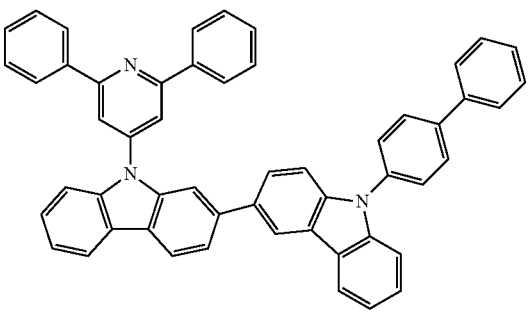
[B-76]
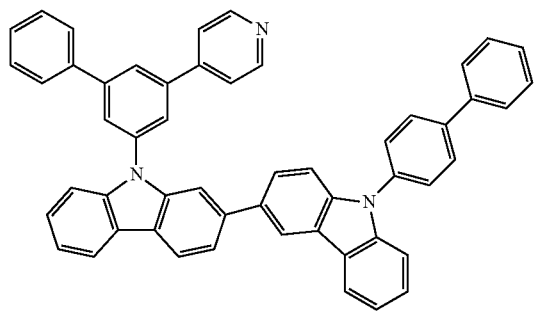
[B-77]
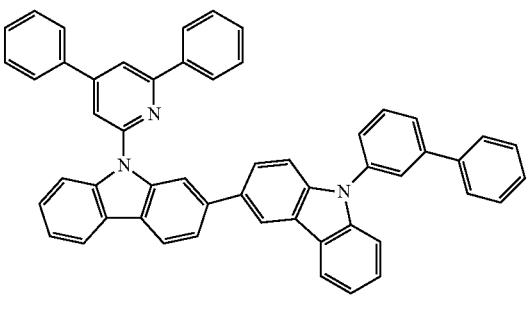
[B-78]
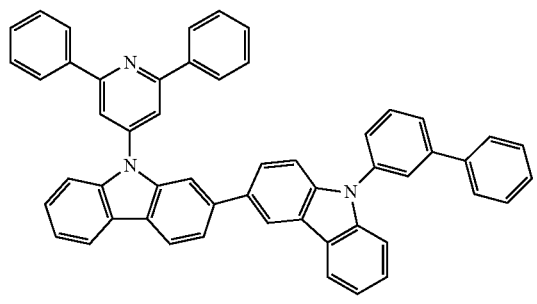
[B-79]
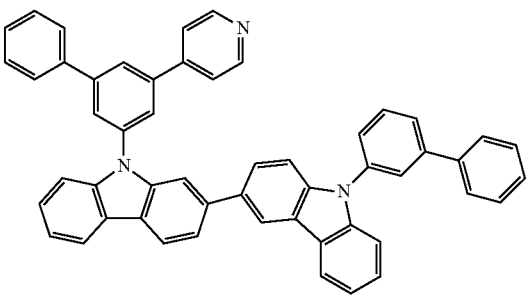
[B-80]
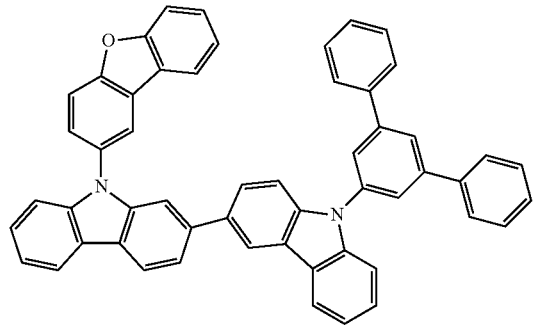
[B-81]
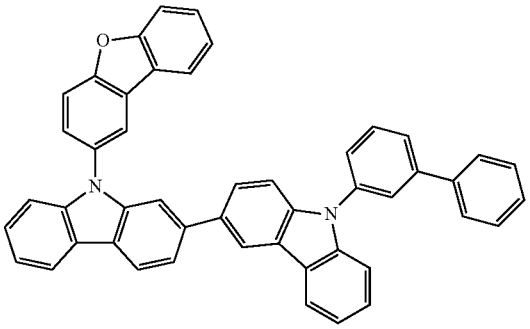

-continued
[B-82]
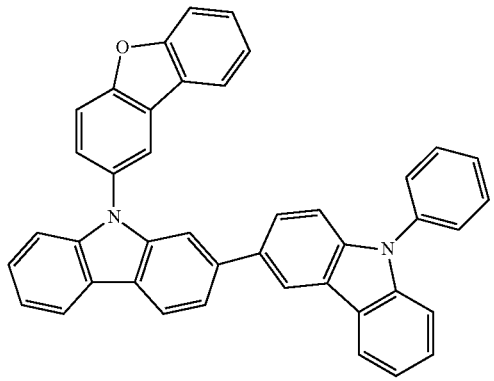
[B-83]
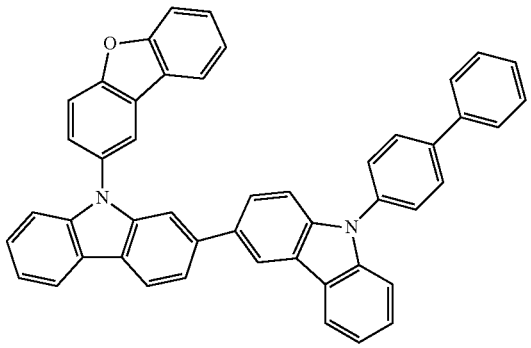
[B-84]
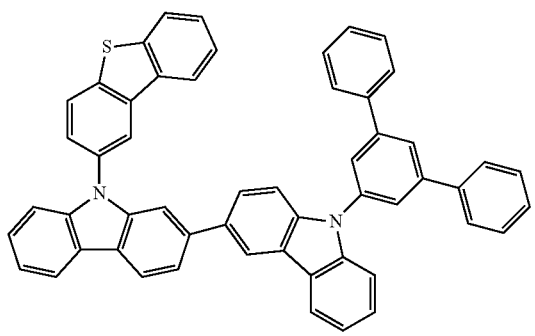
[B-85]
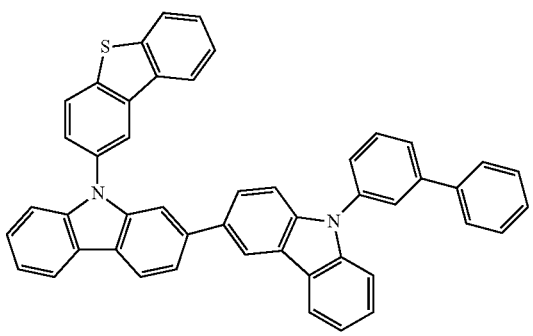
[B-86]
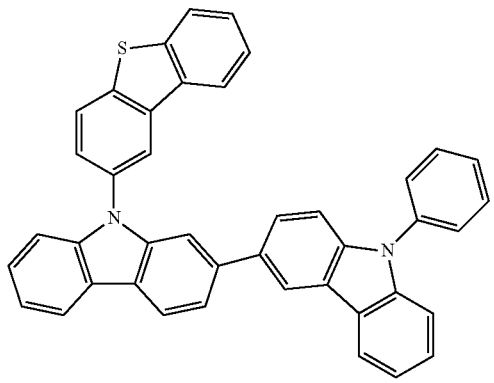
[B-87]
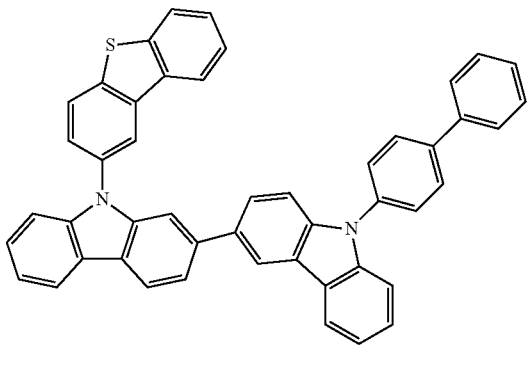
[B-88]
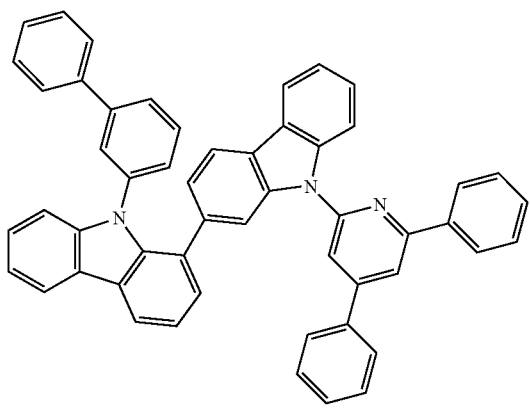
[B-89]
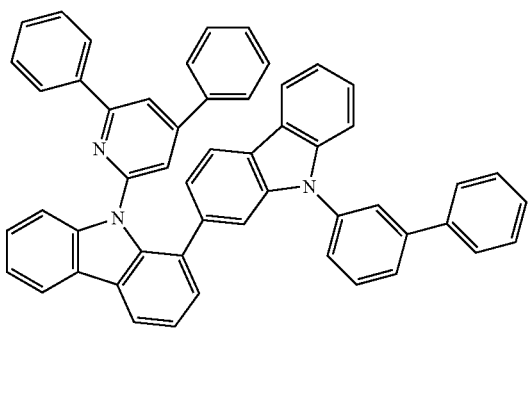

-continued
[B-90]
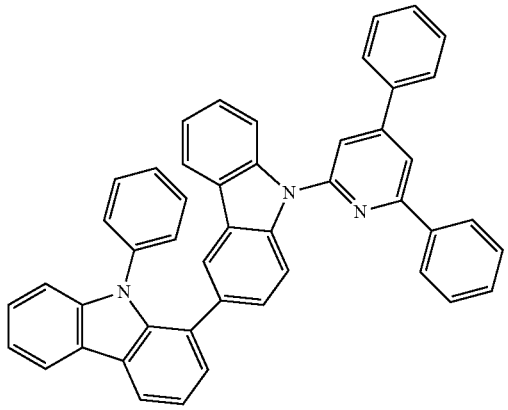
[B-91]
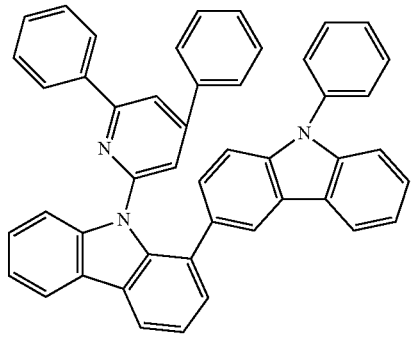
[B-92]
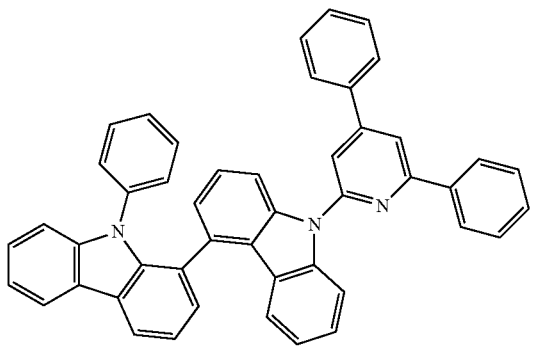
[B-93]
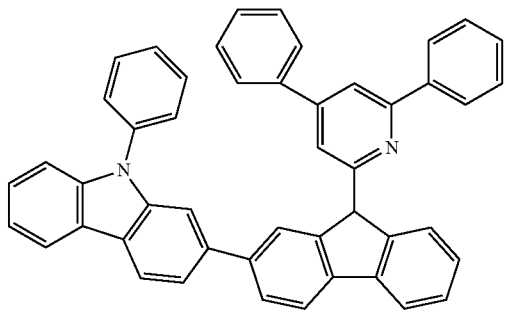
[B-94]
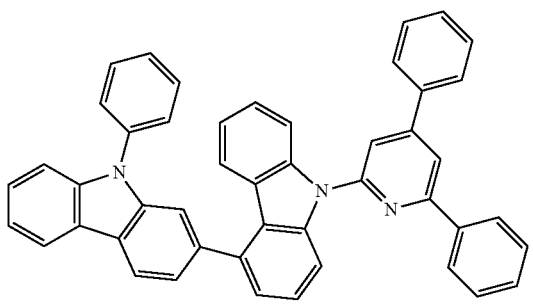
[B-95]
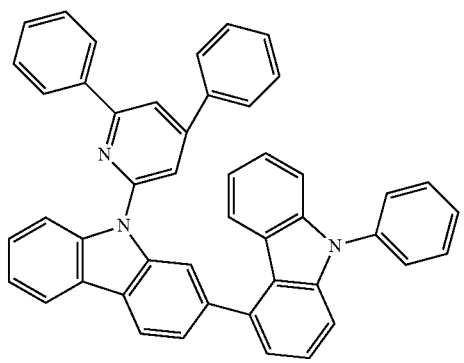
[B-96]
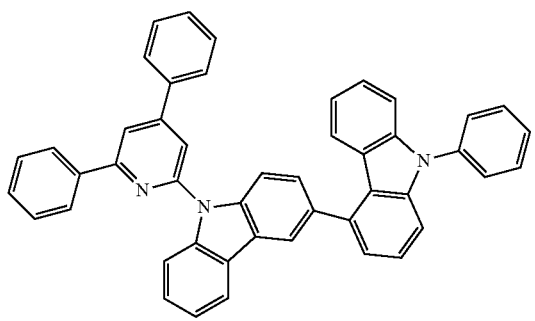
[B-97]
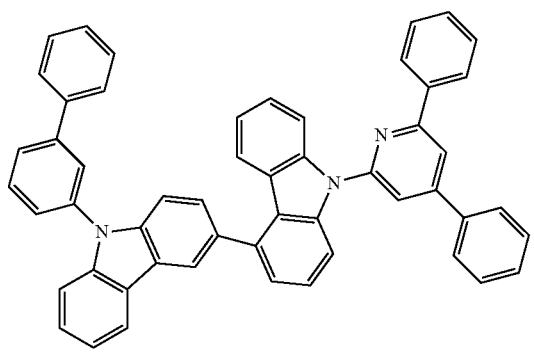

-continued
[B-98]
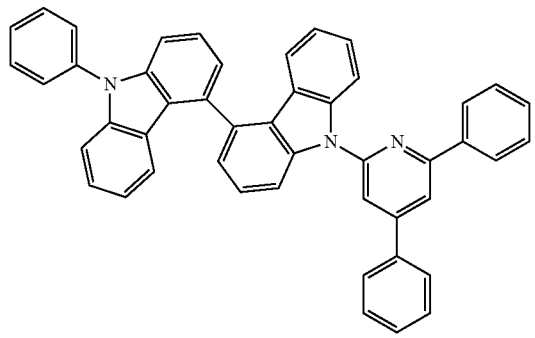
[B-99]
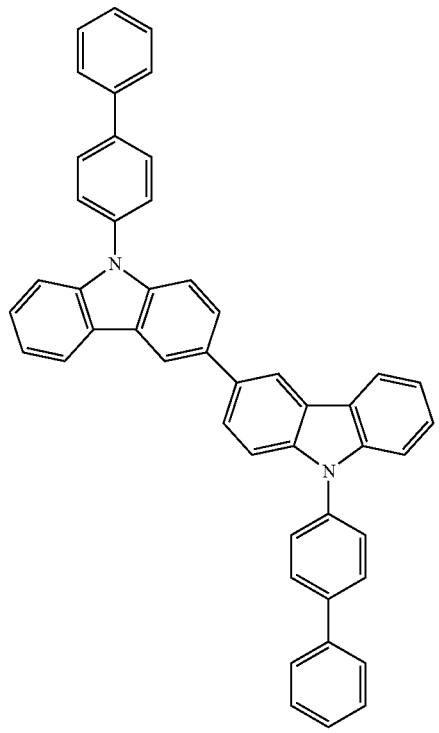
[B-100]
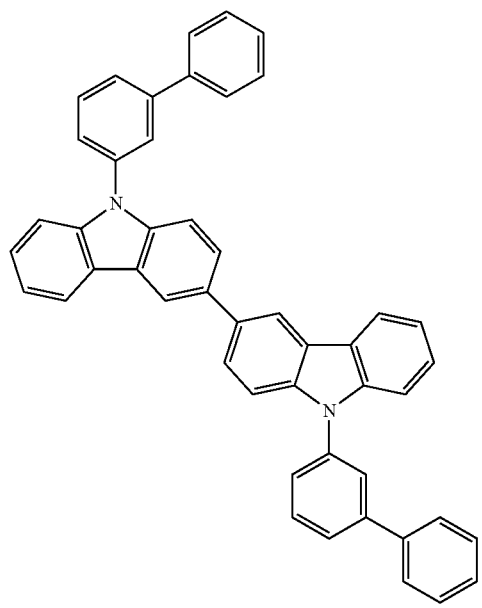
[B-101]
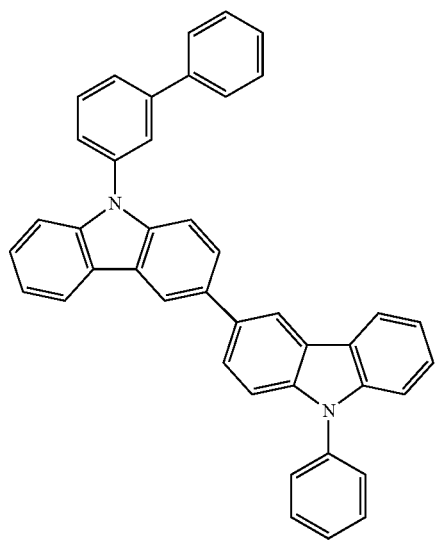

-continued
[B-102]
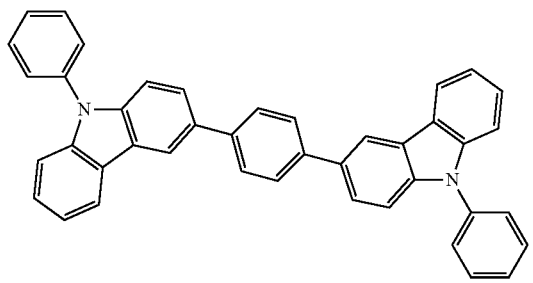
[B-103]
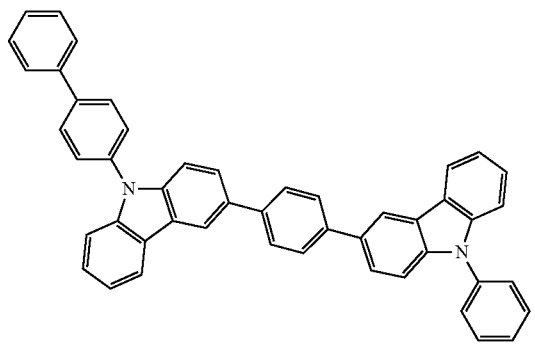
[B-104]
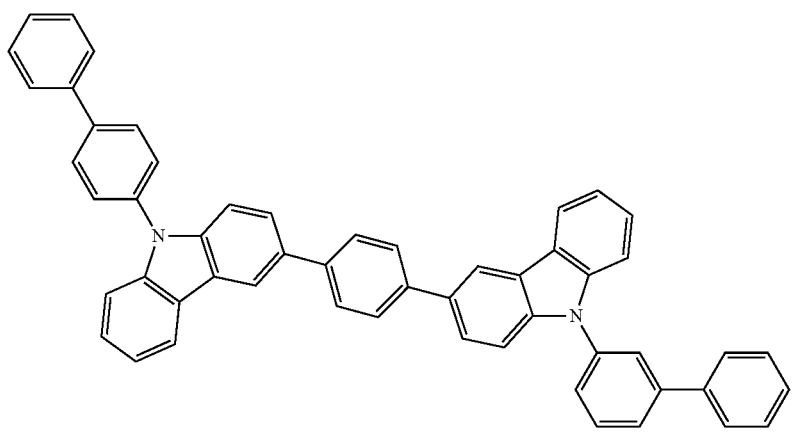
[B-105]
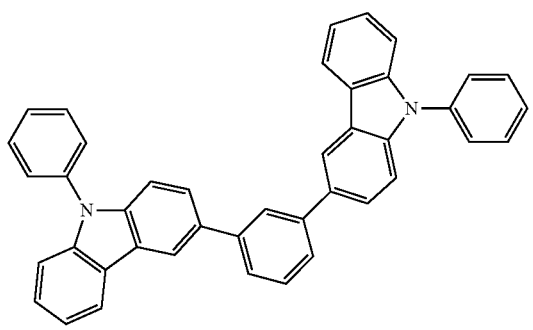
[B-106]
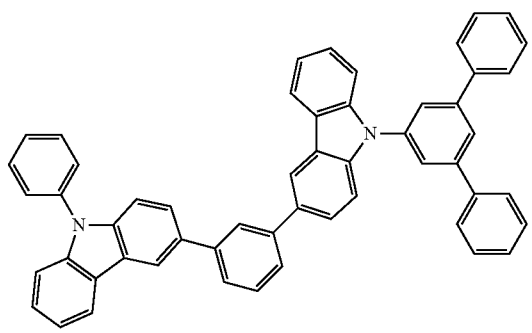
[B-107]
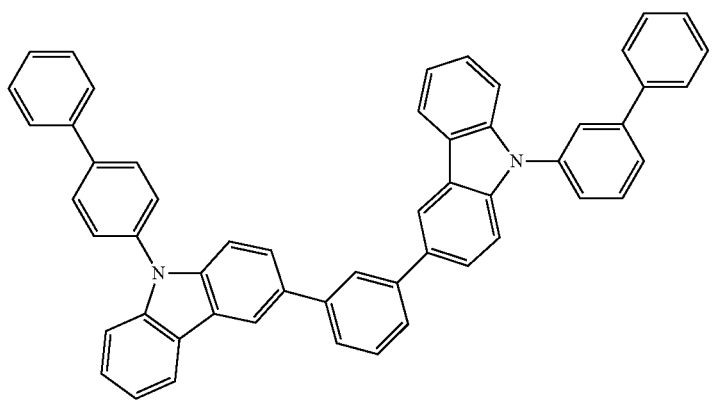

-continued
[B-108]
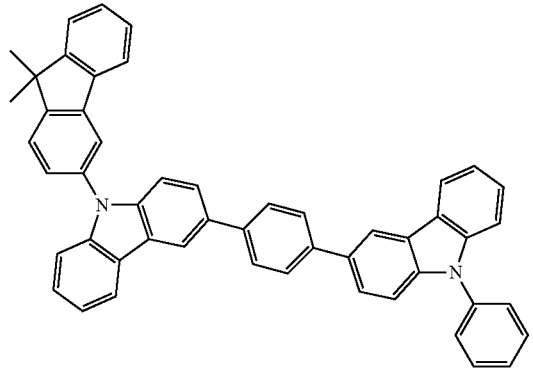
[B-109]
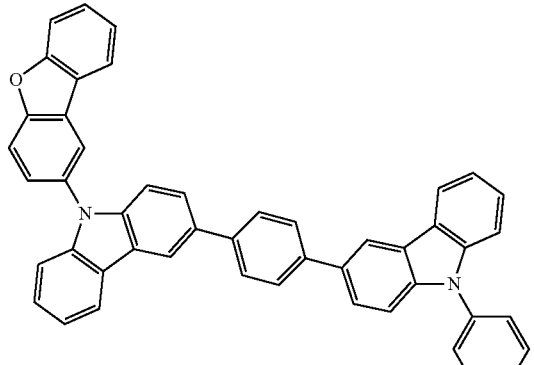
[B-110]
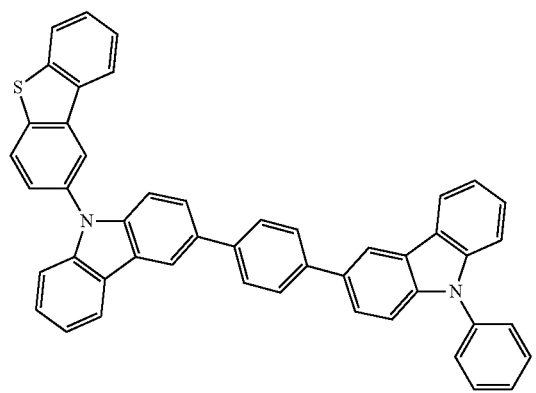
[B-111]
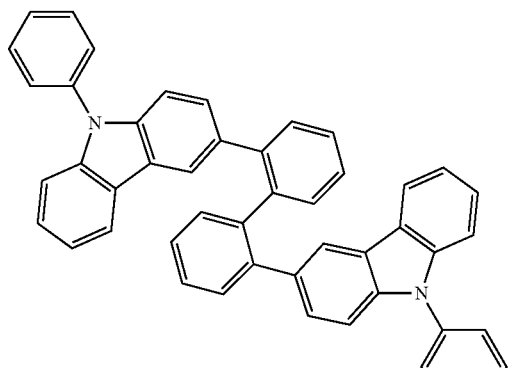
[B-112]
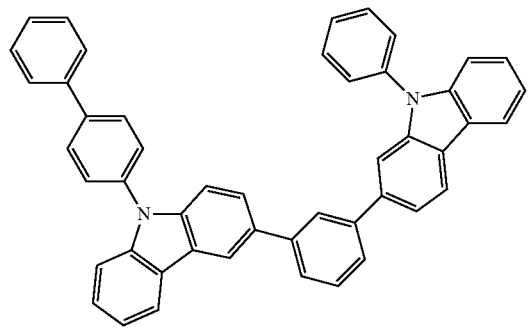
[B-113]
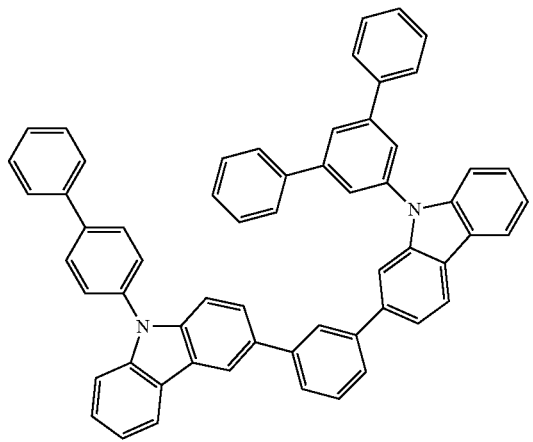
[B-114]
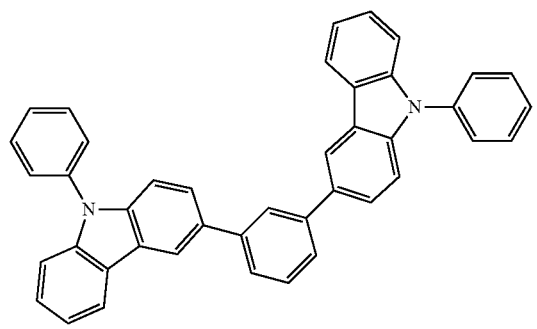
[B-115]
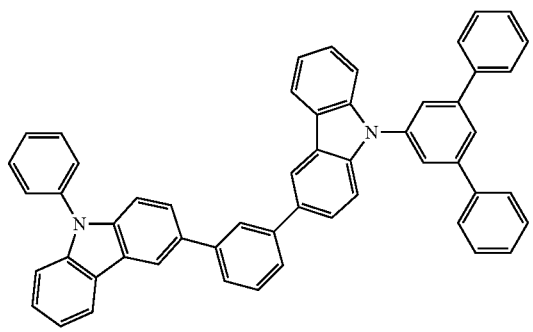

[B-116]
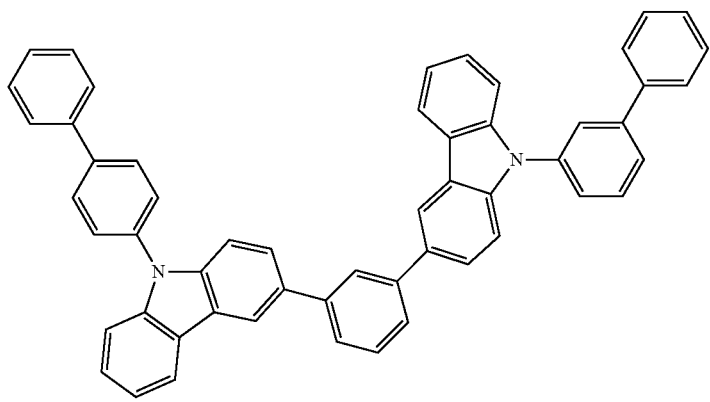
[B-117]
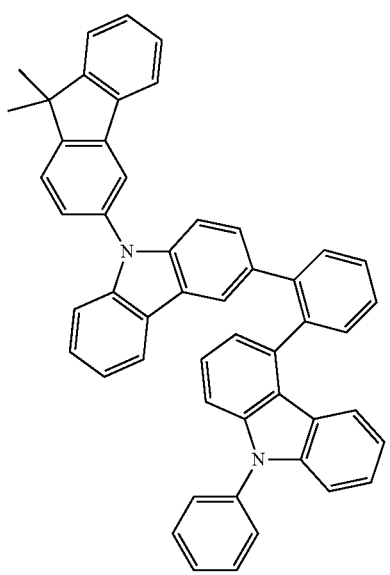
[B-118]
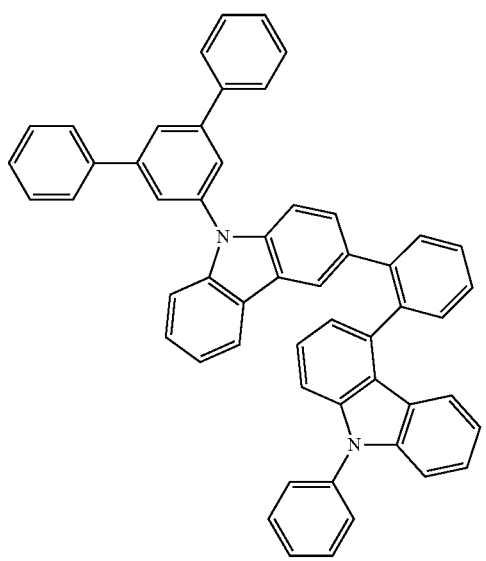
[B-119]
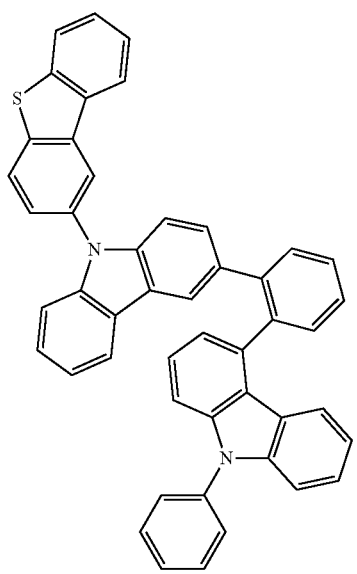
[B-120]
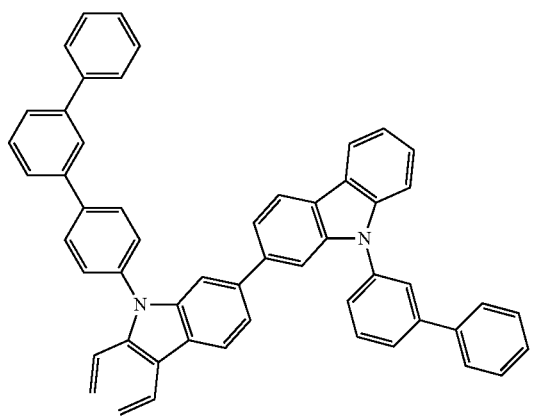

[B-121]
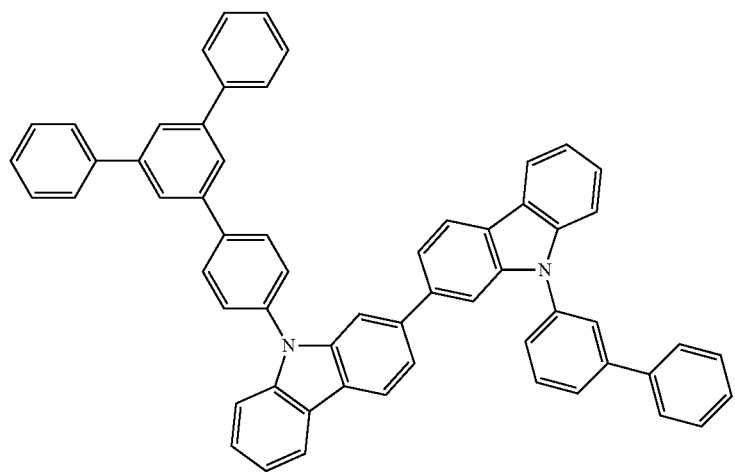
[B-122]
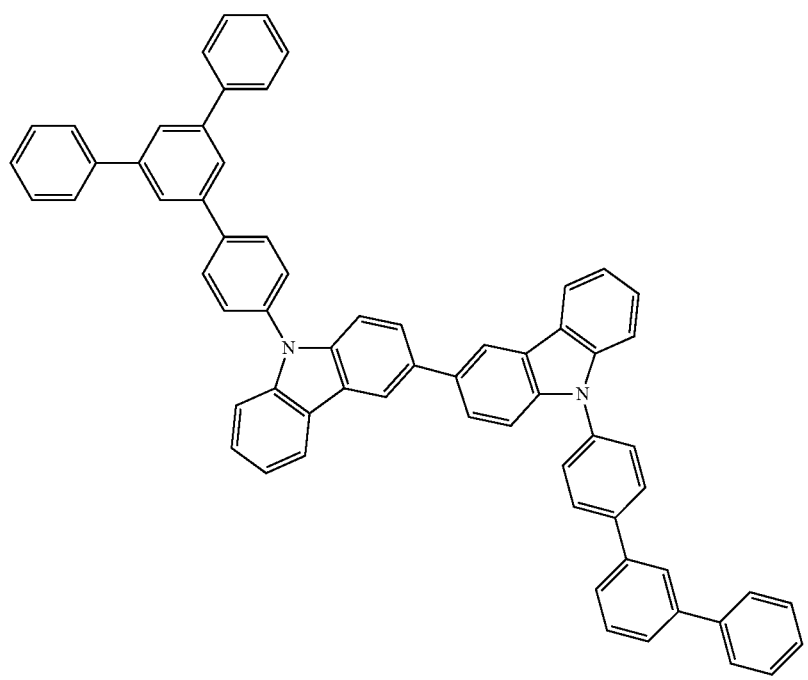

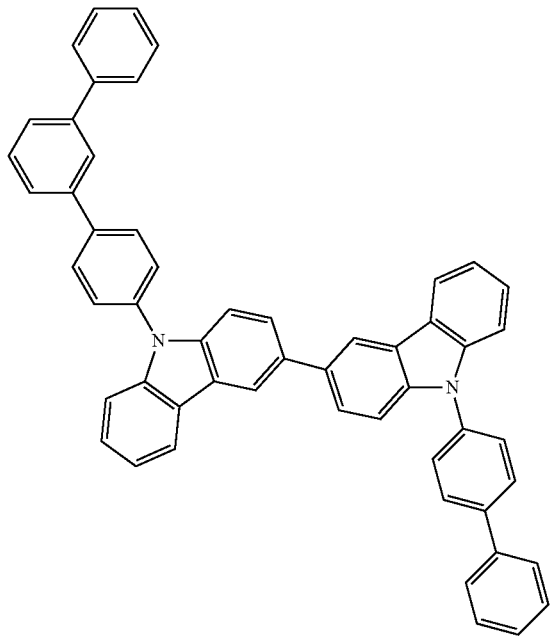
[B-123]
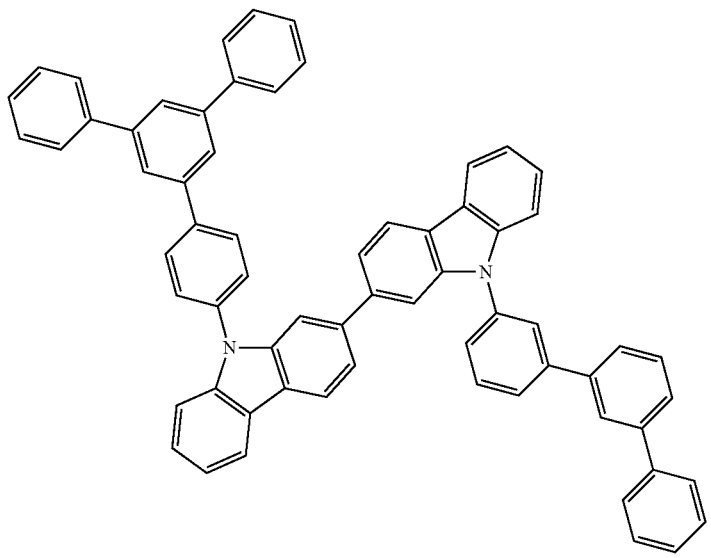
[B-124]

-continued
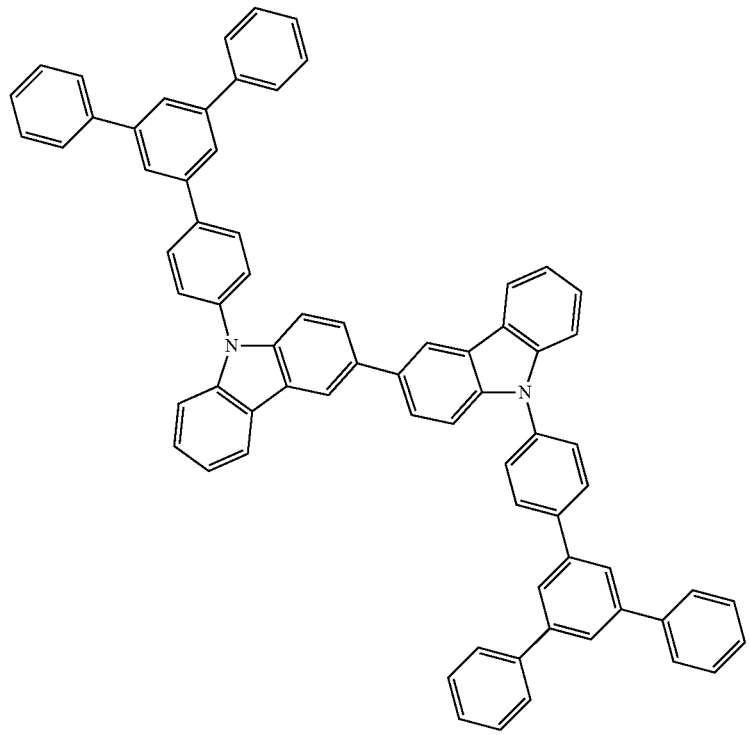
[B-125]
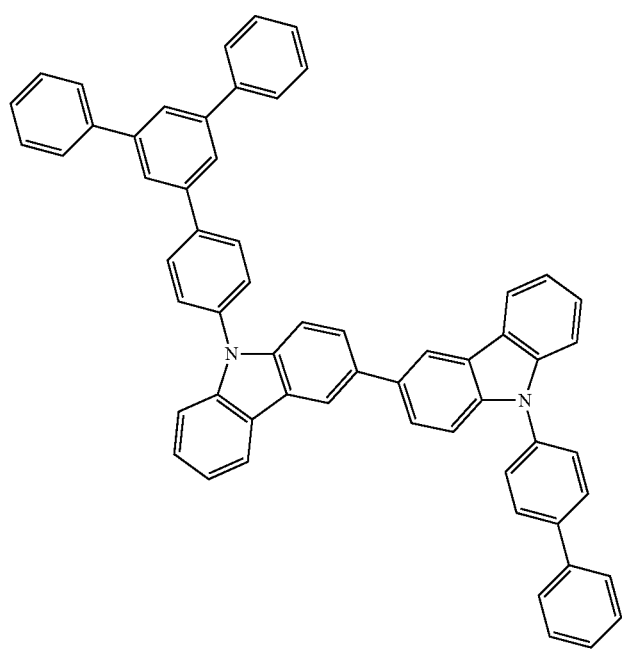
[B-126]

-continued
[B-127]
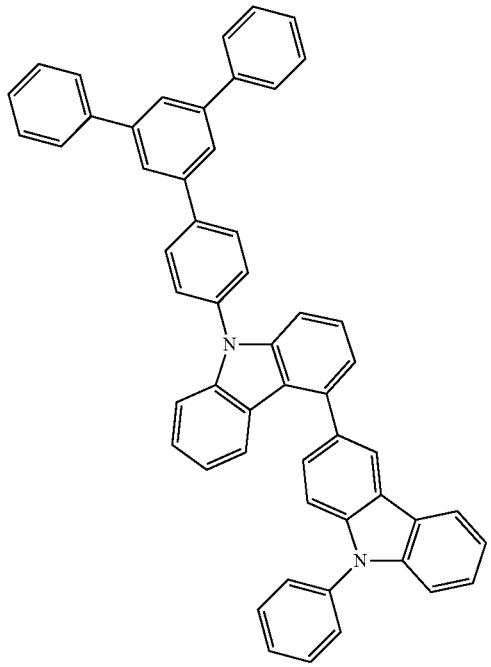
[B-128]
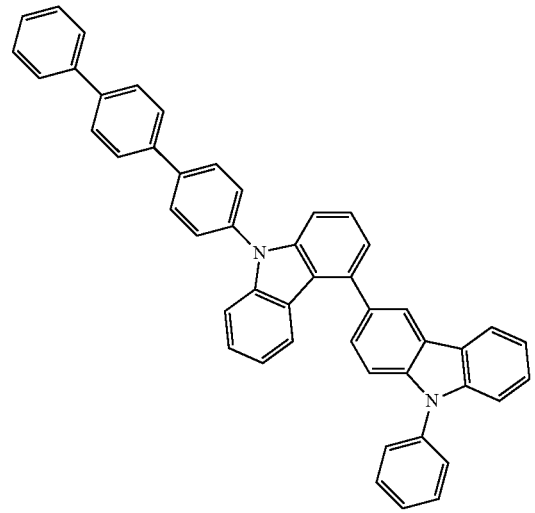
[B-129]
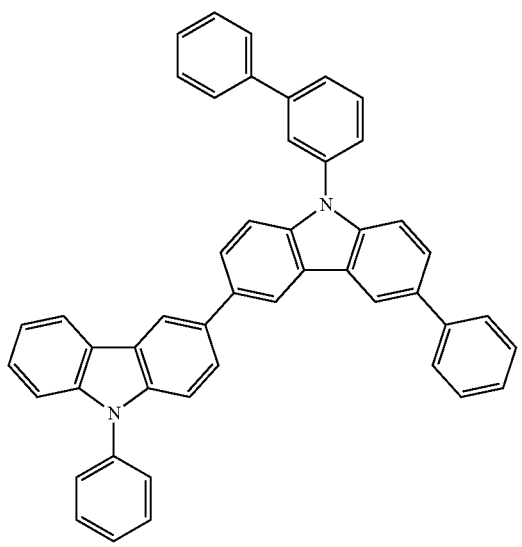
[B-130]
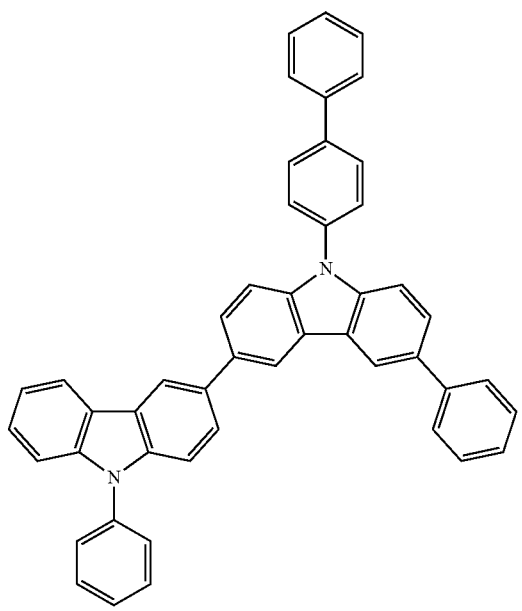

-continued
[B-131]
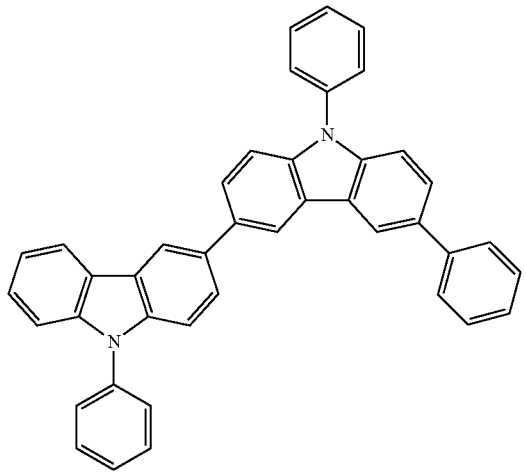
[B-132]
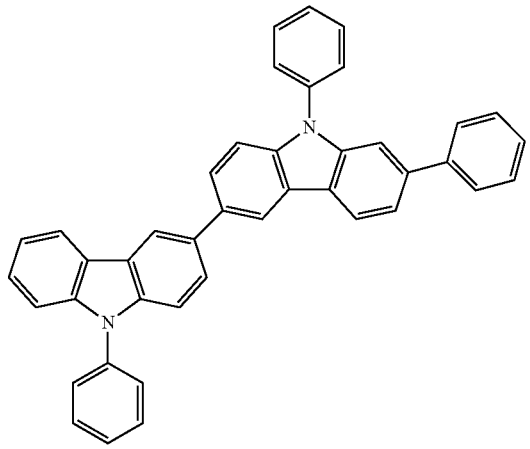
[B-133]
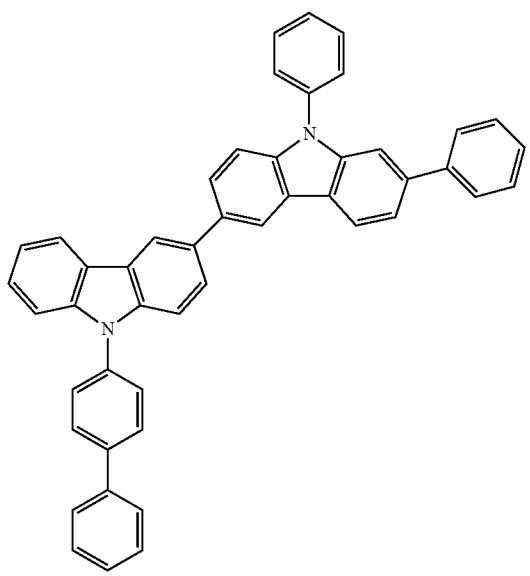
[B-134]
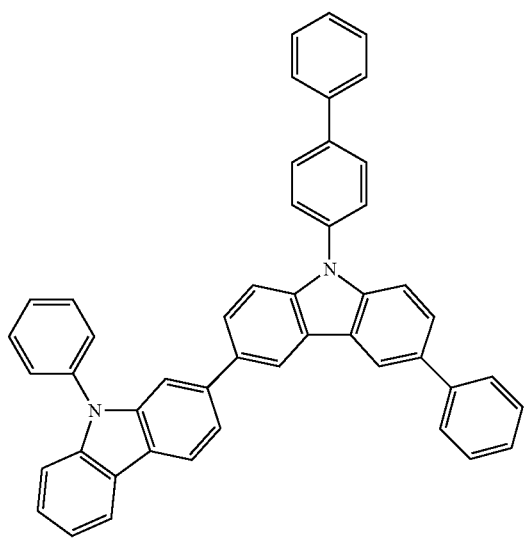

-continued
[B-135]
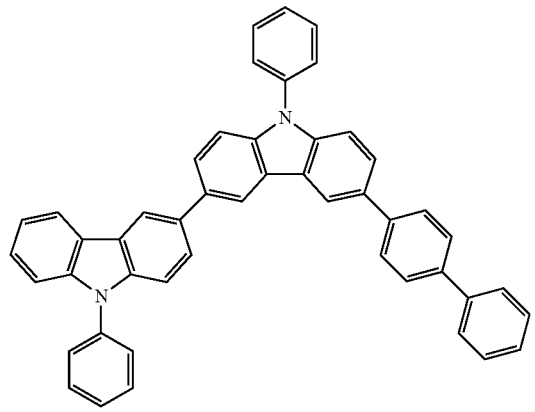
[B-136]
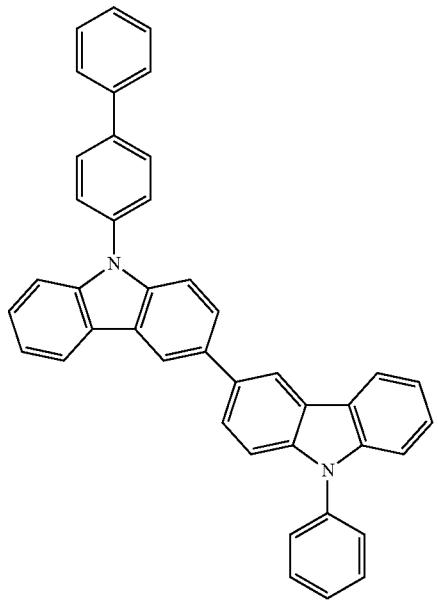
[B-137]
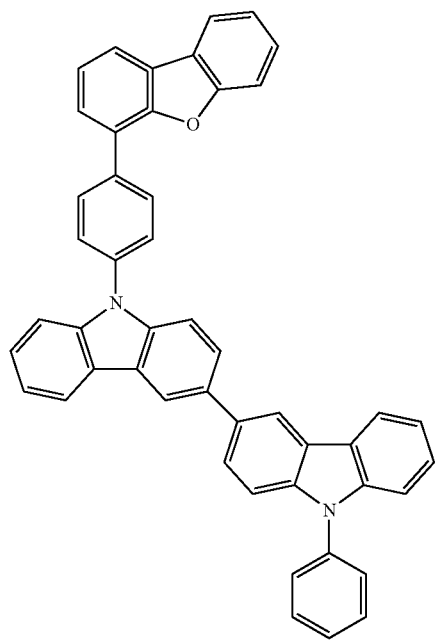
[B-138]
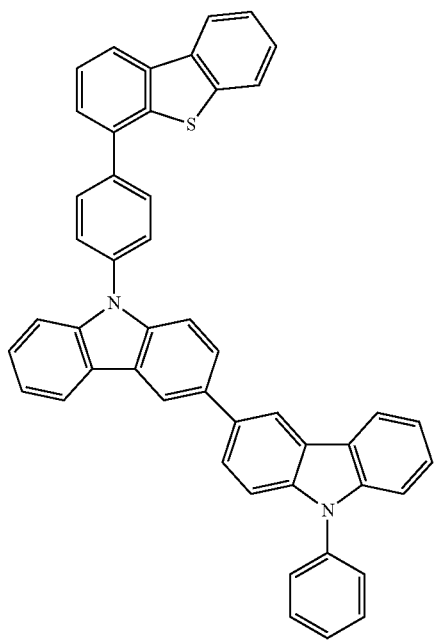
[C-1]
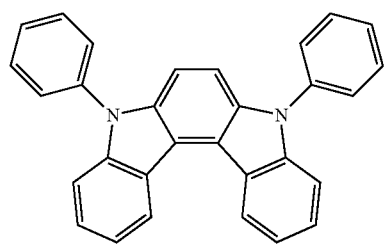
[C-2]
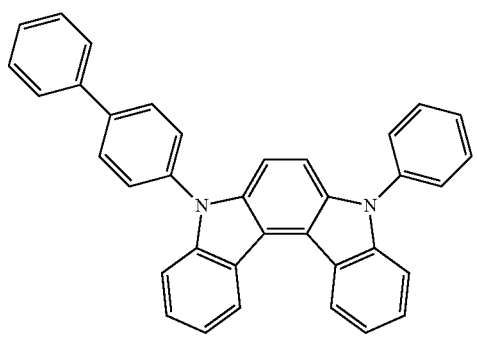

-continued
[C-3]
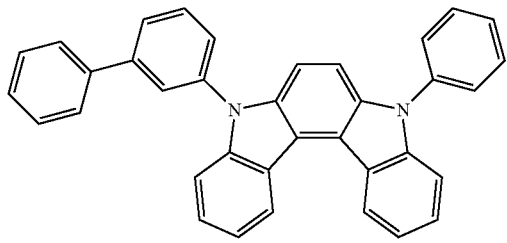
[C-4]
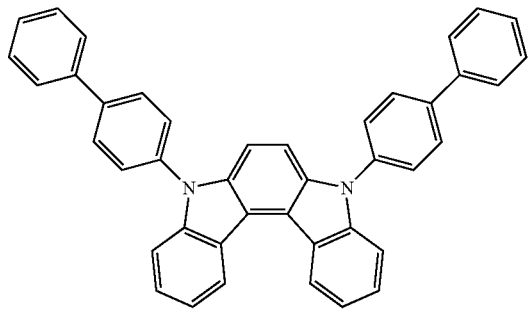
[C-5]
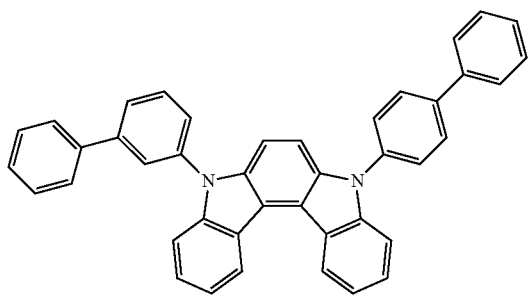
[C-6]
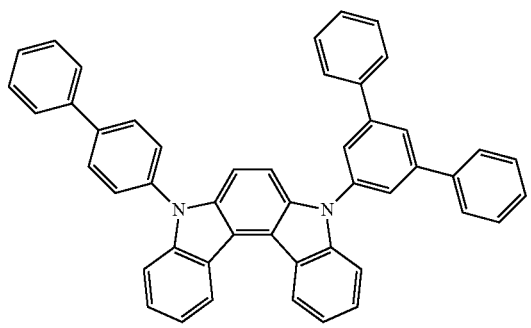
[C-7]
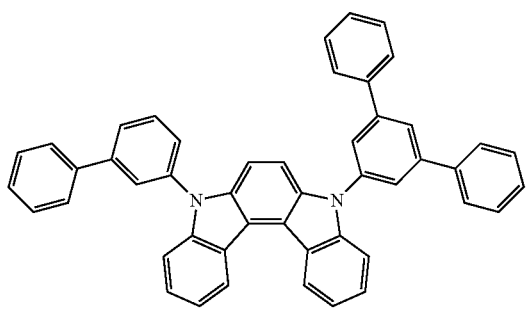
[C-8]
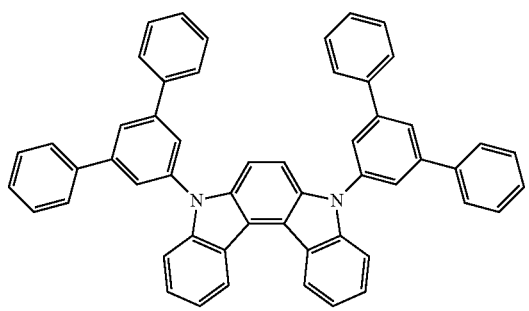
[C-9]
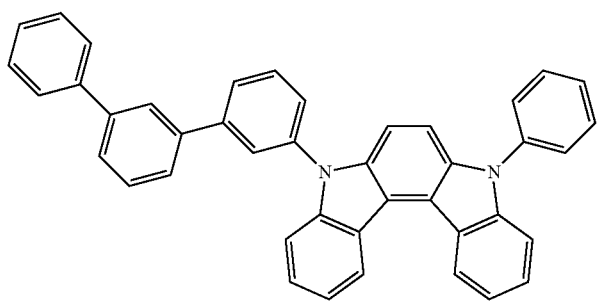
[C-10]
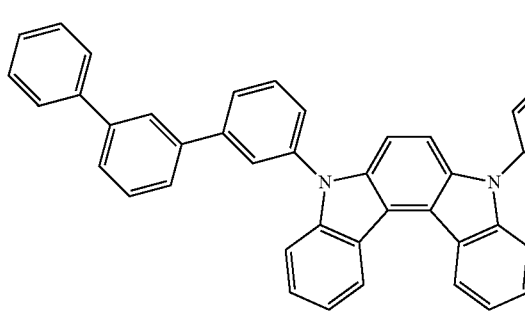

-continued
[C-11]
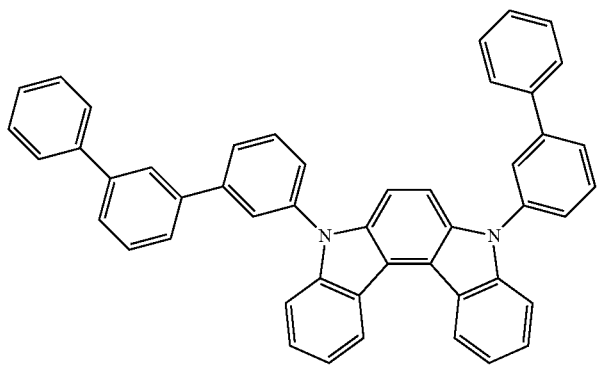
[B-12]
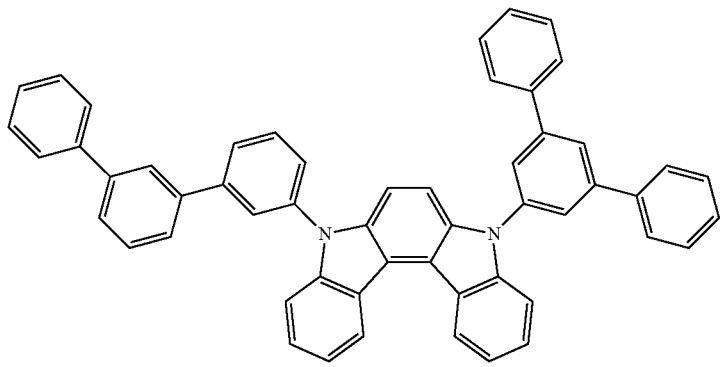
[B-13]
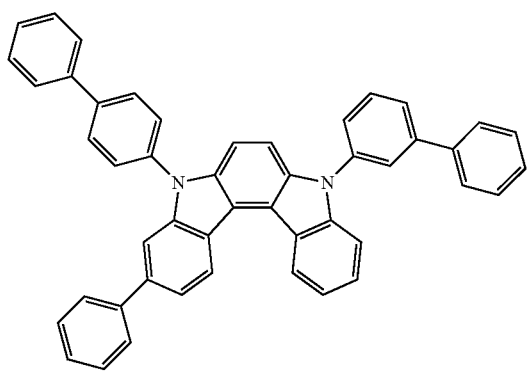
[B-14]
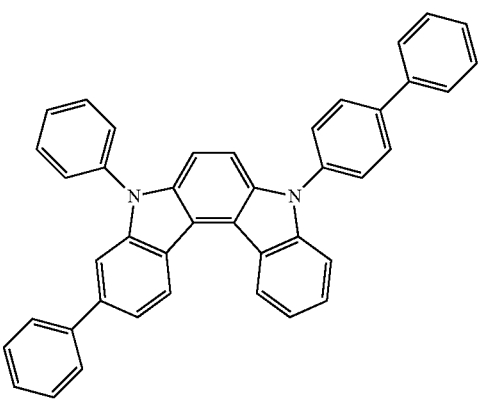
[B-15]
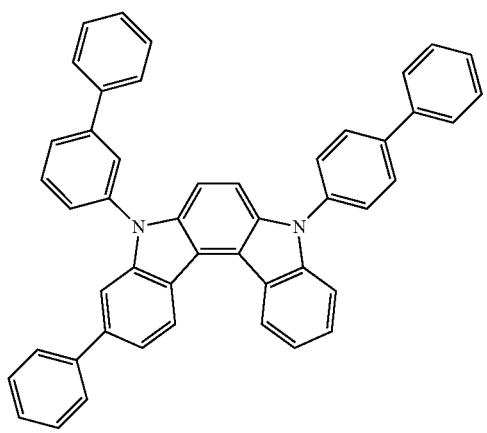
[B-16]
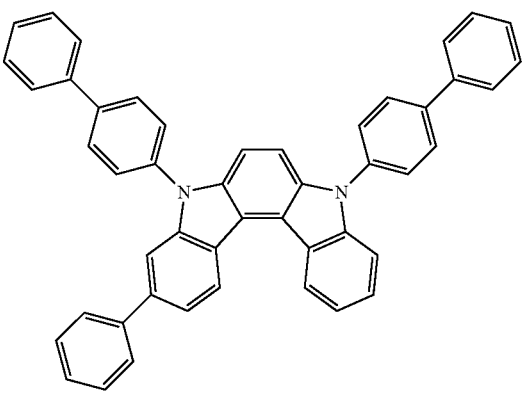

-continued
[C-17]
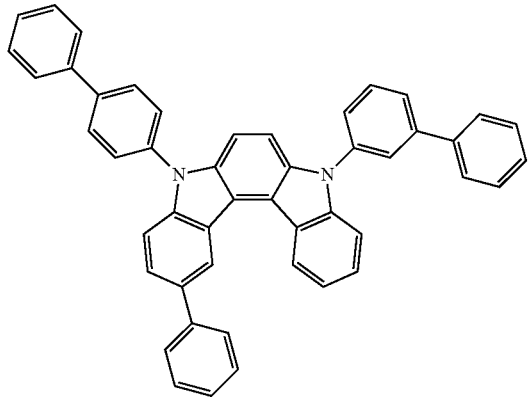
[C-18]
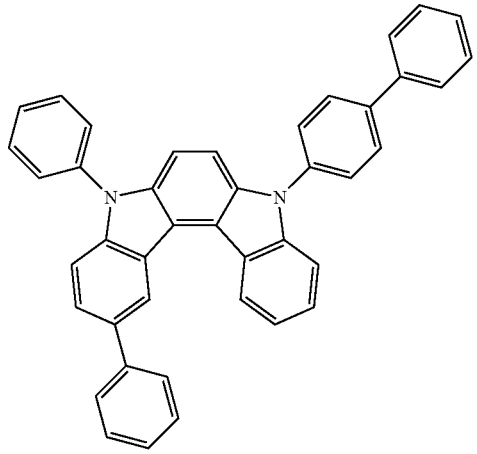
[C-19]
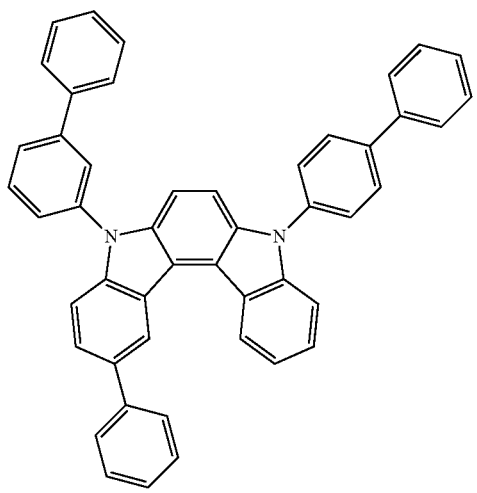
[C-20]
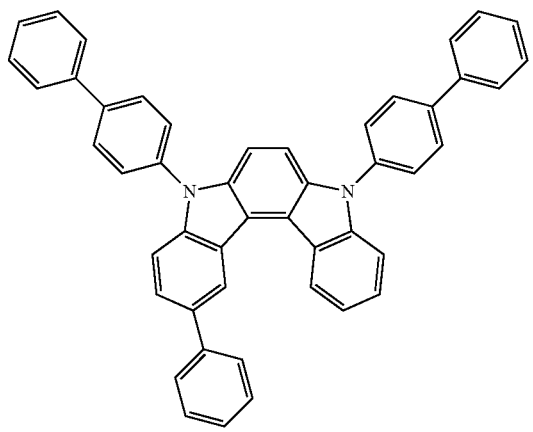
[C-21]
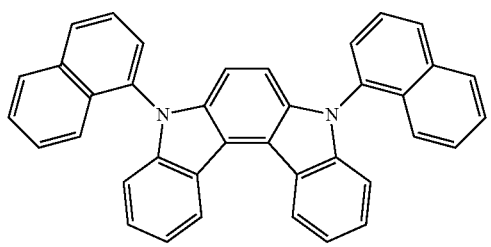
[C-22]
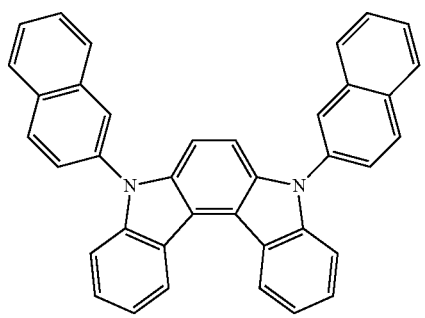
[C-23]
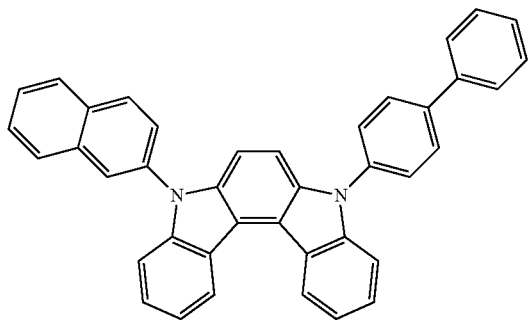
[C-24]
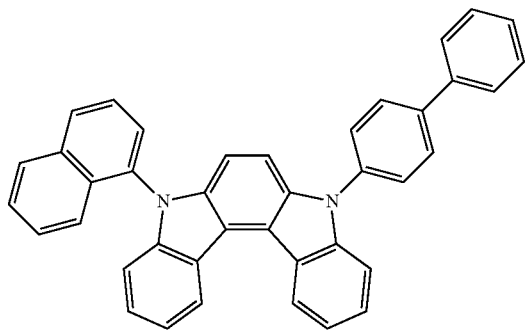

[C-25]
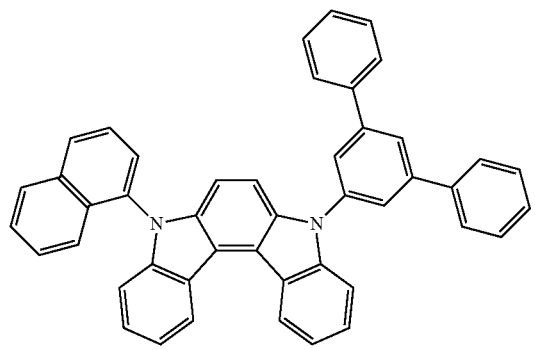
[C-26]
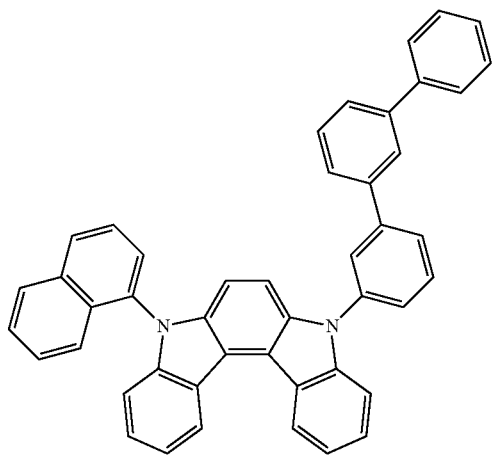
[C-27]
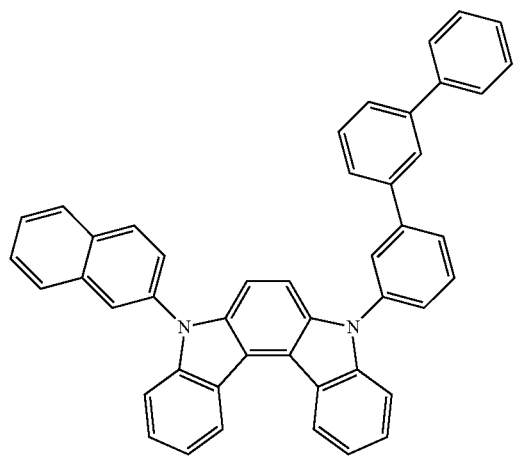
[C-28]
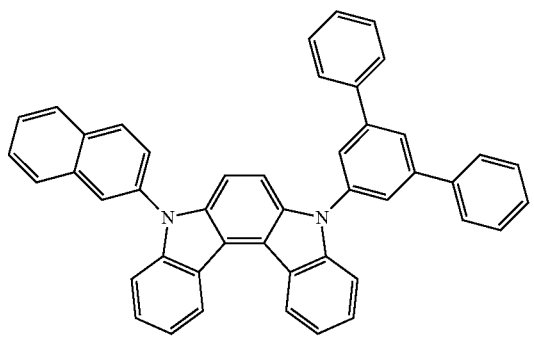
[C-29]
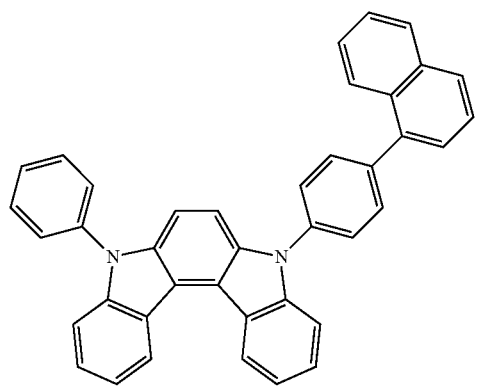
[C-30]
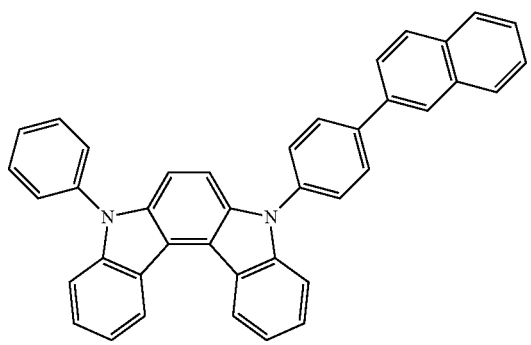

-continued
[C-31]
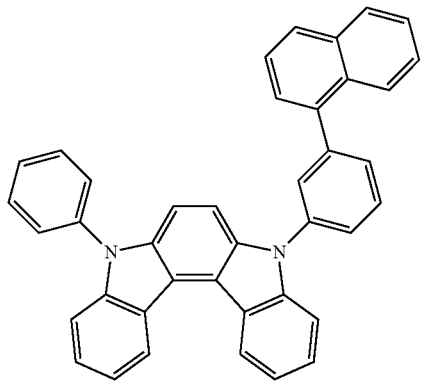
[C-32]
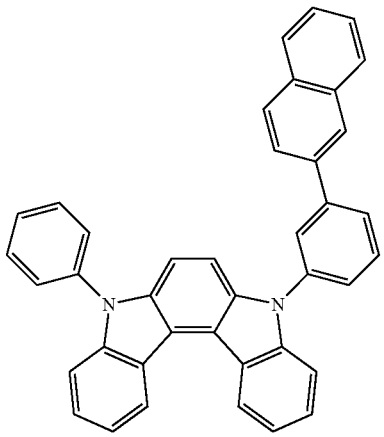
[C-33]
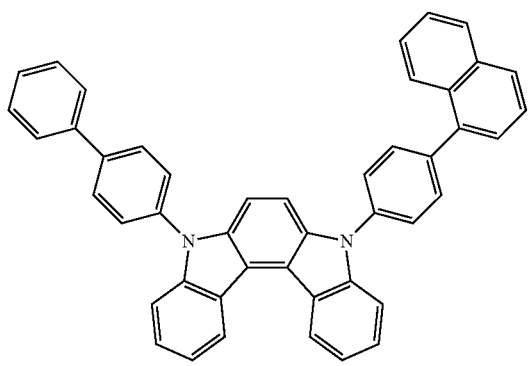
[C-34]
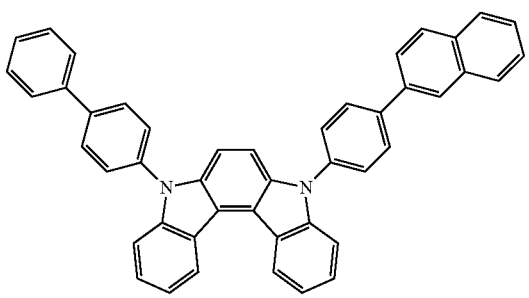
[C-35]
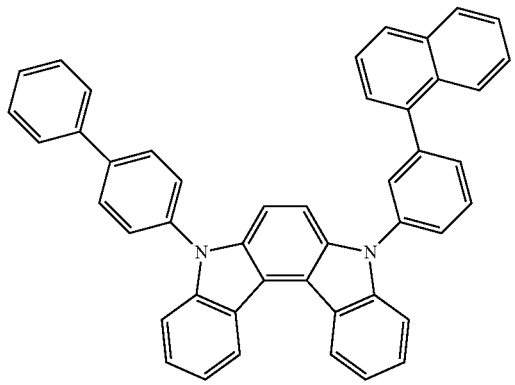
[C-36]
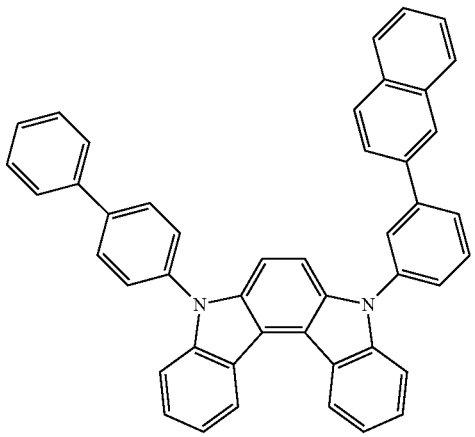
[C-37]
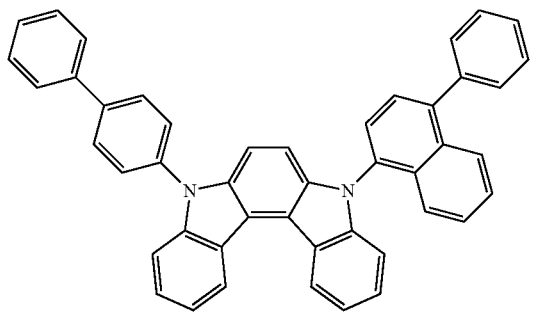
[C-38]
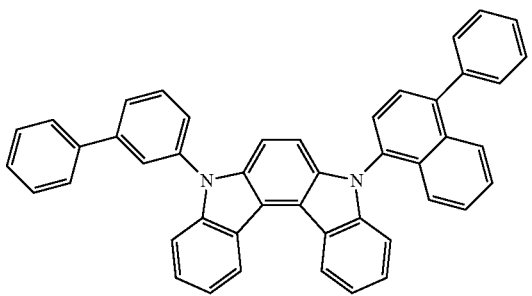

-continued
[C-39]
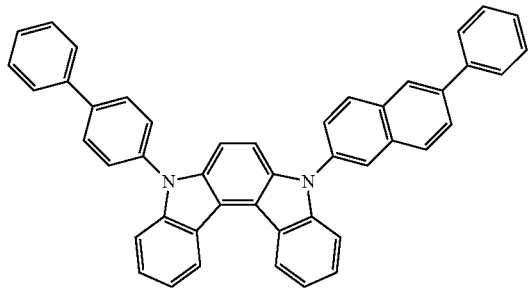
[C-40]
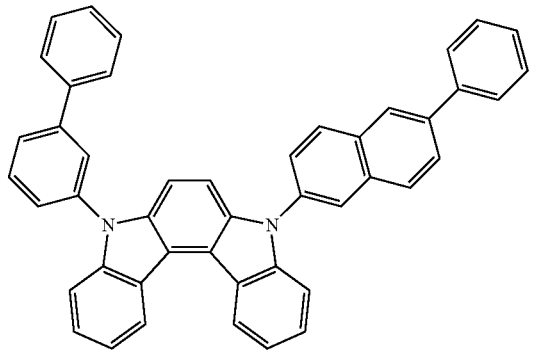
[C-41]
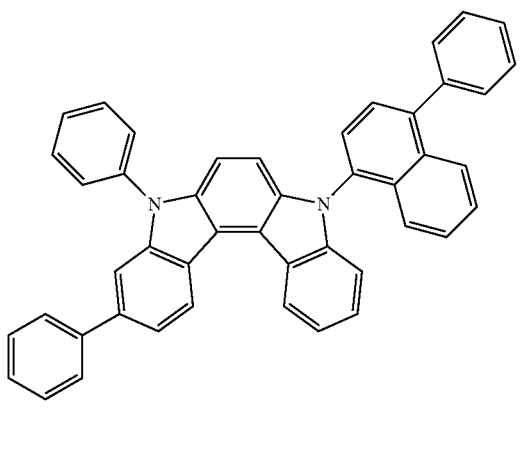
[C-42]
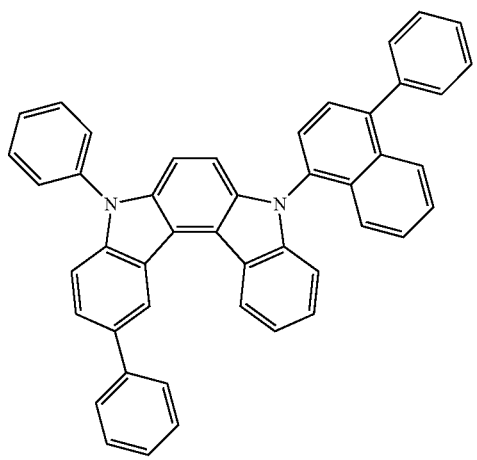
[C-43]
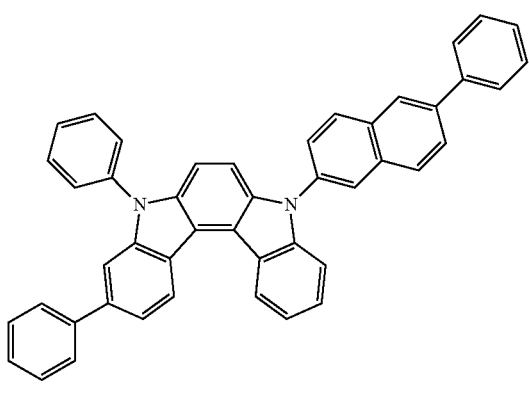
[C-44]
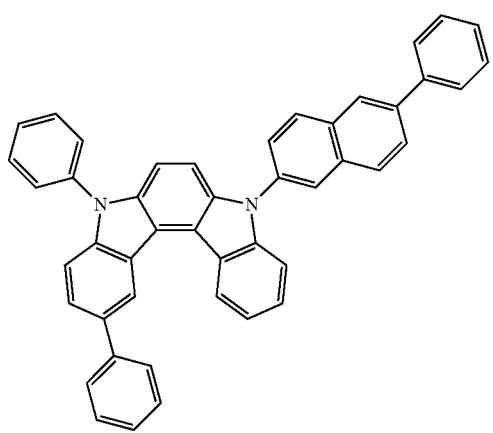

-continued
[C-45]
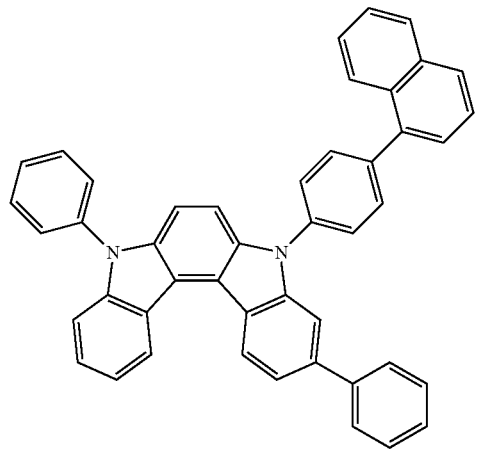
[C-46]
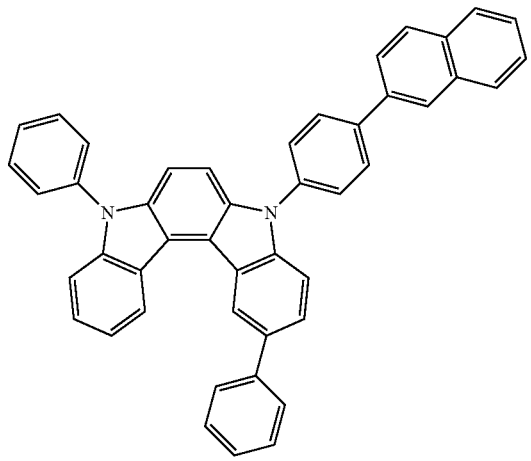
[C-47]
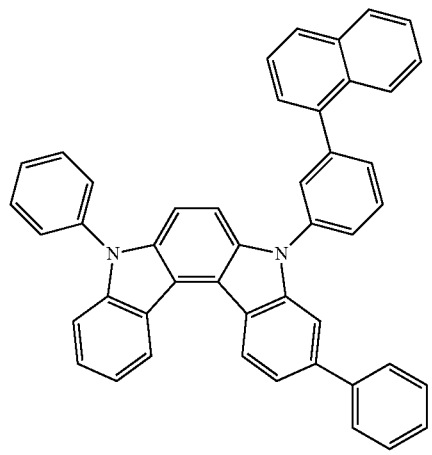
[C-48]
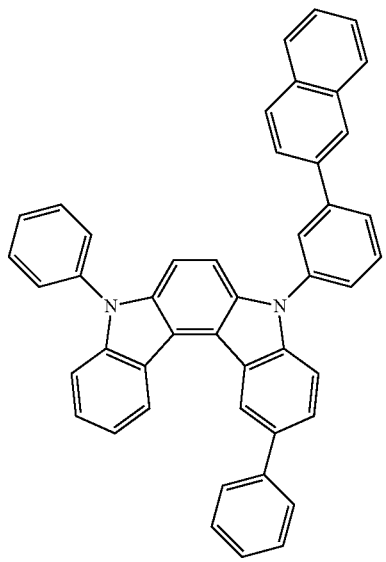
[C-49]
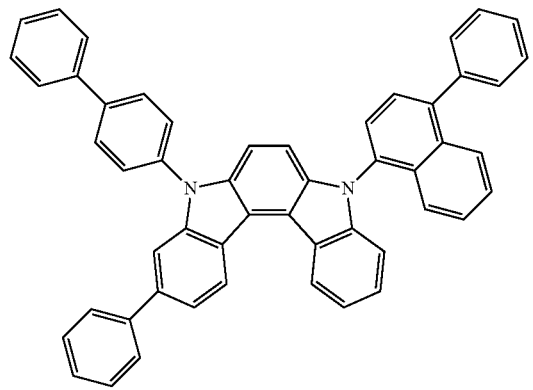
[C-50]
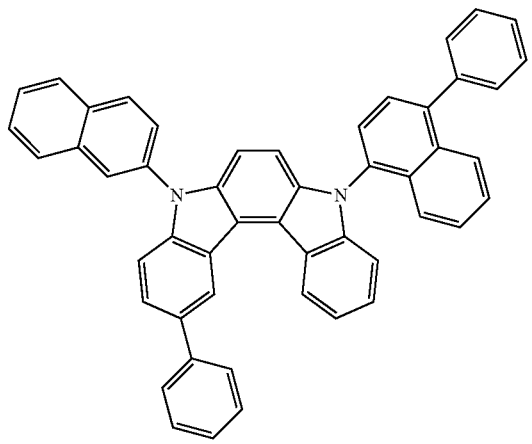

-continued

[C-51]
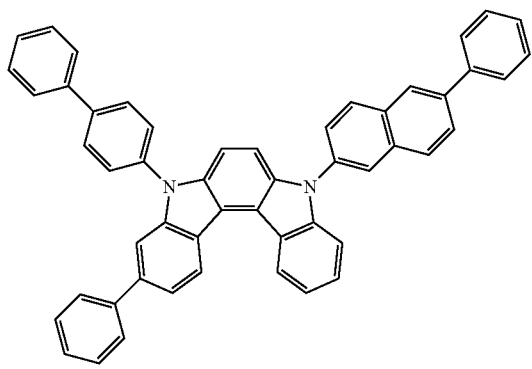

[C-52]
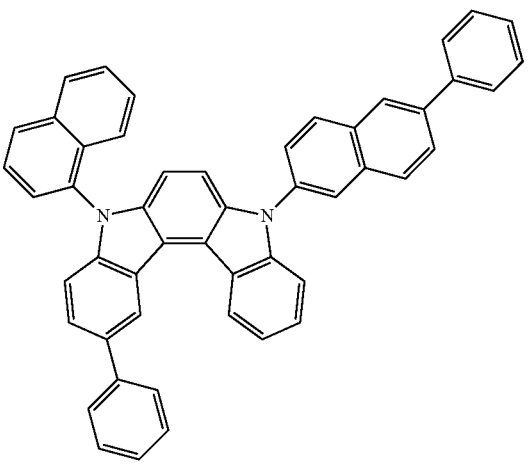

[C-53]
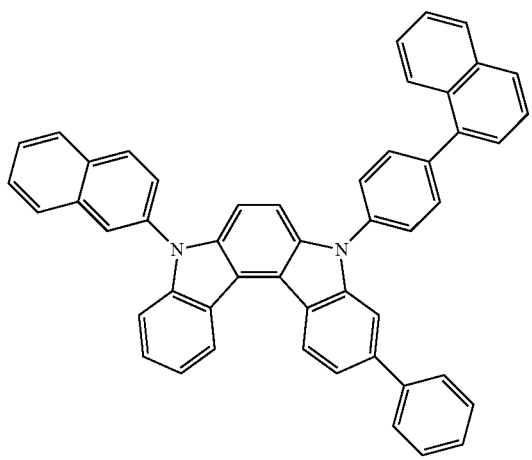

[C-54]
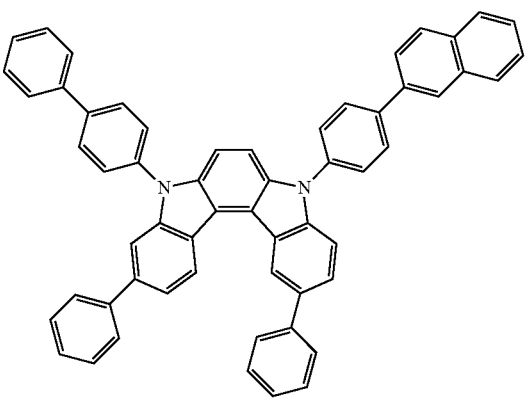

[C-55]
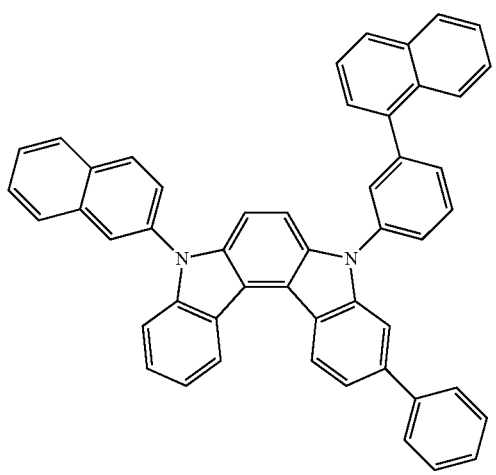

[C-56]
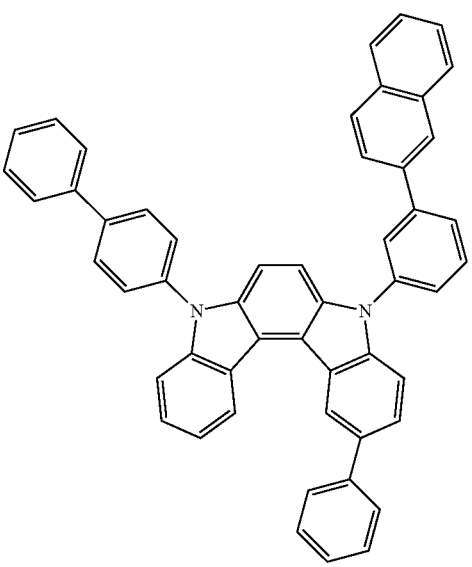

The first compound for an organic optoelectronic device and the second compound for an organic optoelectronic device may be included in a weight ratio of, for example, about 1:99 to about 99:1. Within the range, a desirable weight ratio may be adjusted using an electron transport capability of the first compound for an organic optoelectronic device and a hole transport capability of the second compound for an organic optoelectronic device to realize bipolar characteristics and thus to improve efficiency and life-span. Within the range, they may be included in a weight ratio of, for example, about 10:90 to about 90:10, about 20:80 to about 80:20, about 20:80 to about 70:30, about 20:80 to about 60:40, or about 20:80 to about 50:50. For example, they may be included in a weight ratio of about 20:80 to about 40:60, and for example, a weight ratio of about 30:70, about 40:60, or about 50:50.

Another compound may be included in addition to the first compound for an organic optoelectronic device and second compound for an organic optoelectronic device.

The compound for an organic optoelectronic device or the composition for an organic optoelectronic device may be a composition that further includes a dopant.

The dopant may be, for example, a phosphorescent dopant, for example a red, green, or blue phosphorescent dopant, for example a green or red phosphorescent dopant.

The dopant may be mixed with the compound for an organic optoelectronic device or composition for an organic optoelectronic device in a small amount to cause light emission, and may be generally a material such as a metal complex that emits light by multiple excitation into a triplet or more. The dopant may be, for example an inorganic, organic, or organic/inorganic compound, and one or more kinds thereof may be used.

Examples of the dopant may be a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z.

$$L^1MX^a \qquad \text{[Chemical Formula Z]}$$

In Chemical Formula Z, M is a metal, and $L^5$ and $X^a$ are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof, and the L and X may be, for example a bidentate ligand.

The compound for an organic optoelectronic device or the composition for an organic optoelectronic device may be applied by a dry film formation method such as chemical vapor deposition (CVD).

Hereinafter, an organic optoelectronic device including the compound for an organic optoelectronic device or the composition for an organic optoelectronic device is described.

The organic optoelectronic device may be a device to convert electrical energy into photoenergy or vice versa, and may be, for example, an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views showing organic light emitting diodes according to example embodiments.

Referring to FIG. 1, an organic optoelectronic device 100 according to an example embodiment includes an anode 120 and a cathode 110 and facing each other and an organic layer 105 disposed between the anode 120 and the cathode 110.

The anode 120 may be made of a conductor having a large work function to help hole injection, and may be for example metal, metal oxide and/or a conductive polymer. The anode 120 may be, for example a metal such as nickel, platinum, vanadium, chromium, copper, zinc, gold, and the like or an alloy thereof, metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDOT), polypyrrole, and polyaniline.

The cathode 110 may be made of a conductor having a small work function to help electron injection, and may be for example metal, metal oxide and/or a conductive polymer. The cathode 110 may be, for example, a metal such as magnesium, calcium, sodium, potassium, titanium, indium, yttrium, lithium, gadolinium, aluminum silver, tin, lead, cesium, barium, and the like or an alloy thereof; a multilayer structure material such as LiF/Al, LiO$_2$/Al, LiF/Ca, LiF/Al and BaF$_2$/Ca.

The organic layer 105 includes the compound for an organic optoelectronic device or the composition for an organic optoelectronic device according to an embodiment.

The organic layer 105 may include a light emitting layer 130 and the light emitting layer 130 may include the compound for an organic optoelectronic device or the composition for an organic optoelectronic device.

The composition for an organic optoelectronic device that further includes the dopant may be, for example, a green or red light emitting composition.

The light emitting layer 130 may include, for example, the first compound and the second compound as each phosphorescent host.

The organic layer may further include an auxiliary layer in addition to the light emitting layer.

The auxiliary layer may be, for example, a hole auxiliary layer 140.

Referring to FIG. 2, an organic light emitting diode 200 may further include a hole auxiliary layer 140 in addition to the light emitting layer 130. The hole auxiliary layer 140 may further increase hole injection and/or hole mobility and block electrons between the anode 120 and the light emitting layer 130.

The hole auxiliary layer 140 may include, for example, at least one of compounds of Group D.

For example, the hole auxiliary layer 140 may include a hole transport layer between the anode 120 and the light emitting layer 130 and a hole transport auxiliary layer between the light emitting layer 130 and the hole transport layer, and at least one of compounds of Group D may be included in the hole transport auxiliary layer.

[Group D]

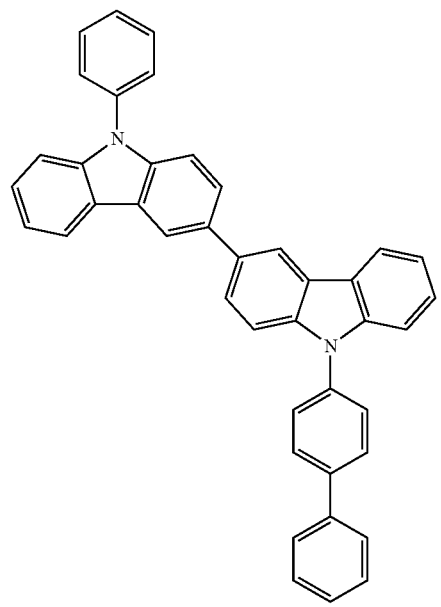

121
-continued
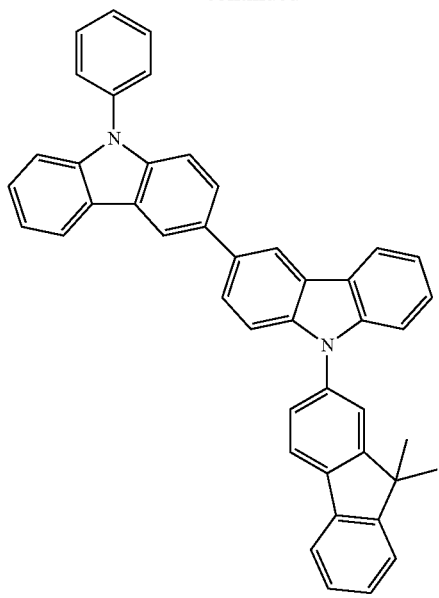
122
-continued
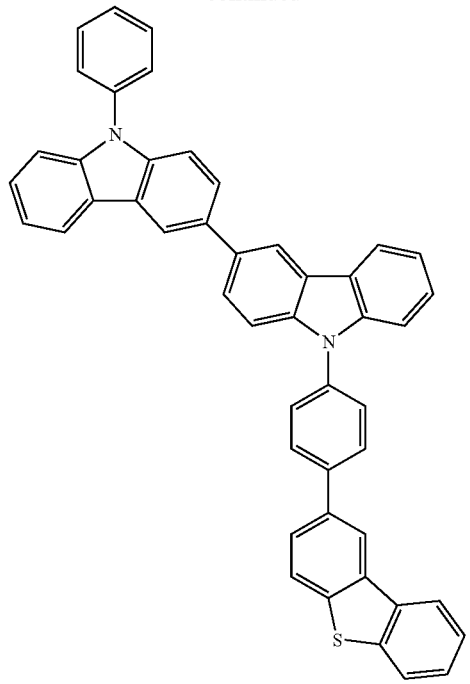
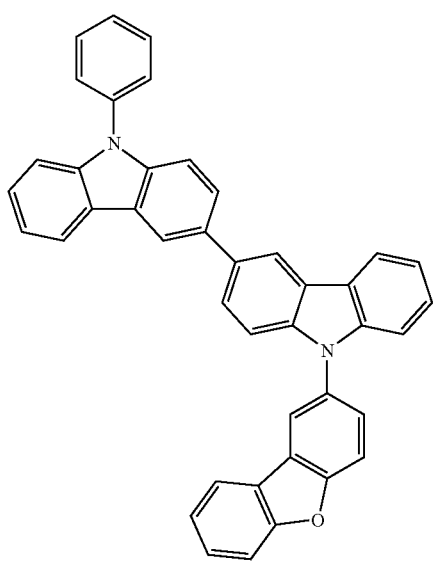
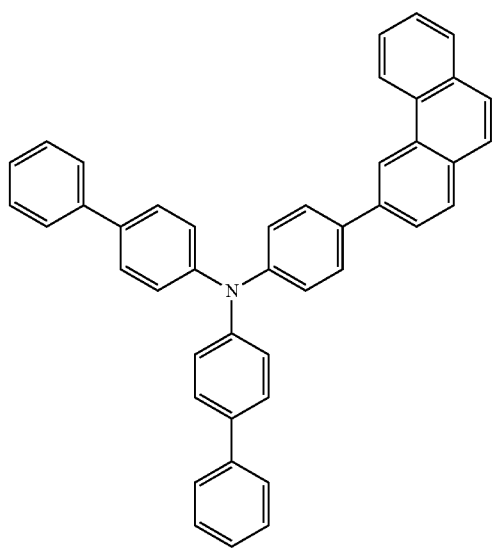

123
-continued
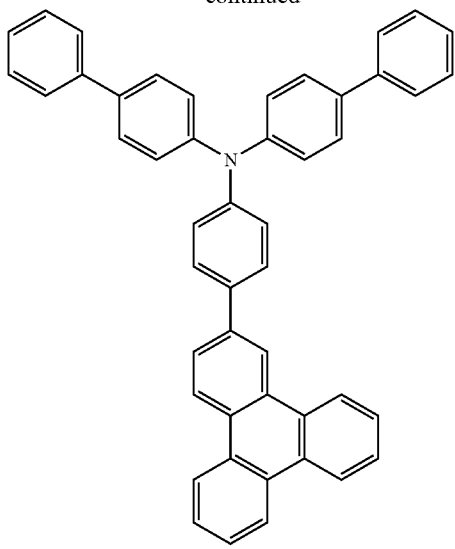
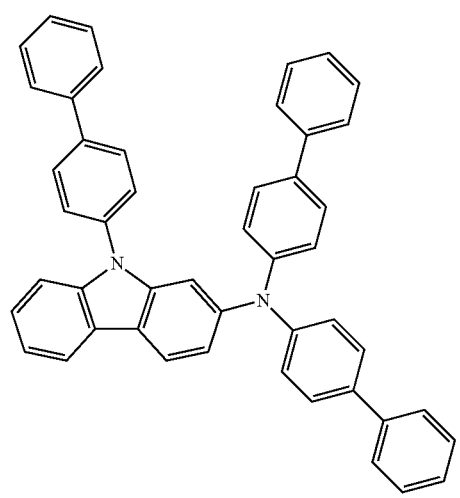
124
-continued
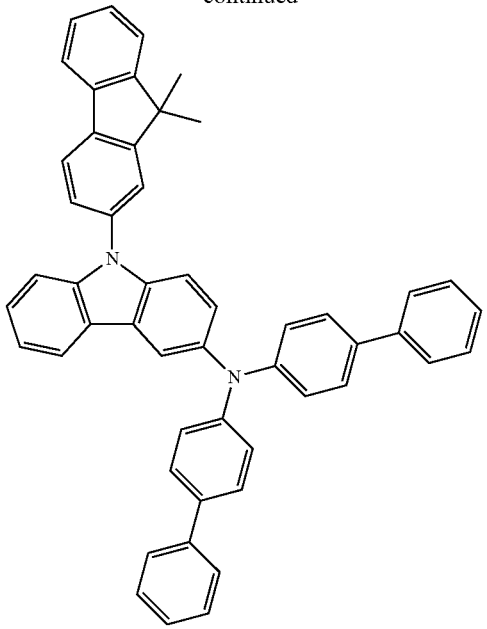
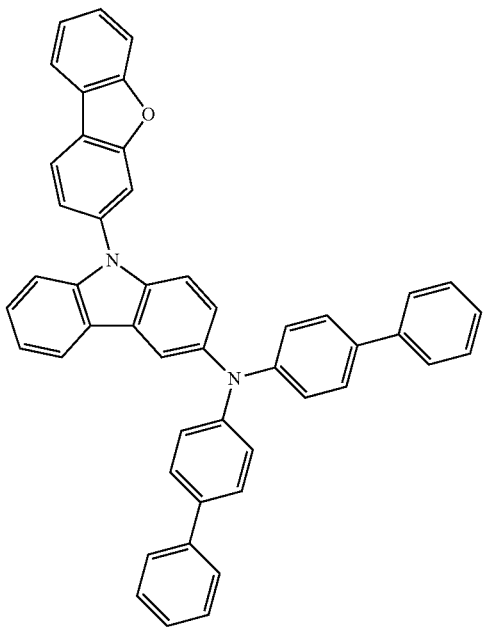

125
-continued
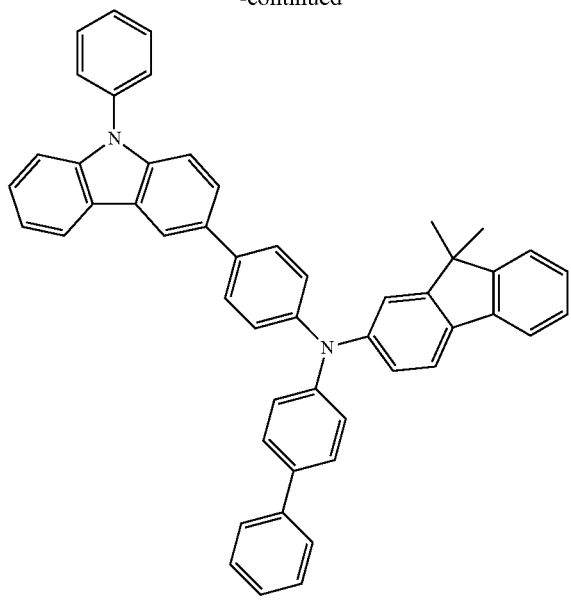
126
-continued
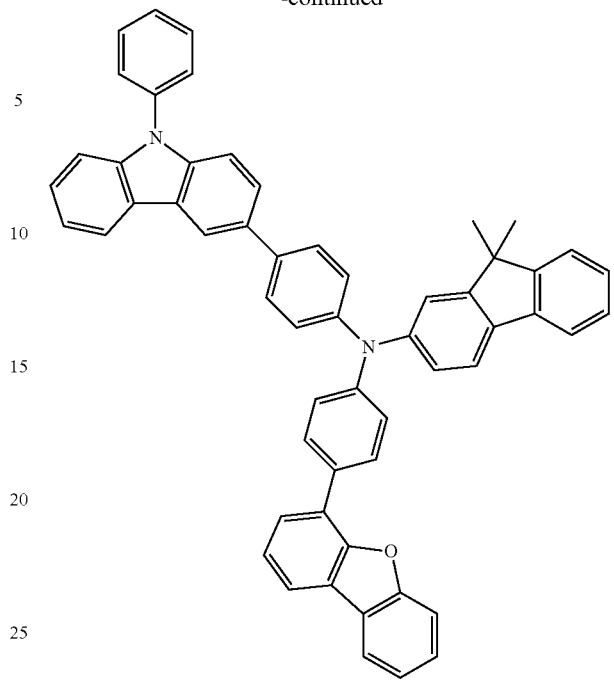
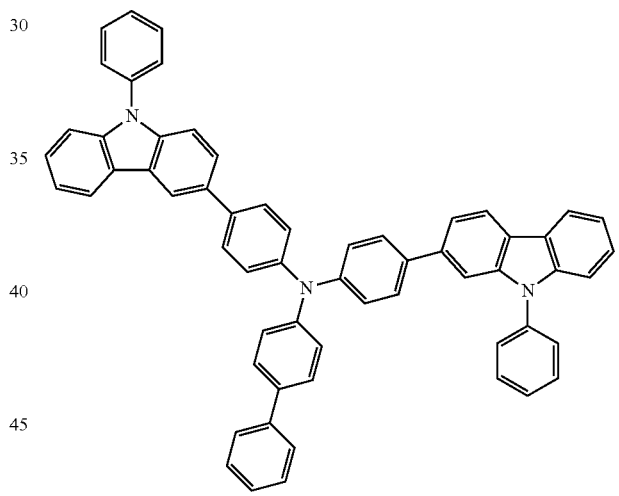
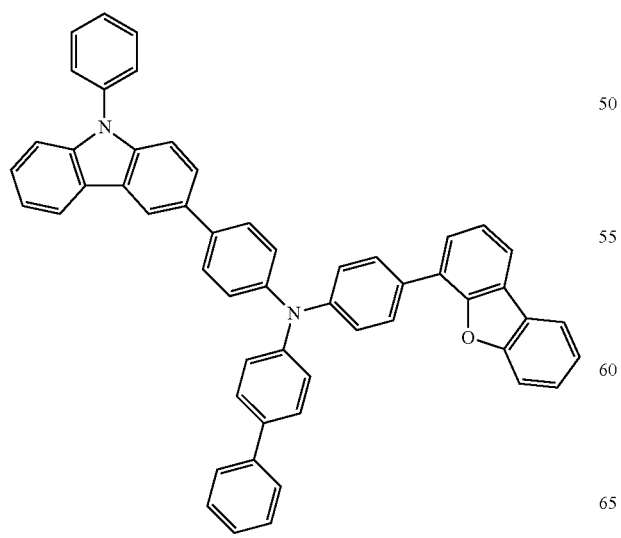

127
-continued
128
-continued
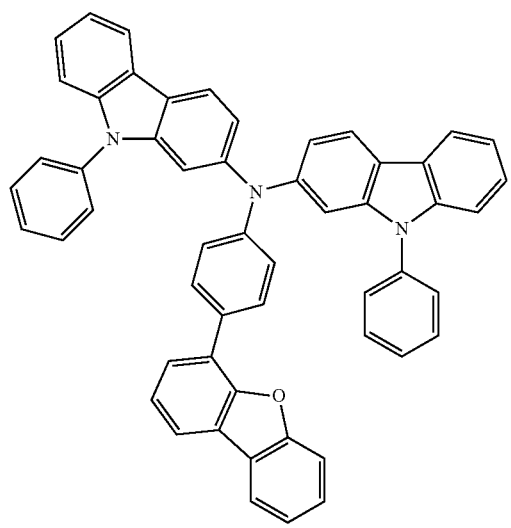
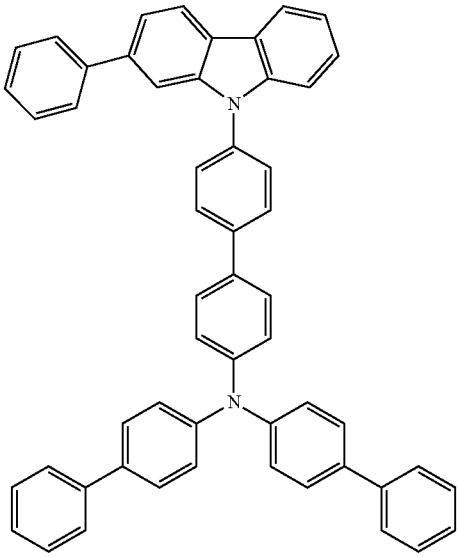
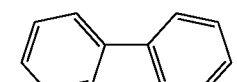
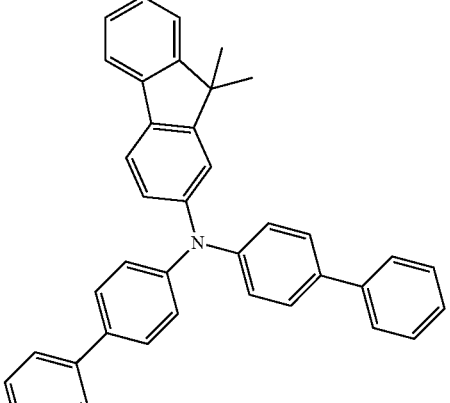
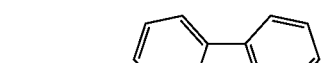
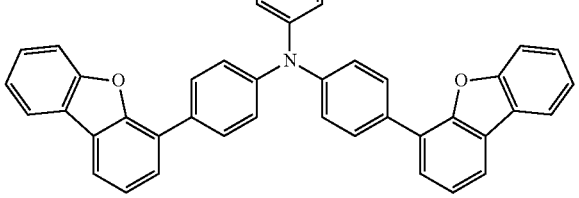

129
-continued
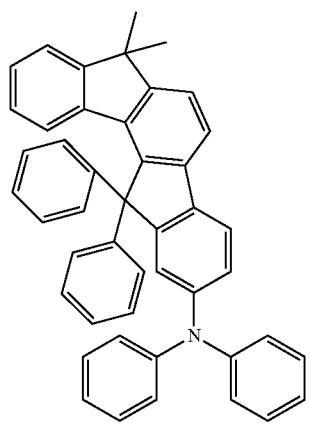
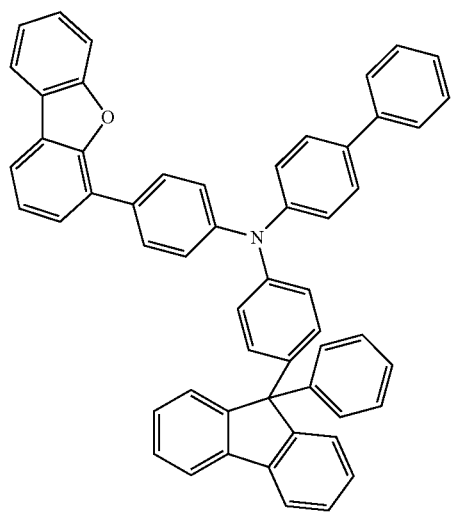
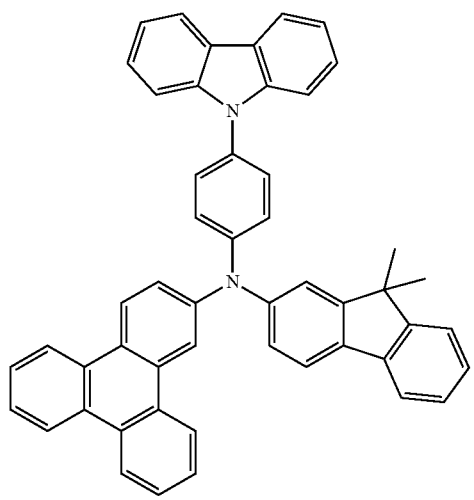
130
-continued
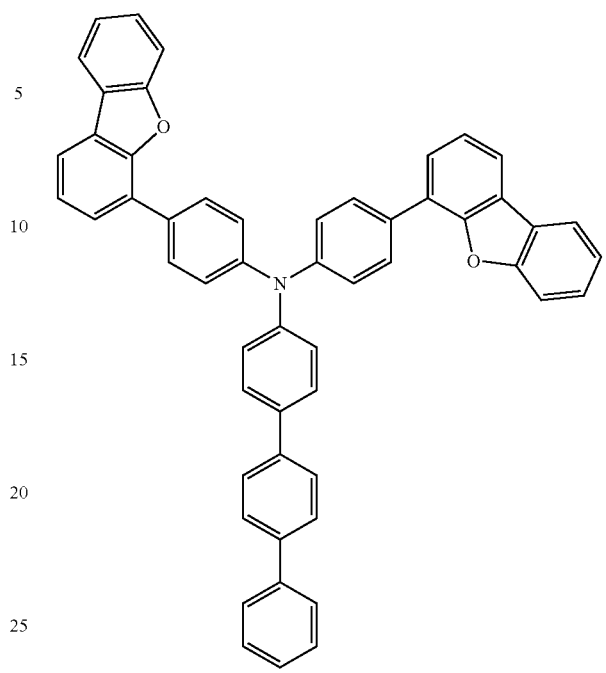
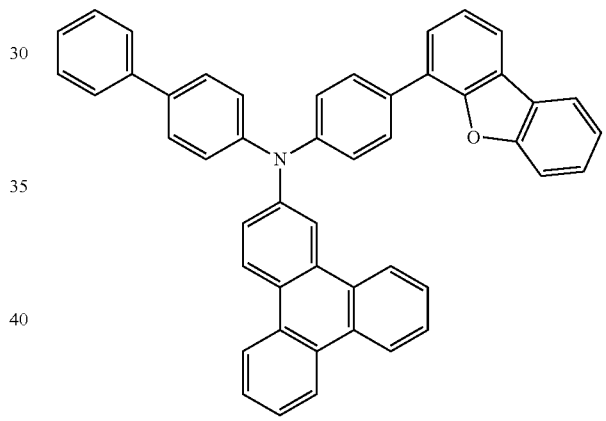
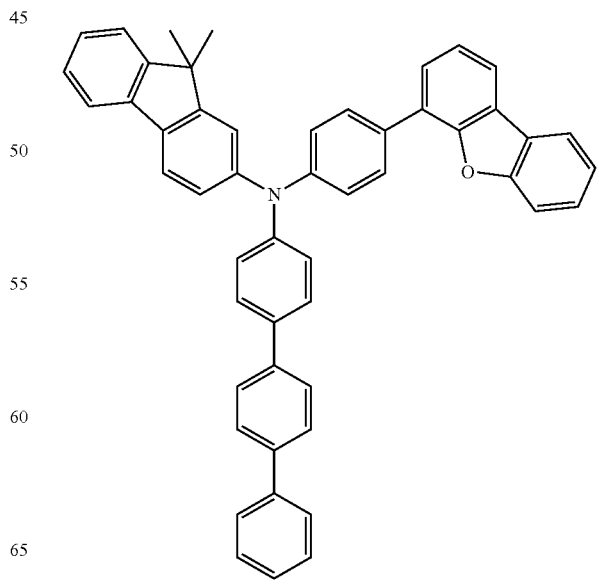

131
-continued
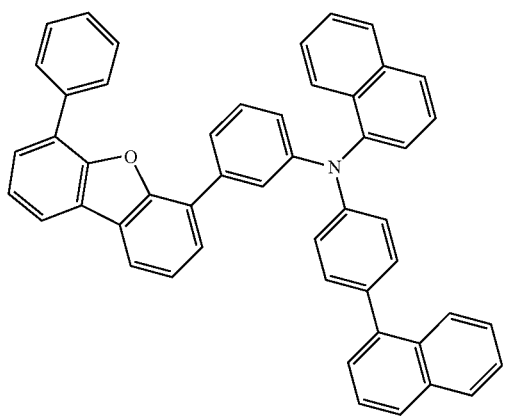
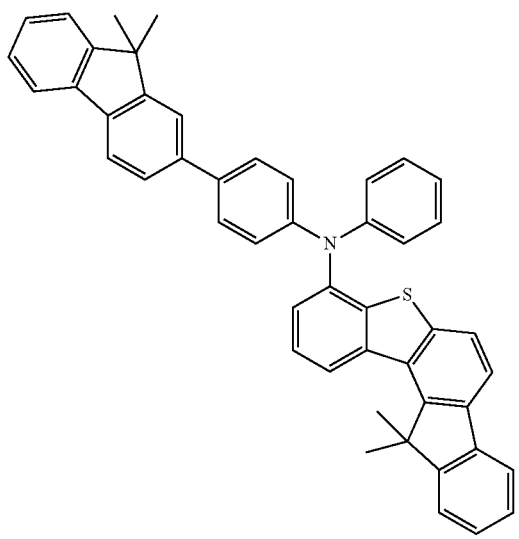
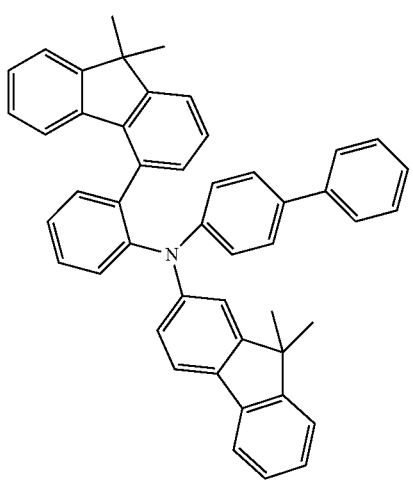
132
-continued
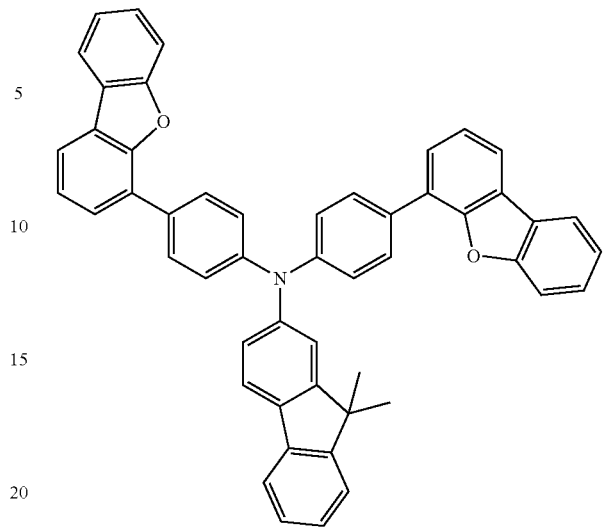
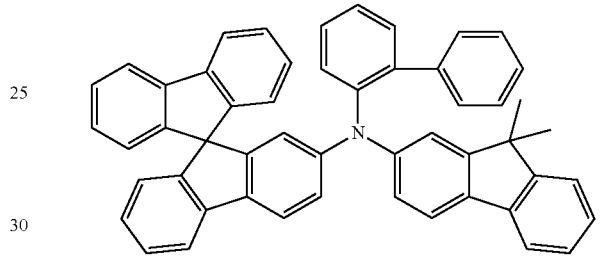
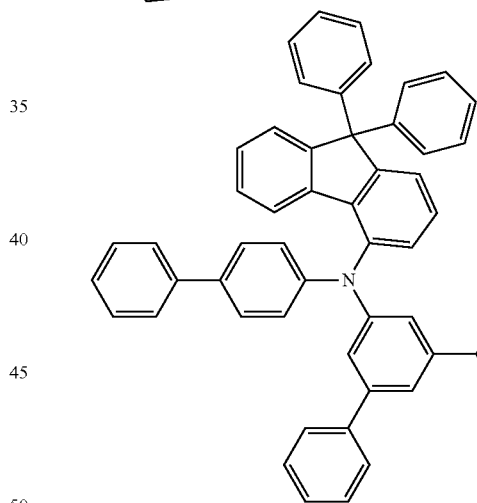
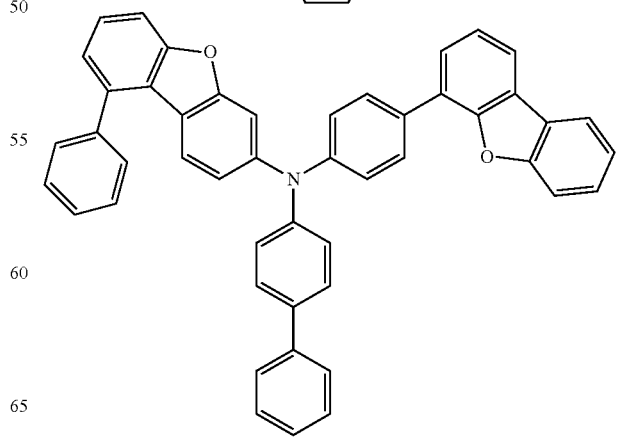

133
-continued
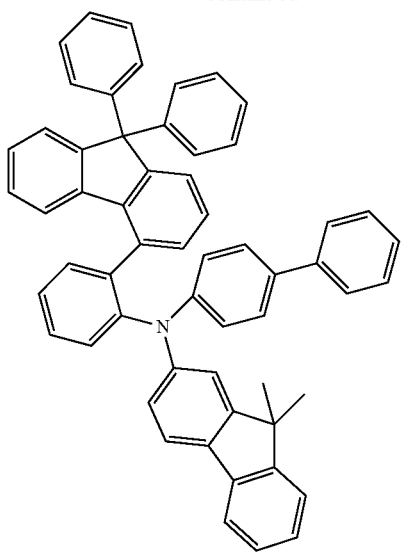
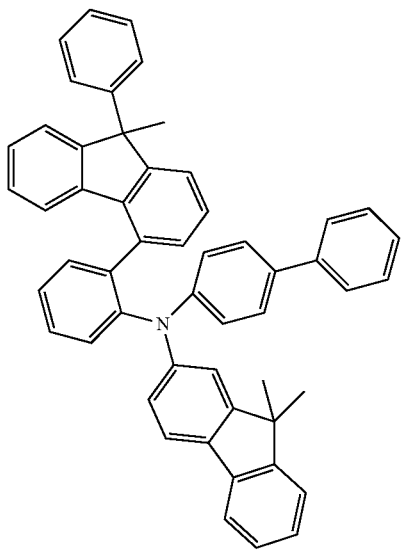
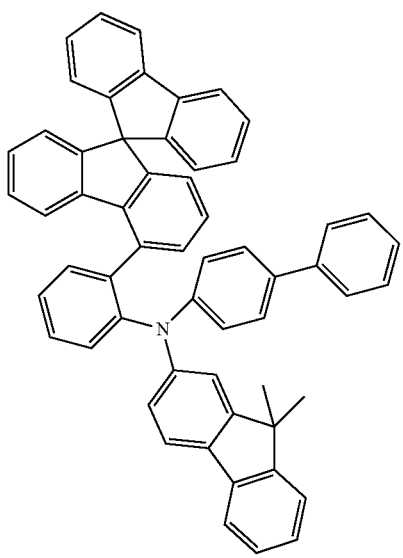
134
-continued
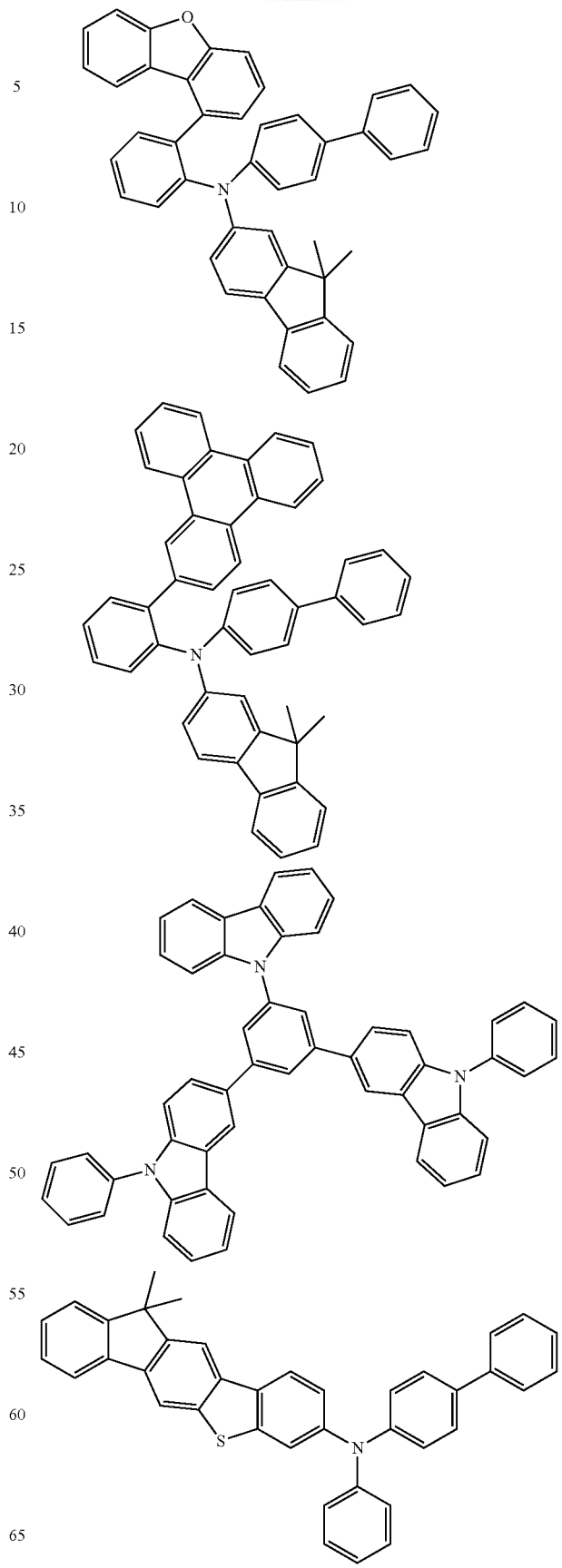

135
-continued
136
-continued
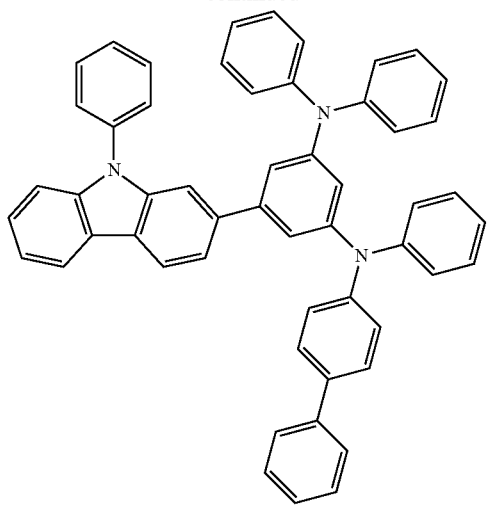
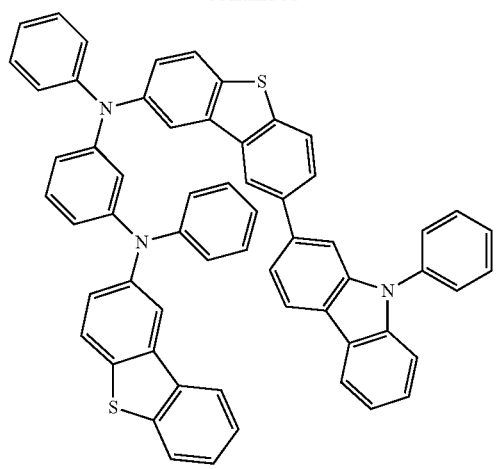
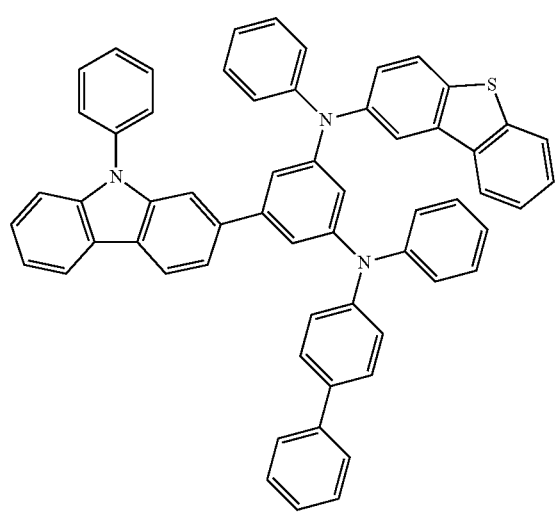
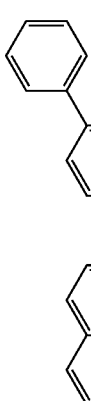
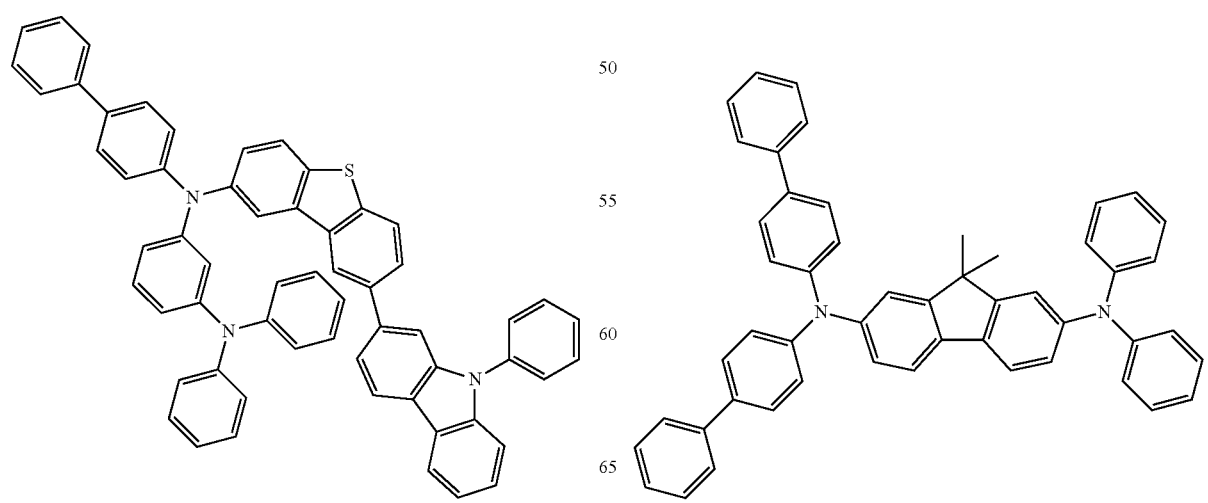

137
-continued
138
-continued
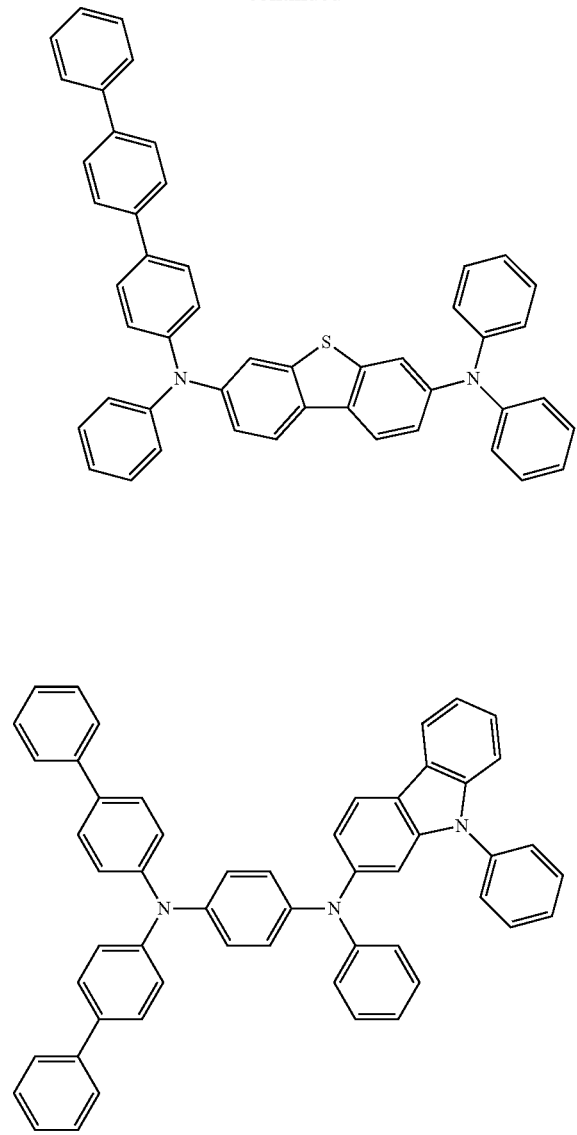
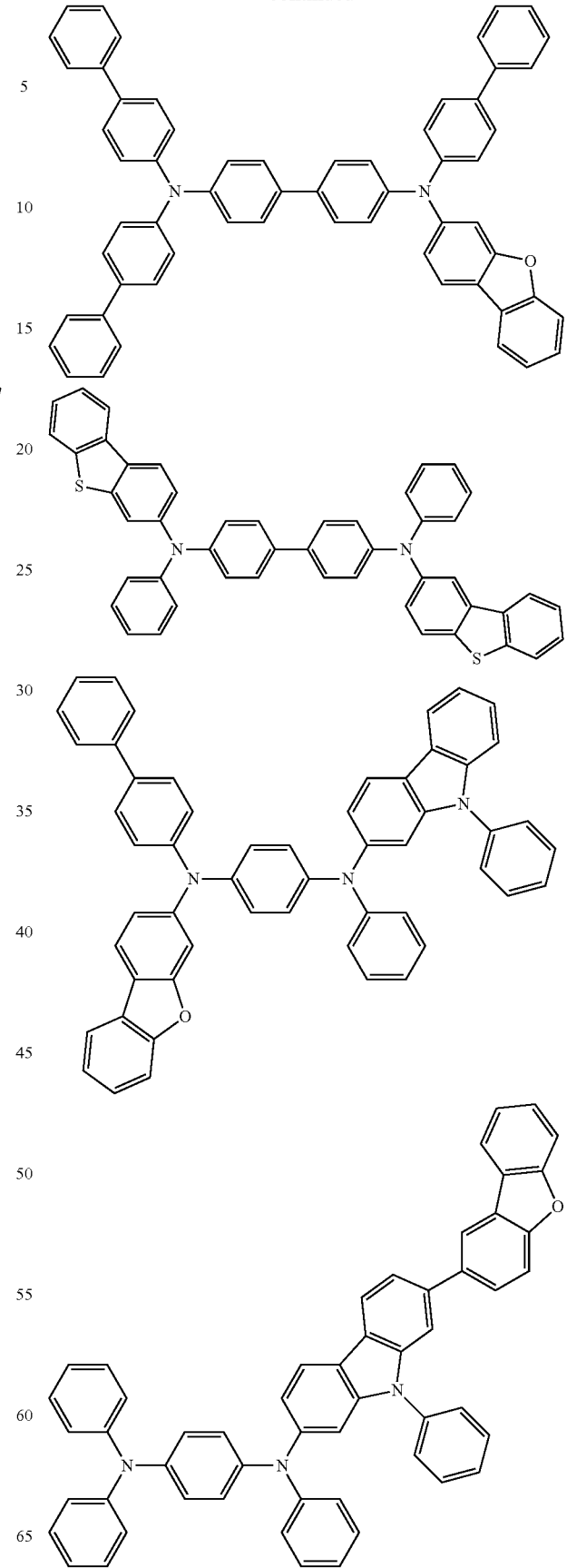

139
-continued
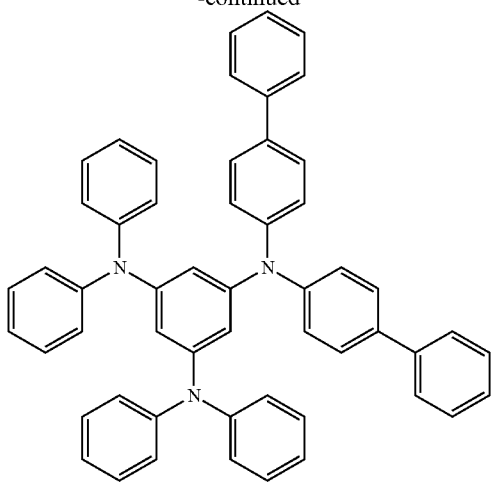
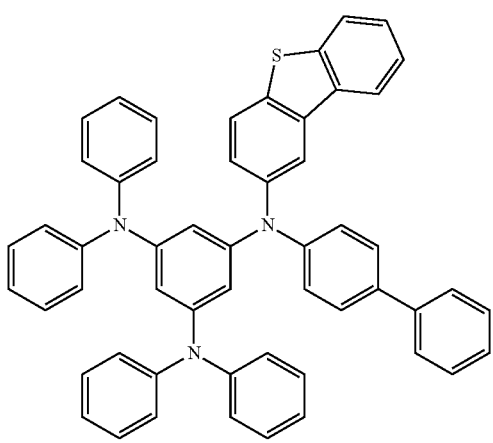
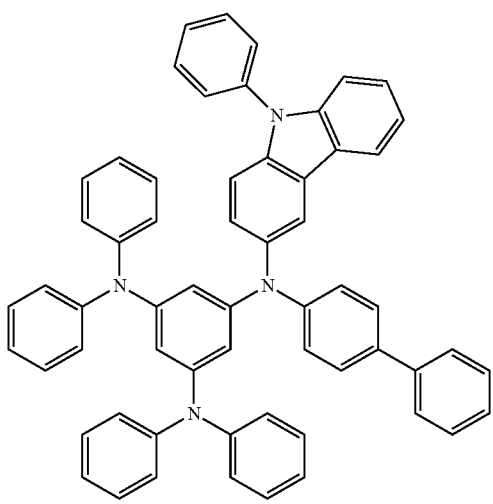
140
-continued
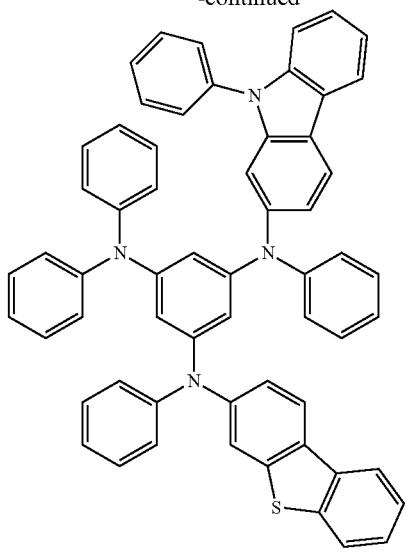
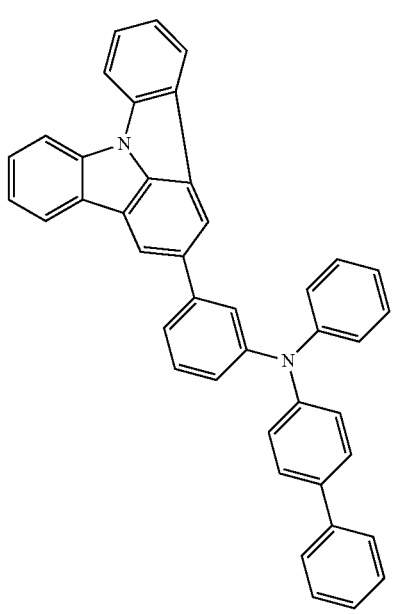
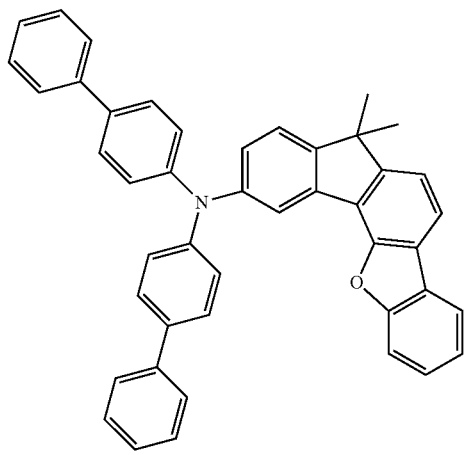

141
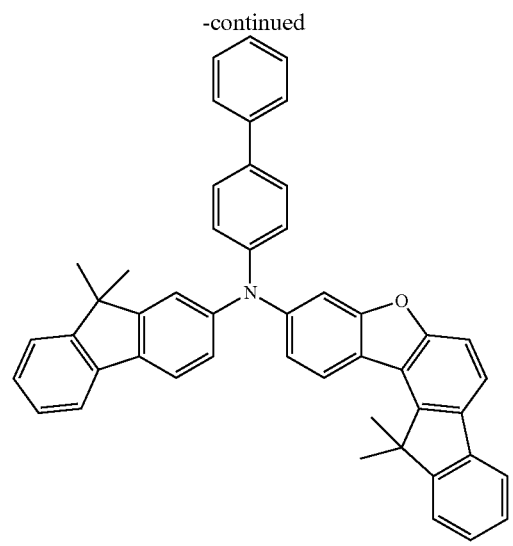
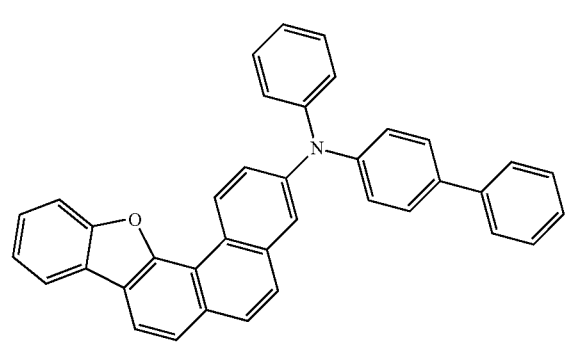
142
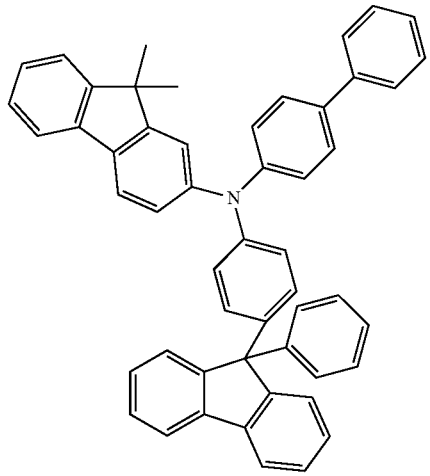
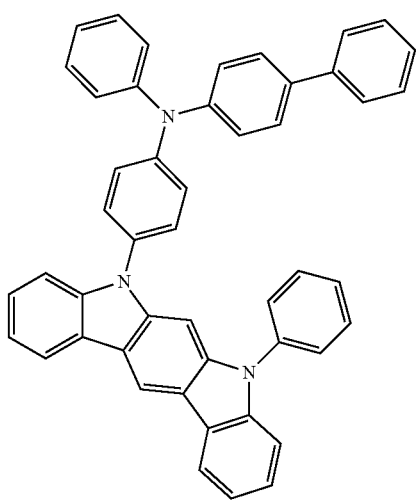
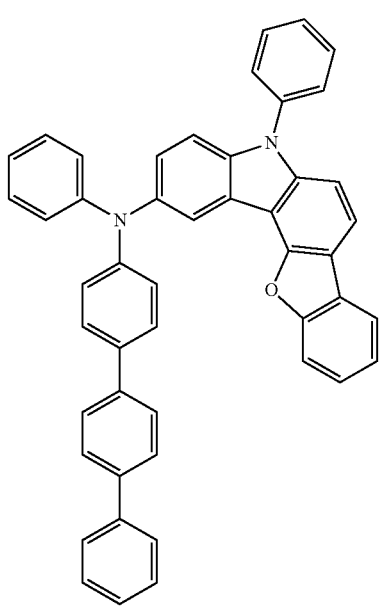

143
-continued

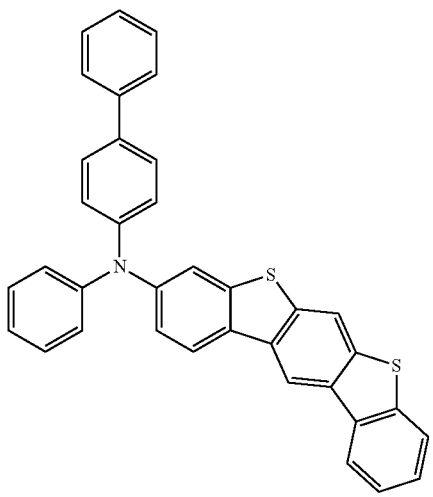

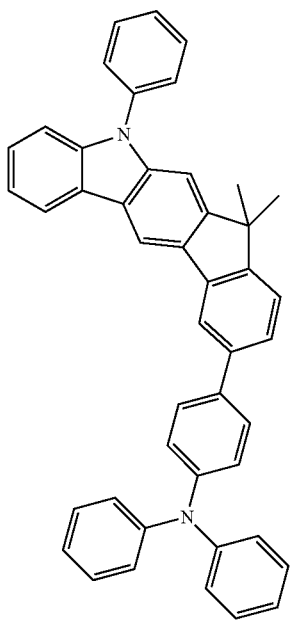

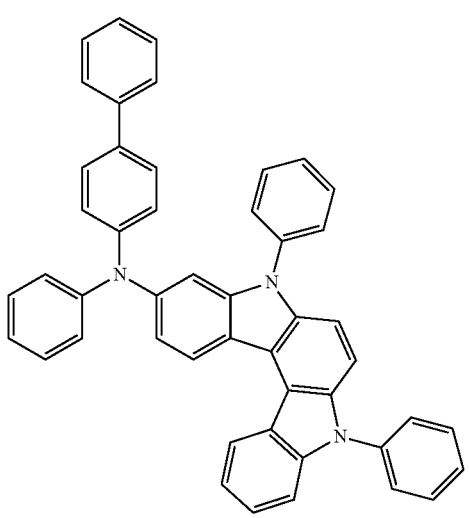

144
-continued

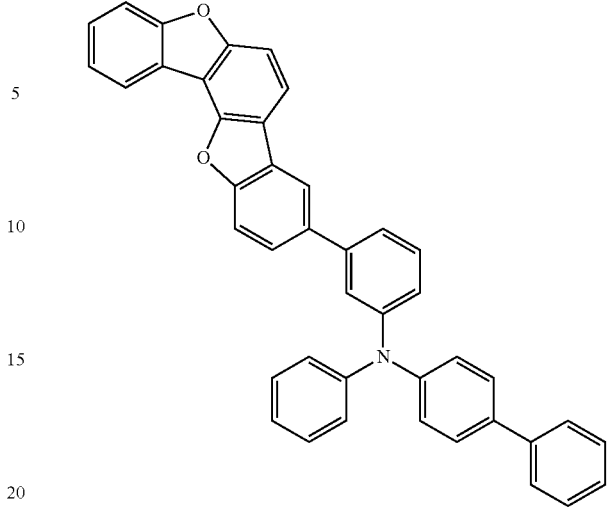

In the hole transport auxiliary layer, known compounds disclosed in U.S. Pat. No. 5,061,569, which is incorporated herein by reference for all purposes, JP1993-009471A, WO1995-009147A1, JP1995-126615A, JP1998-095973A, and the like and compounds similar thereto may be used in addition to the compound.

In an embodiment, in FIG. 1 or 2, an organic light emitting diode may further include an electron transport layer, an electron injection layer, or a hole injection layer as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co. Ltd., TCI Inc., Tokyo Chemical Industry, or P&H Tech (as far as there is no particular comment), or were synthesized by known methods.

(Preparation of Compound for Organic Optoelectronic Device)

A compound according to an embodiment was synthesized through the following procedure.

Preparation of First Compound for Organic Optoelectronic Device

Synthesis Example 1: Synthesis of Compound A-2

[Reaction Scheme 1]

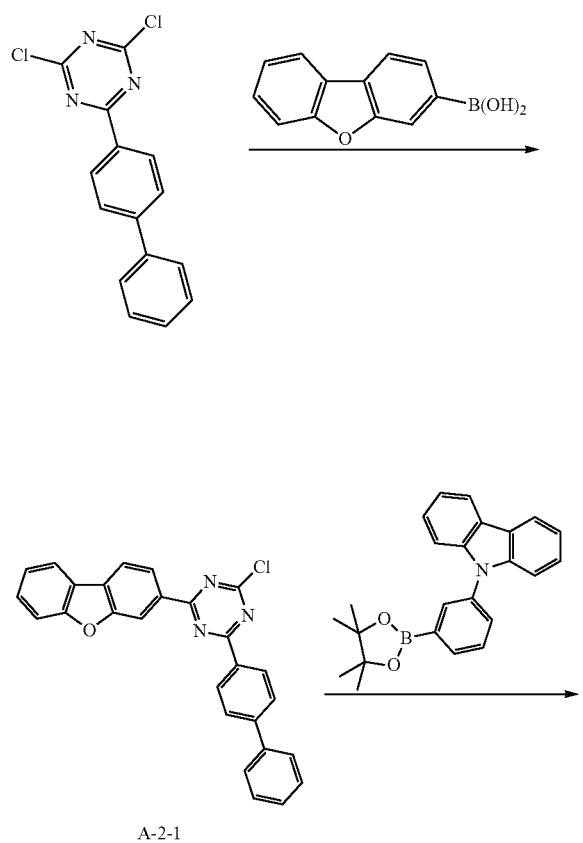

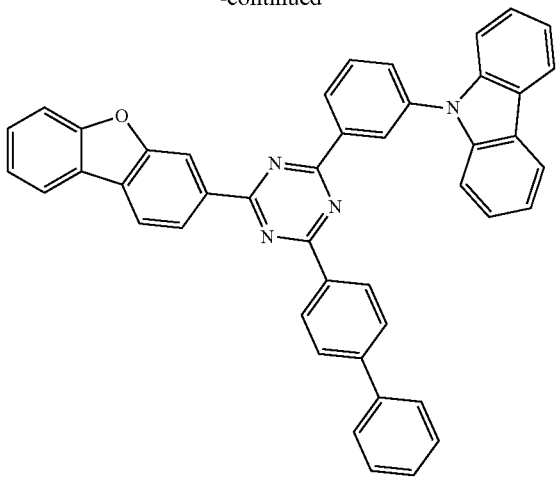

A-2 a) Synthesis of Intermediate A-2-1

In a 500 mL round-bottomed flask, 30.2 g (100 mmol) of 2,4-dichloro-6-(4-phenylphenyl)-1,3,5-triazine was added into 100 mL of tetrahydrofuran, 100 mL of toluene, and 100 mL of distilled water, then 0.9 equivalent of dibenzofuran-3-boronic acid, 0.03 equivalent of tetrakistriphenylphosphine palladium, and 2 equivalent of potassium carbonate were added, and the resultant was heated and refluxed under a nitrogen atmosphere. After 6 hours, the reaction solution was cooled down, an aqueous layer was removed, and an organic layer was dried under a reduced pressure. The obtained solid was washed with water and hexane, and then the solid was recrystallized with 200 mL of toluene to obtain 26.0 g (60% yield) of Intermediate A-2-1.

b) Synthesis of Compound A-2

In a 500 mL round-bottomed flask, 9.72 g (22.4 mmol) of the synthesized Intermediate A-2-1 was added into 80 mL of tetrahydrofuran, 40 mL of distilled water, then 1.0 equivalent of 9-[3-(4,4,5,5-tetramethyl-1,3,2-dioxaborolan-2-yl)phenyl]-carbazole (CAS: 870119-58-7), 0.03 equivalent of tetrakistriphenylphosphine palladium, and 2 equivalent of potassium carbonate were added, and the resultant was heated and refluxed under a nitrogen atmosphere. After 18 hours, the reaction solution was cooled down, and the precipitated solid was filtered and washed with 500 mL of water. The solid was recrystallized with 500 mL of monochloro benzene to obtain 12.2 g of Compound A-2.

LC/MS calculated for: C45H28N4O Exact Mass: 640.2263 found for: 641.22.

Synthesis Example 2: Synthesis of Compound A-6

[Reaction Scheme 2]

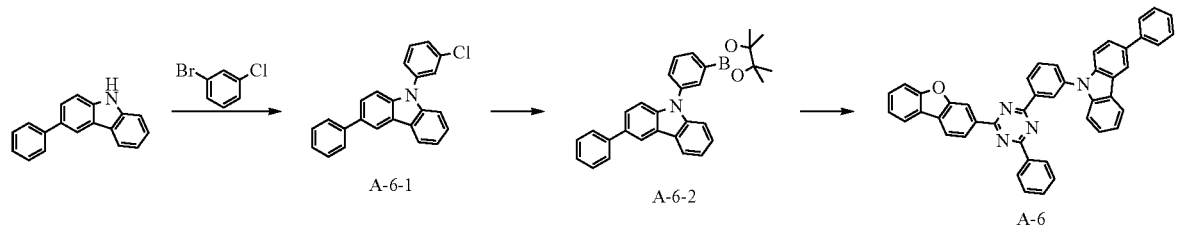

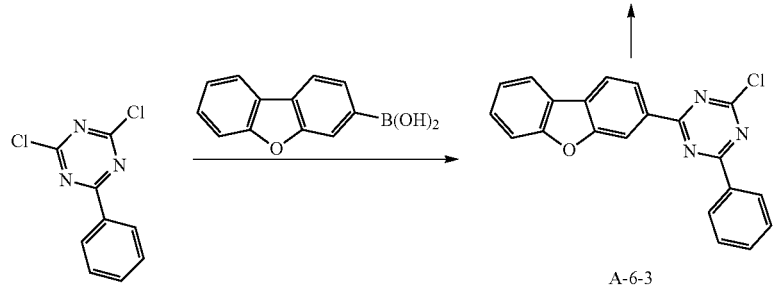

A-6-3 a) Synthesis of Intermediate A-6-1

1 equivalent of 3-phenyl-9H-carbazole and 1.2 equivalent (eq) of 3-chloro-1-bromobenzene were added into xylene, and then 2 eq of sodium t-butoxide and 0.05 eq of $Pd_2(dba)_3$ were suspended in xylene to provide 0.2 M, then 0.15 eq of tri-tert-butylphosphine was added, and the resultant was reflux-stirred for 18 hours. It was stirred with adding methanol in 1.5 times of the solvent, and then the obtained solid was filtered and washed with 300 mL water. The solid was recrystallized using monochloro benzene to obtain Intermediate A-6-1 at a yield of 85%.

b) Synthesis of Intermediate A-6-2

In a 500 mL round-bottomed flask, 16.42 g (46.4 mmol) of the synthesized Intermediate A-6-1 was added into 200 mL of toluene, 0.05 equivalent of dichlorodiphenylphosphinoferrocene palladium, 1.2 equivalent of bispinacolato diboron, and 2 equivalent of potassium acetate were added, and the resultant was heated and refluxed under a nitrogen atmosphere for 18 hours. The reaction solution was cooled down and dripped into 1 L of water to collect a solid. The obtained solid was dissolved in a boiled toluene to be treated with an activated carbon and then was filtered by silica gel, and the filtrate was concentrated. The concentrated solid was stirred with a small amount of hexane, and the solid was filtered to obtain Intermediate A-6-2 at a yield of 85%.

c) Synthesis of Intermediate A-6-3

Intermediate A-6-3 was obtained at a yield of 60% in accordance with the same procedure as in the step a) of Synthesis Example 1, except that 22.6 g (100 mmol) of 2,4-dichloro-6-phenyltriazine was used.

d) Synthesis of Compound A-6

Compound A-6 was synthesized in accordance with the same procedure as in the step b) of Synthesis Example 1, except that the synthesized Intermediates A-6-2 and A-6-3 were used at each 1 equivalent, respectively.

LC/MS calculated for: C45H28N4O Exact Mass: 640.2263 found for: 641.23.

Synthesis Example 3: Synthesis of Compound A-21

[Reaction Scheme 3]

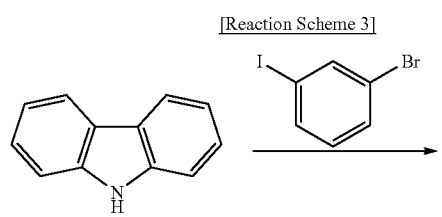

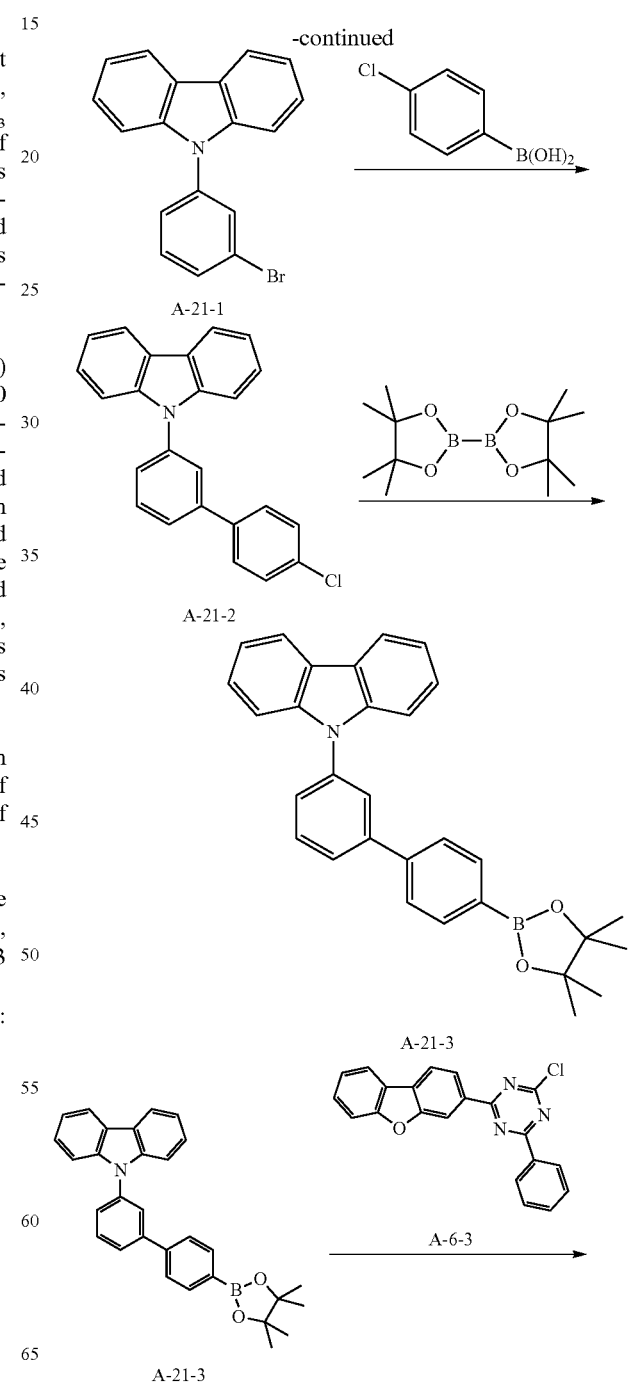

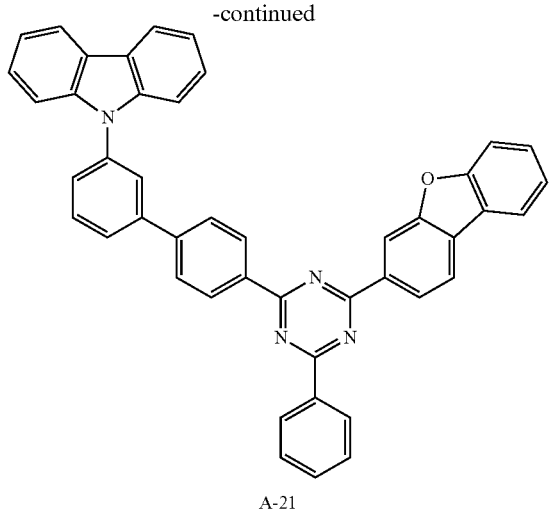

A-21 a) Synthesis of Intermediate A-21-1

An intermediate A-21-1 was synthesized in accordance with the same procedure as in the step a) of Synthesis Example 2, except that 1 equivalent of 9H-carbazole and 1.2 equivalent of 3-chloro-1-bromobenzene were used.

b) Synthesis of Intermediate A-21-2

In a 500 mL round-bottomed flask, 1 equivalent of the synthesized intermediate A-21-1 was added into 140 mL of tetrahydrofuran and 70 mL of distilled water, 1.1 equivalent of 4-chlorophenyl boronic acid, 0.03 equivalent of tetrakis-triphenylphosphine palladium, and 2 equivalent of potassium carbonate were added, and the resultant was heated and refluxed under a nitrogen atmosphere. After 12 hours, the reaction solution was cooled down, and a solvent was removed under a reduced pressure by extracting an organic layer. The concentrated compound was subjected to a silica column chromatograph to obtain Intermediate A-21-2 at a yield of 85%.

c) Synthesis of Intermediate A-21-3

In a 500 mL round-bottomed flask, 1 equivalent of the synthesized Intermediate A-21-2 was added into 150 mL of xylene, 0.05 equivalent of dichlorodiphenylphosphinoferrocene palladium, 1.2 equivalent of bispinacolato diboron, and 2 equivalent of potassium acetate were added, and the resultant was heated and refluxed under a nitrogen atmosphere for 18 hours. The reaction solution was cooled down, and the solution was washed by extraction, and an organic layer was treated by an activated carbon and then filtered by a silica gel, then the filtrate was concentrated. The concentrated solid was stirred with a small amount of hexane, and the solid was filtered to obtain Intermediate A-21-3 at a yield of 75%.

d) Synthesis of Compound A-21

Compound A-21 was synthesized in accordance with the same procedure as in the step b) of Synthesis Example 1, except that the synthesized Intermediate A-21-3 and Intermediate A-6-3 were used at each 1.0 equivalent, respectively.

LC/MS calculated for: C45H28N4O Exact Mass: 640.2263 found for: 641.53.

Synthesis Example 4: Synthesis of Compound A-4

[Reaction Scheme 4]

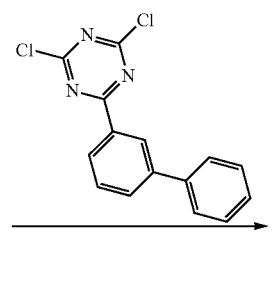

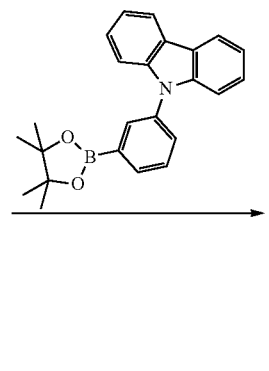

A-4-1

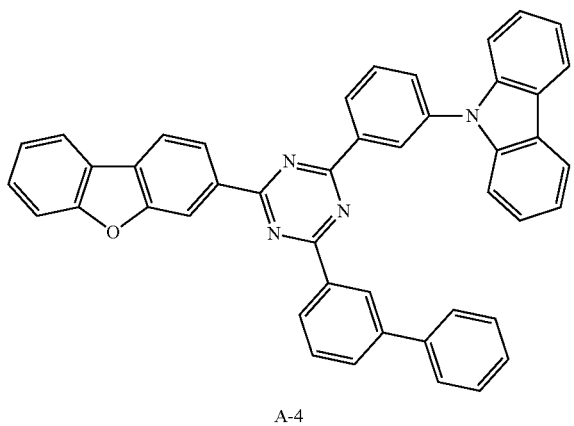

A-4 a) Synthesis of Intermediate A-4-1

Intermediate A-4-1 was synthesized in accordance with the same procedure as in the step a) of Synthesis Example 1, except that 1 equivalent of 2,4-dichloro-6-(3-phenylphenyl)-1,3,5-triazine and 0.9 equivalent of dibenzofuran-3-boronic acid were used.

b) Synthesis of Compound A-4

Compound A-4 was synthesized in accordance with the same procedure as in the step b) of Synthesis Example 1, except that the synthesized Intermediate A-4-1 and 9-[3-(4,4,5,5-tetramethyl-1,3,2-dioxaborolan-2-yl)phenyl]-carbazole (CAS: 870119-58-7) were used at each 1.0 equivalent, respectively.

LC/MS calculated for: C45H28N4O Exact Mass: 640.2263 found for: 640.23.

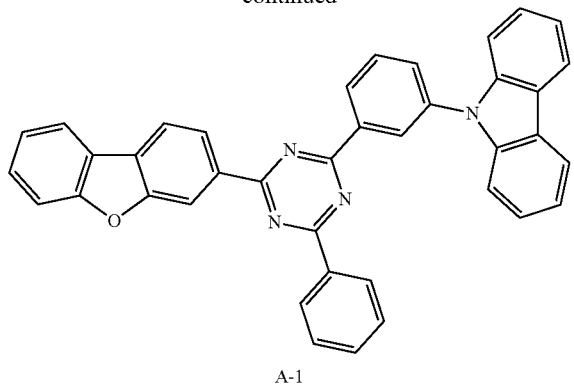

A-1

Compound A-1 was synthesized in accordance with the same procedure as in the step b) of Synthesis Example 1, except that the synthesized Intermediate A-6-3 and 9-[3-(4,4,5,5-tetramethyl-1,3,2-dioxaborolan-2-yl)phenyl]-carbazole (CAS: 870119-58-7) were used at each 1.0 equivalent, respectively.

LC/MS calculated for: C39H24N4O Exact Mass: 564.1950 found for: 565.20.

Synthesis Example 5: Synthesis of Compound A-1

[Reaction Scheme 5]

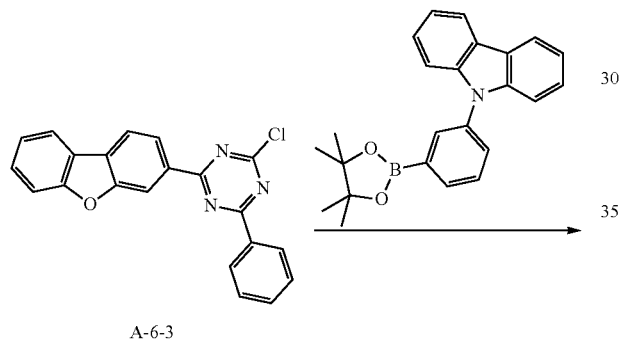

A-6-3

Comparative Synthesis Example 1: Synthesis of Comparative Compound R1

[Reaction Scheme 6]

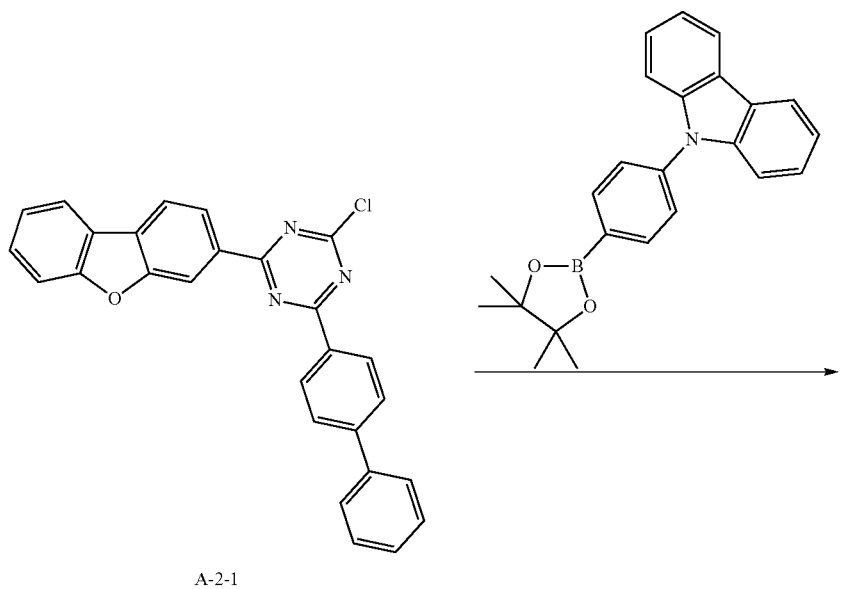

A-2-1

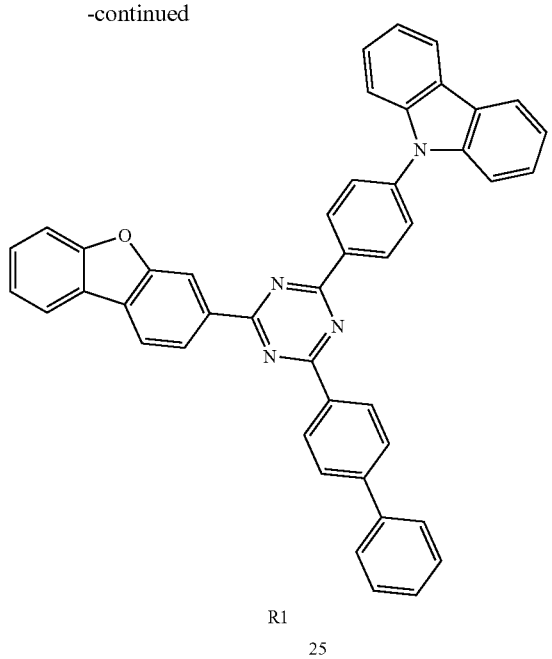

R1

Comparative Compound R1 was synthesized in accordance with the same procedure as in the step b) of Synthesis Example 1, except that Intermediate A-2-1 synthesized in the step a) of Synthesis Example 1 and 9-(4-(4,4,5,5-tetramethyl-1,3,2-dioxaborolan-2-yl)-phenyl)-carbazole (CAS: 785051-54-9) were used at each 1.0 equivalent, respectively.

LC/MS calculated for: C45H28N4O Exact Mass: 640.2263 found for: 641.23.

Comparative Synthesis Example 2: Synthesis of Comparative Compound R2

[Reaction Scheme 7]

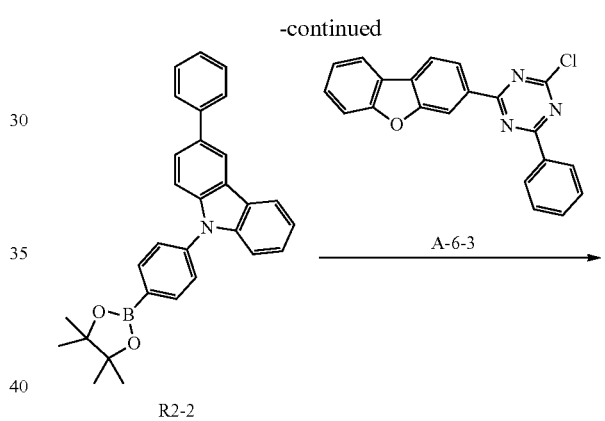

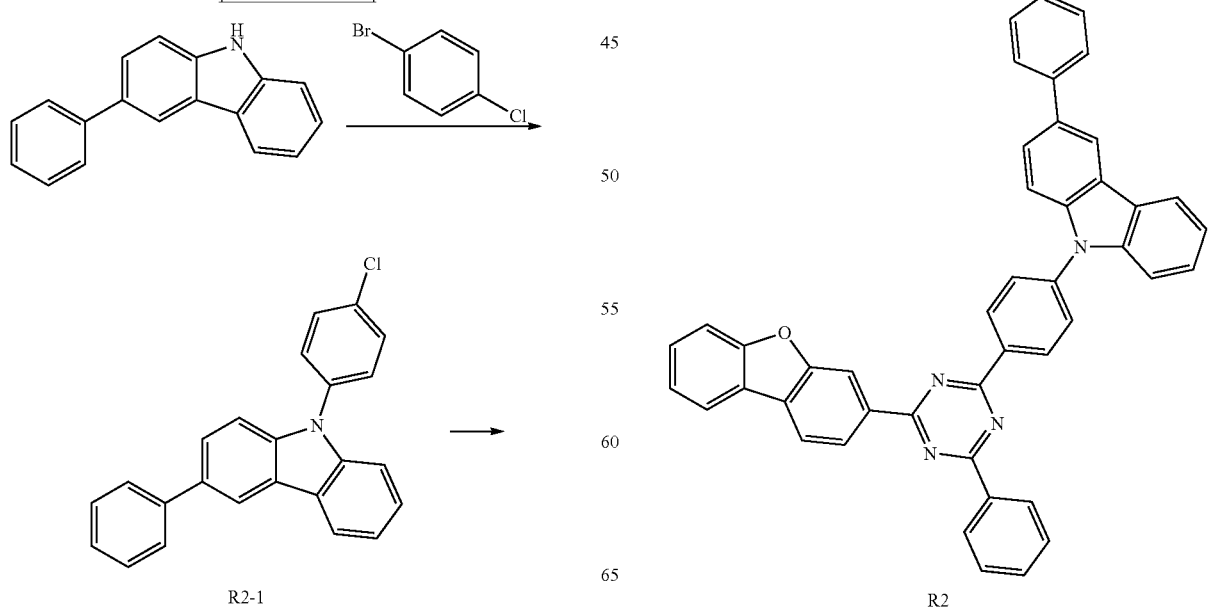

Comparative Compound R² was synthesized in accordance with the same procedure as in Synthesis Example 2, except that 4-chloro-1-bromobenzene was used instead of 3-chloro-1-bromobenzene.

LC/MS calculated for: C45H28N4O Exact Mass: 640.2263 found for: 641.23.

Comparative Synthesis Example 3: Synthesis of Comparative Compound R³

[Reaction Scheme 8]

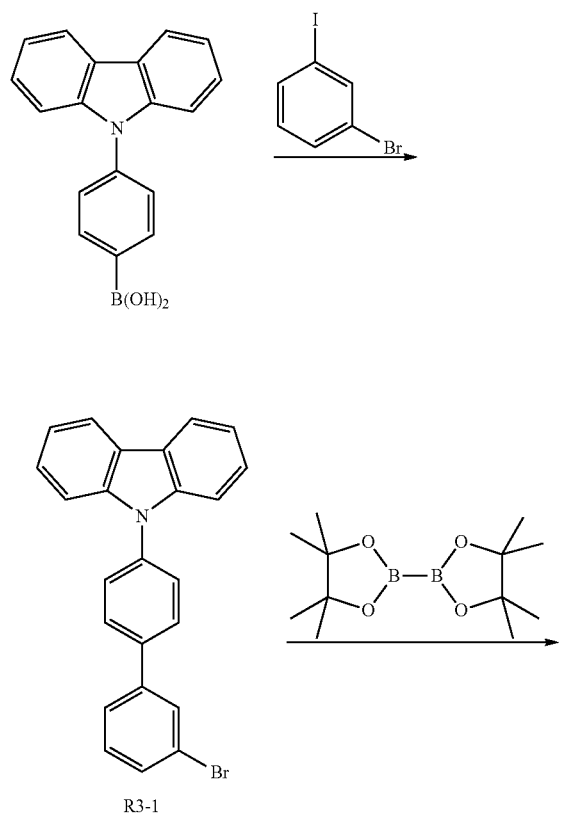

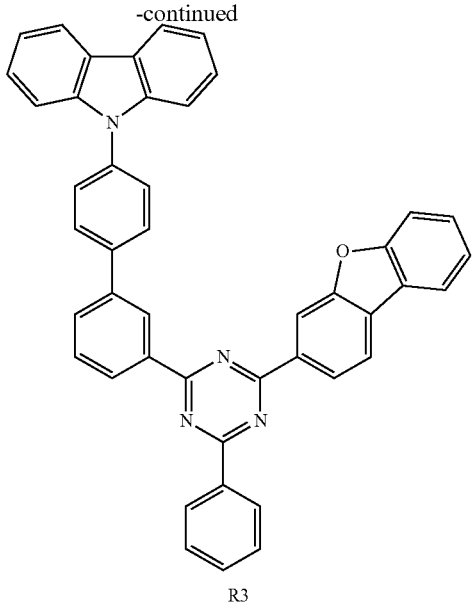

R3 a) Synthesis of Intermediate R3-1

Intermediate R3-1 was synthesized in accordance with the same procedure as in the step a) of Synthesis Example 1, except that 1 equivalent of [4-(9H-carbazole-9-yl)phenyl] boronic acid and 1.2 equivalent of 1-bromo-3-iodobenzene were used.

b) Synthesis of Intermediate R3-2

Intermediate R3-2 was synthesized in accordance with the same procedure as in the step c) of Synthesis Example 3, except that the synthesized Intermediate R3-1 was used.

c) Synthesis of Comparative Compound R3

Comparative Compound R3 was synthesized in accordance with the same procedure as in the step b) of Synthesis Example 1, except that the synthesized Intermediate R3-2 and Intermediate A-6-3 were used.

LC/MS calculated for: C45H28N4O Exact Mass: 640.2263 found for: 641.23.

Comparative Synthesis Example 4: Synthesis of Comparative Compound R4

[Reaction Scheme 9]

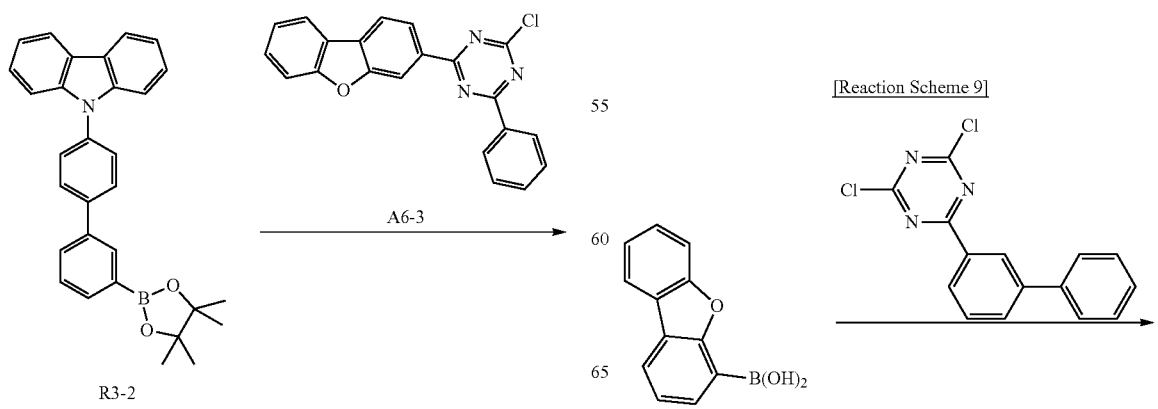

-continued

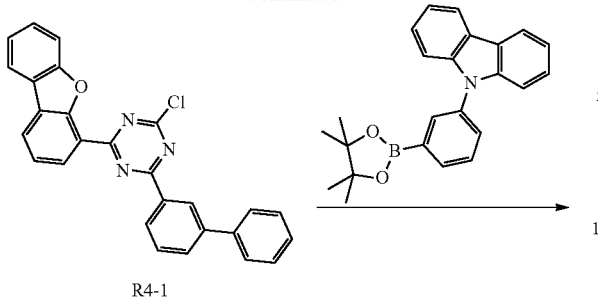

R4-1

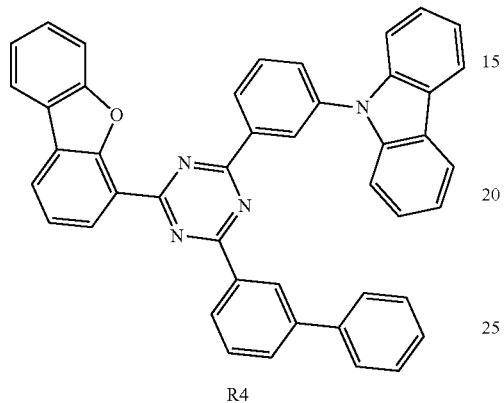

R4 a) Synthesis of Intermediate R4-1

An intermediate R4-1 was synthesized in accordance with the same procedure as in a) of Synthesis Example 1, except that 1 equivalent of 2,4-dichloro-6-(3-phenylphenyl)-1,3,5-triazine and 0.9 equivalent of dibenzofuran-4-boronic acid were used.

b) Synthesis of Comparative Compound R4

Intermediate R4 was synthesized in accordance with the same procedure as in the step b) of Synthesis Example 1, except using the synthesized Intermediate R4-1 and 9-(3-(4,4,5,5-tetramethyl-1,3,2-dioxaborolan-2-yl)-phenyl)-carbazole (CAS: 870119-58-7) were used at each 1.0 equivalent, respectively.

LC/MS calculated for: C45H28N4O Exact Mass: 640.2263 found for: 640.23.

Comparative Synthesis Example 5: Synthesis of Comparative Compound R5

[Reaction Scheme 10]

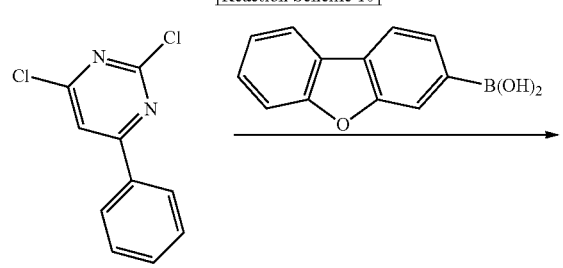

-continued

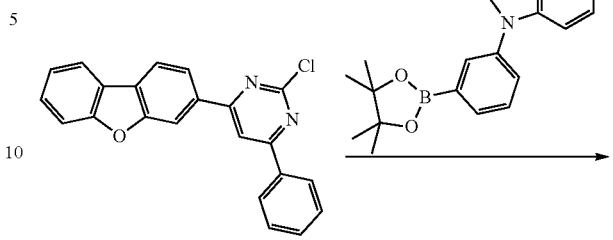

R5-1

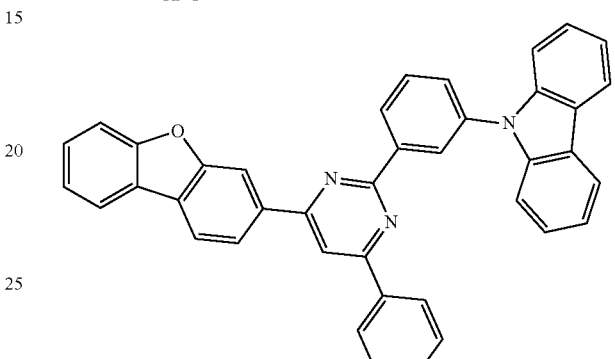

R5 a) Synthesis of Intermediate R5-1

Intermediate R5-1 was synthesized in accordance with the same procedure as in the step a) of Synthesis Example 1, except that 1 equivalent of 2,4-dichloro-6-phenylpyrimidine and 0.9 equivalent of dibenzofuran-3-boronic acid were used at each 1 equivalent, respectively.

b) Synthesis of Comparative Compound R5

Comparative Compound R5 was synthesized in accordance with the same procedure as in the step b) of Synthesis Example 1, except that the synthesized Intermediate R5-1 and 9-(3-(4,4,5,5-tetramethyl-1,3,2-dioxaborolan-2-yl)-phenyl)-carbazole (CAS: 870119-58-7) were used at each 1.0 equivalent, respectively.

LC/MS calculated for: C40H25N3O Exact Mass: 563.1998 found for: 564.23.

Comparative Synthesis Example 6: Synthesis of Comparative Compound R6

[Reaction Scheme 11]

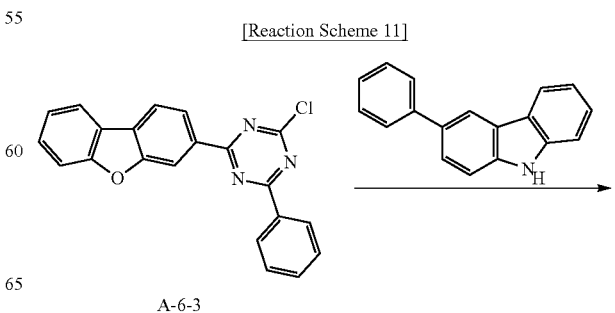

A-6-3

-continued

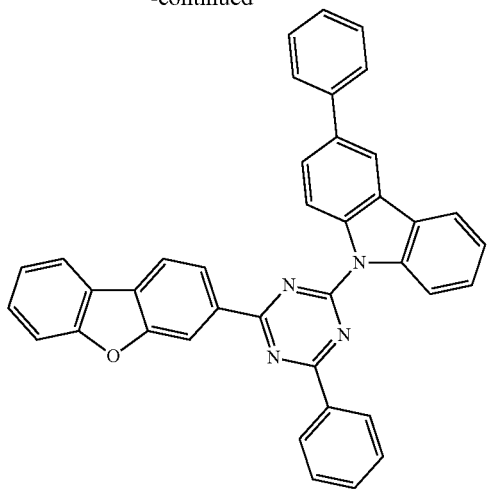

R6

Comparative Compound R6 was synthesized in accordance with the same procedure as in the step b) of Synthesis Example 1, except that the synthesized Intermediate A-6-3 and 3-phenyl-9H-carbazole were used at each 1.0 equivalent, respectively.

LC/MS calculated for: C39H24N4O Exact Mass: 564.1950 found for: 565.20.

Comparative Synthesis Example 7: Synthesis of Comparative Compound R7

[Reaction Scheme 12]

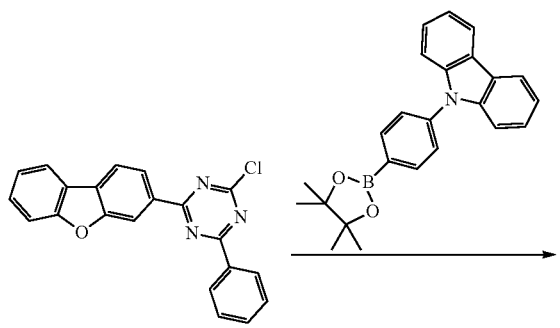

A-6-3

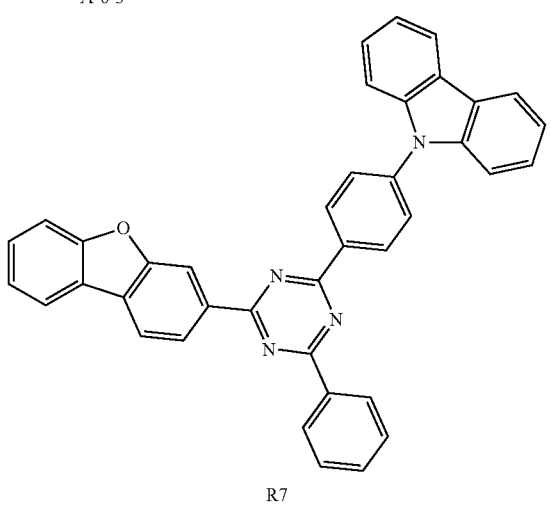

R7

Comparative Compound R7 was synthesized in accordance with the same procedure as in Comparative Synthesis Example 1, except that Intermediate A-6-3 was used instead of Intermediate A-2-1.

LC/MS calculated for: C39H24N4O Exact Mass: 564.1950 found for: 565.20.

Preparation of Second Compound for Organic Optoelectronic Device

Synthesis Example 6: Synthesis of Compound B-99

Compound B-99 was synthesized in accordance with the same procedure as in the known process disclosed in U.S. 2017/0317293 A1, which is incorporated herein by reference for all purposes.

Synthesis Example 7: Synthesis of Compound C-4

[Reaction Scheme 13]

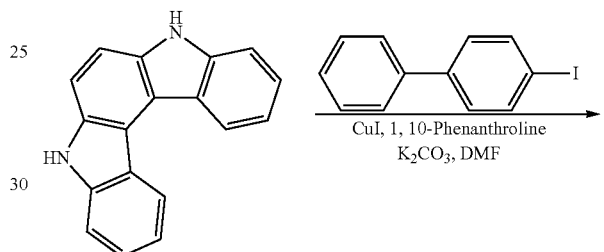

I-1

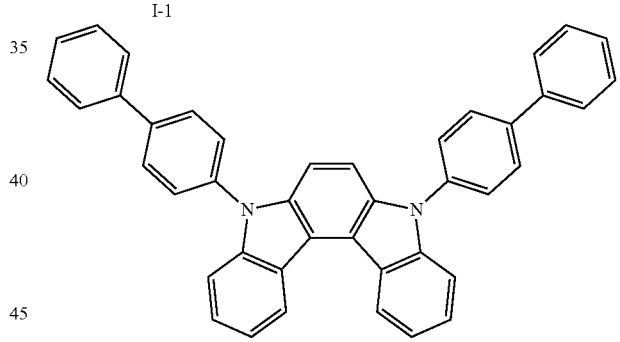

8 g (31.2 mmol) of Intermediate I-1, 20.5 g (73.32 mmol) of 4-iodobiphenyl, 1.19 g (6.24 mmol) of CuI, 1.12 g (6.24 mmol) of 1,10-phenanthroline, and 12.9 g (93.6 mmol) of $K_2CO_3$ were added into a round-bottomed flask, 50 ml of DMF was added, and the resultant was reflux-stirred under a nitrogen atmosphere for 24 hours. After completing the reaction, distilled water was added thereto to precipitate a crystal and filtered. The solid was dissolved in 250 ml of xylene and filtered by silica gel to precipitate a white solid, so 16.2 g (yield 93%) of Compound C-4 was synthesized.

LC/MS calculated for: C42H28N2 Exact Mass: 560.2252 found for: 561.23.

(Manufacture of Organic Light Emitting Diode)

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. On the hole transport layer, a 400 Å-thick light emitting layer was formed by vacuum-depositing Compound A-4 of Synthesis Example 4 as a host and 7 wt % of PhGD as a dopant. Subsequently, on the light emitting layer, a 300 Å-thick electron transport layer was formed by simultaneously vacuum-depositing the compound D and Liq in a ratio of 1:1, and on the electron transport layer, Liq and Al were sequentially vacuum-deposited to be 15 Å thick and 1200 Å thick, manufacturing an organic light emitting diode.

The organic light emitting diode had a five-layered organic thin layer of the following structure.

ITO/Compound A (700 Å)/Compound B (50 Å)/Compound C (1020 Å)/EML[Compound A-4:PhGD (7 wt %)] (400 Å)/Compound D:Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(-4-(4,6-di(naphthalen-2-yl)-1,3,5-triazin-2-yl)phenyl)quinoline

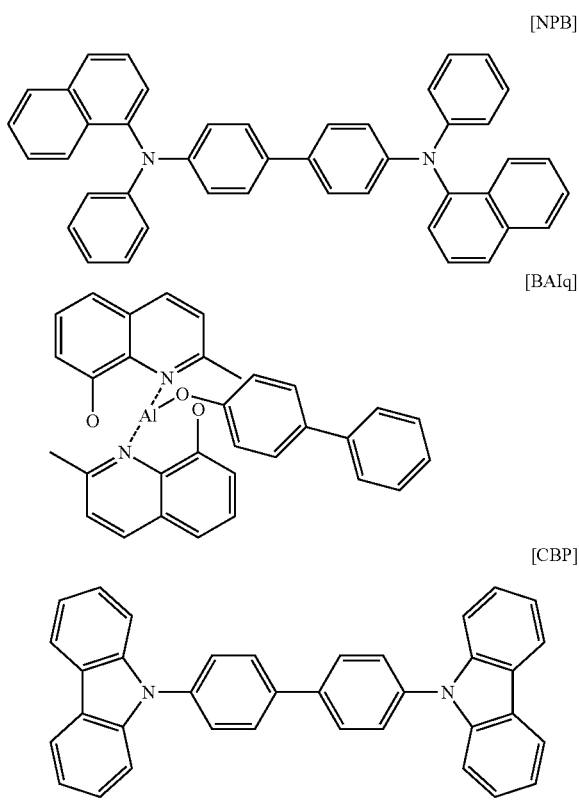

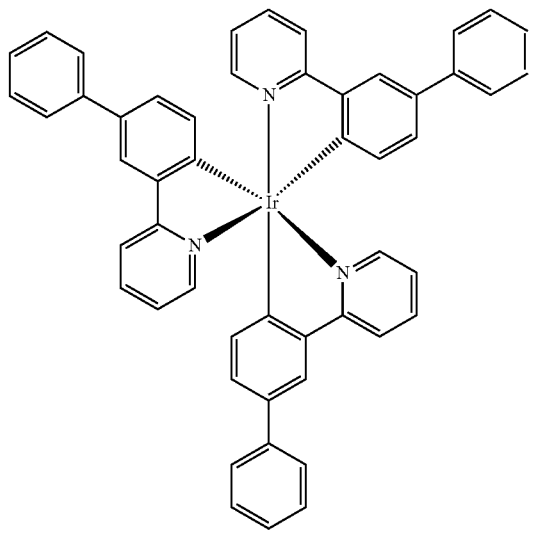

PhGD

Example 2 to Example 10 and Comparative Example 1 to Comparative Example 10

Each organic light emitting diode of Example 2 to Example 10 and Comparative Example 1 to Comparative Example 10 was manufactured according to the same method as Example 1 except for changing hosts and ratios thereof as shown in Tables 1 to 10.

Evaluation 1: Luminous Efficiency and Life-Span Increase Effect

Driving voltages and life-span characteristics of organic light emitting diodes according to Example 1 to Example 10 and Comparative Example 1 to Comparative Example 10 were evaluated. Specific measurement methods are as follows, and the results are shown in Tables 1 to 10.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to obtain the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T95 or T90 life-spans of the organic light emitting diodes according to Examples 1 to 10 and Comparative Examples 1 to 10 were measured as a time when their luminance decreased down to 90% or 95% relative to the initial luminance (cd/m$^2$) after emitting light at 24000 cd/m$^2$ as the initial luminance (cd/m$^2$) and measuring their luminance decrease depending on a time with a Polanonix life-span measurement system.

(5) Measurement of Driving Voltage

A driving voltage of each diode was measured using a current-voltage meter (Keithley 2400) at 15 mA/cm².

(6) Calculation of T90 or T95 Life-Span Ratio (%)

A relative ratio of T90(h) (or T95(h)) of a single host (ratio of Example to Comparative Example) or a mixed host applied with the same second host (ratio of Example (including a first compound as a first host) to Comparative Example (including a comparative compound as a first host)) was shown.

T90(T95) life-span ratio (%)={[T90(h)(or T95(h)) of Example (a single or a mixed host of a first compound)]/[T90(h)(or T95(h)) of Comparative Example (a single or a mixed host of a comparative compound)]}×100

(7) Calculation of Driving Voltage Ratio (%)

A relative ratio of driving voltage of a single host (ratio of Example to Comparative Example) or a mixed host applied with the same second host (ratio of Example (including a first compound as a first host) to Comparative Example (including a comparative compound as a first host)) was shown.

Driving Voltage Ratio (%)={[driving voltage (V) of Example (single or mixed host of a first compound)]/[driving voltage (V) of Comparative Example (single or mixed host of a comparative compound)]}×100

(8) Calculation of Power Efficiency Rate (%)

A relative ratio of power efficiency of a single host (ratio of Example to Comparative Example) or a mixed host applied with the same second host (ratio of Example (applied with a first compound as a first host) to Comparative Example (applied with a comparative compound as a first host)) was shown.

Ratio of Power Efficiency (%)={[Power efficiency (Cd/A) of Example (single or mixed host of a first compound)]/[Power efficiency (Cd/A) of Comparative Example (single or mixed host of a comparative compound]}×100

TABLE 1

| | Single host | Ratio of driving voltages (%) | Ratio of T90 life-span (%) |
|---|---|---|---|
| Example 1 | A-4 | 84% | 270% |
| Comparative Example 1 | R4 | 100% | 100% |

TABLE 2

| | Single host | Ratio of power efficiency (%) | Ratio of T90 life-span (%) |
|---|---|---|---|
| Example 2 | A-21 | 109% | 250% |
| Comparative Example 2 | R3 | 100% | 100% |

TABLE 3

| | Single host | Ratio of power efficiency (%) | Ratio of T90 life-span (%) |
|---|---|---|---|
| Example 3 | A-2 | 159% | 375% |
| Comparative Example 3 | R1 | 100% | 100% |

TABLE 4

| | Single host | Ratio of power efficiency (%) | Ratio of T90 life-span (%) |
|---|---|---|---|
| Example 4 | A-1 | 125% | 124% |
| Comparative Example 4 | R7 | 100% | 100% |

TABLE 5

| | Single host | Ratio of power efficiency (%) | Ratio of T90 life-span (%) |
|---|---|---|---|
| Example 5 | A-6 | 123% | 121% |
| Comparative Example 5 | R2 | 100% | 100% |

TABLE 6

| | Host | | | |
|---|---|---|---|---|
| | First Host | Second host | Ratio of first and second hosts | Ratio of T90 life-span (%) |
| Example 6 | A-2 | B-99 | 3:7 | 151% |
| Comparative Example 6 | R1 | B-99 | 3:7 | 100% |

TABLE 7

| | Host | | | |
|---|---|---|---|---|
| | First Host | Second host | Ratio of first and second hosts | Ratio of T90 life-span (%) |
| Example 7 | A-6 | B-99 | 4:6 | 152% |
| Comparative Example 7 | R2 | B-99 | 4:6 | 100% |

TABLE 8

| | Host | | | |
|---|---|---|---|---|
| | First Host | Second host | Ratio of first and second hosts | Ratio of T90 life-span (%) |
| Example 8 | A-21 | B-99 | 3:7 | 148% |
| Comparative Example 8 | R3 | B-99 | 3:7 | 100% |

TABLE 9

| | Host | | | |
|---|---|---|---|---|
| | First Host | Second host | Ratio of first and second hosts | Ratio of T90 life-span (%) |
| Example 9 | A-6 | C-4 | 5:5 | 176% |
| Comparative Example 9 | R6 | C-4 | 5:5 | 100% |

TABLE 10

| | Host | | | Ratio of T95 life-span (%) |
|---|---|---|---|---|
| | First Host | Second host | Ratio of first and second hosts | |
| Example 10 | A-1 | B-99 | 3:7 | 190% |
| Comparative Example 10 | R5 | B-99 | 3:7 | 100% |

TABLE 11

| | Single host | Ratio of driving voltages (%) | Ratio of T90 life-span (%) |
|---|---|---|---|
| Example 11 | A-1 | 96% | 162% |
| Comparative Example 11 | R5 | 100% | 100% |

Referring to Tables 1 to 11, it is confirmed that the compound for an organic optoelectronic device according to an embodiment has significantly more improved life-span than the conventional compounds disclosed in prior art references.

By way of summation and review, an organic light emitting diode (OLED) has recently drawn attention due to an increase in demand for flat panel displays. The organic light emitting diode converts electrical energy into light by applying current to an organic light emitting material. Performance of an organic light emitting diode may be affected by organic materials disposed between electrodes.

As described above, embodiments may provide a compound for an organic optoelectronic device capable of realizing an organic optoelectronic device having high efficiency and a long life-span. Embodiments may also provide an organic optoelectronic device having high efficiency and a long life-span.

DESCRIPTION OF SYMBOLS

100, 200: organic light emitting diode
105: organic layer
110: cathode
120: anode
130: light emitting layer
140: hole auxiliary layer Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise For example indicated. Accordingly, it will be understood by those of skill in the art that various changes in form and details may be made without departing from the spirit and scope of the present invention as set forth in the following claims.

What is claimed is:

1. An organic optoelectronic device, comprising
an anode and a cathode facing each other, and
at least one organic layer disposed between the anode and the cathode,
wherein the organic layer includes a light emitting layer, and
the light emitting layer includes a compound represented by Chemical Formula 1-1 as a host material for a phosphorescent dopant,

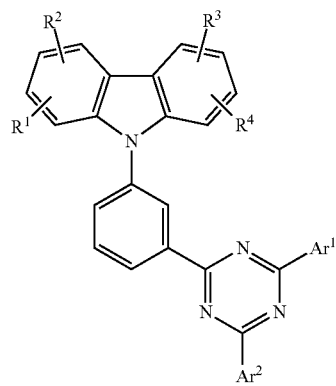

[Chemical Formula 1-1]

wherein, in Chemical Formula 1-1,
$R^1$, $R^2$, and $R^4$ are each independently hydrogen, deuterium, a substituted or unsubstituted C1 to C6 alkyl group, or a substituted or unsubstituted phenyl group, provided that when the phenyl group is substituted the substituent does not include a dibenzofuranyl group, a dibenzothiophenyl group, or a fluorenyl group,
$R^3$ is a substituted or unsubstituted phenyl group, provided that when the phenyl group is substituted the substituent does not include a carbazolyl group and does not include an indolyl group,
$Ar^1$ and $Ar^2$ are each independently a substituted or unsubstituted C6 to C30 aryl group or a group represented by Chemical Formula A, provided that at least one of $Ar^1$ and $Ar^2$ is a group represented by Chemical Formula A:

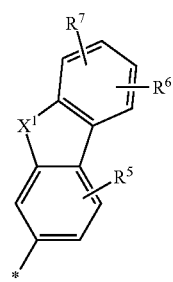

[Chemical Formula A]

wherein, in Chemical Formula A,
$X^1$ is O or S,
$R^5$ to $R^7$ are each independently hydrogen, deuterium, a substituted or unsubstituted C1 to C6 alkyl group, or a substituted or unsubstituted phenyl group, and
* is a linking point.

2. The organic optoelectronic device of claim 1, wherein one of $Ar^1$ and $Ar^2$ is the group represented by Chemical Formula A and the other of $Ar^1$ and $Ar^2$ is a substituted or unsubstituted C6 to C30 aryl group.

3. The organic optoelectronic device of claim 1, wherein $Ar^1$ and $Ar^2$ are each independently a substituted or unsubstituted phenyl group, a substituted or unsubstituted biphenyl group, a substituted or unsubstituted naphthyl group, or the group represented by Chemical Formula A.

4. The organic optoelectronic device of claim 1, wherein $Ar^1$ and $Ar^2$ are each independently one of groups of Group I:

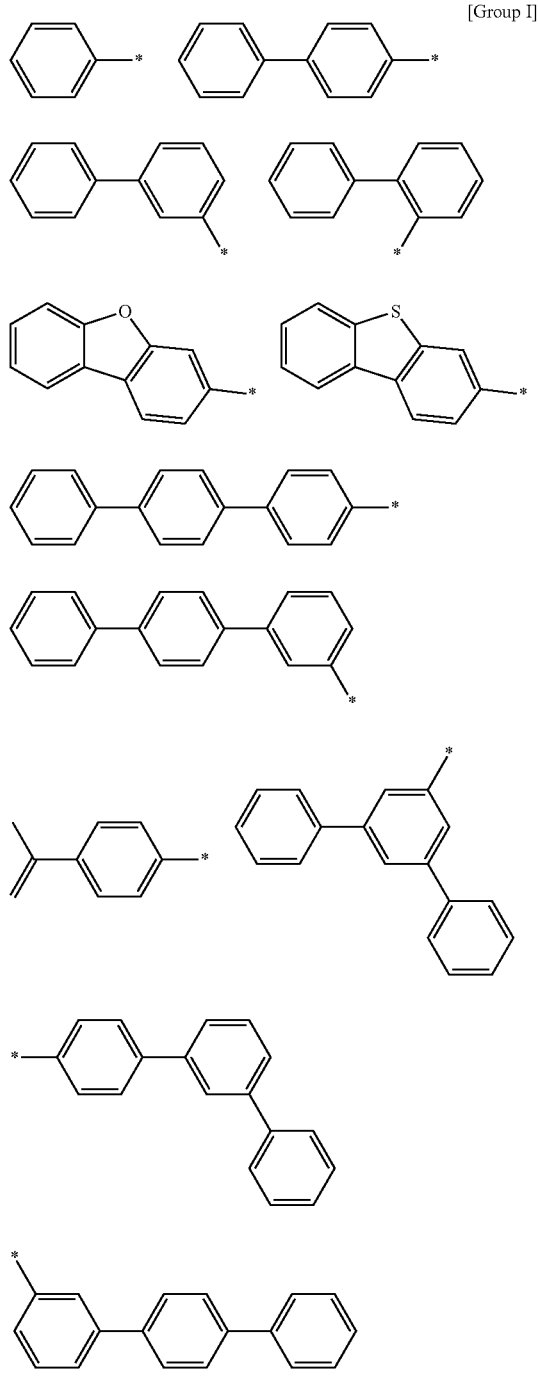

[Group I]

wherein, in Group I, * is a linking point.

5. The organic optoelectronic device of claim 1, the compound represented by Chemical Formula 1-1 being one of the compounds of Group 1:

[Group 1]

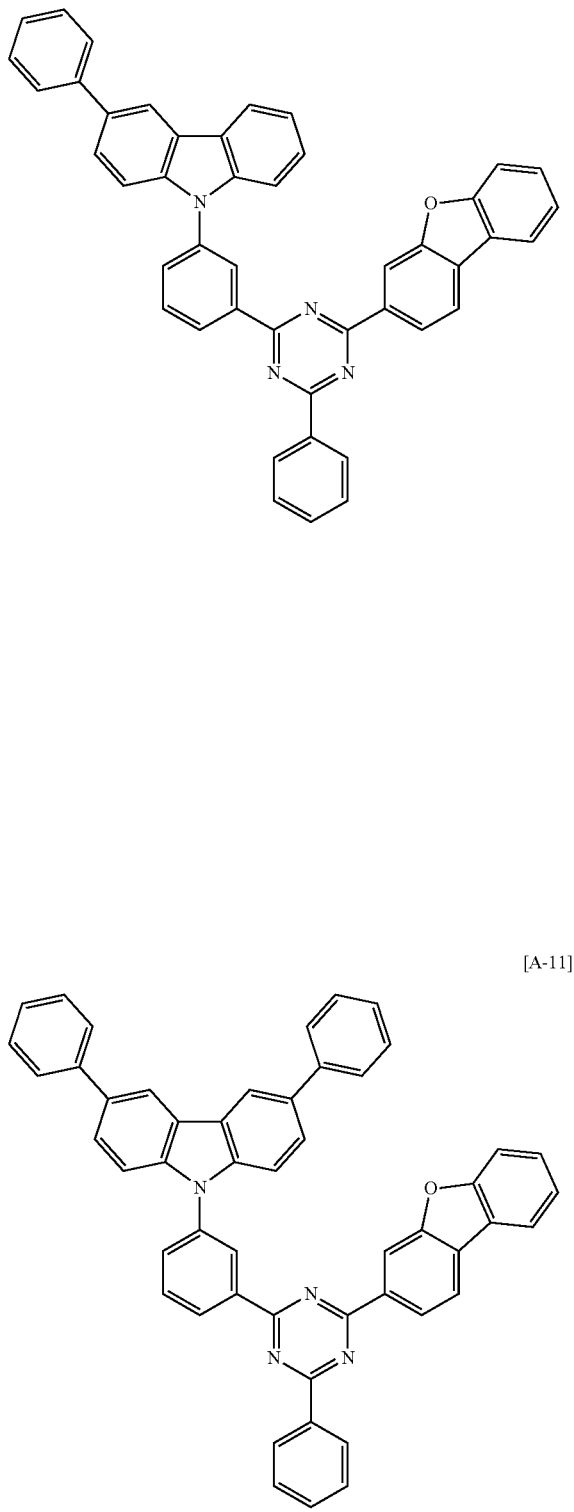

[A-6]

[A-11]

[A-12]
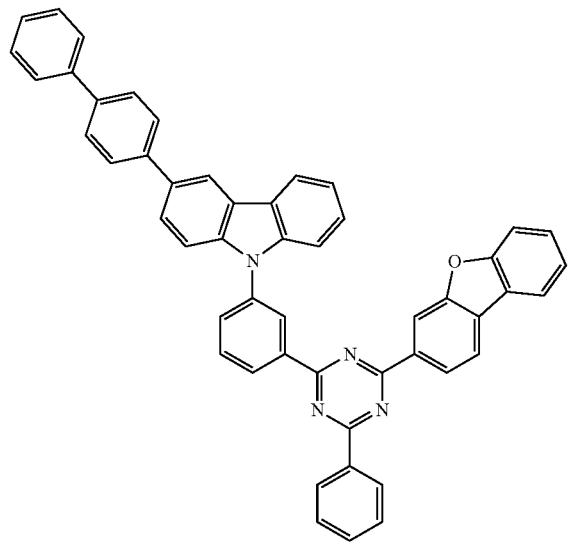
[A-14]
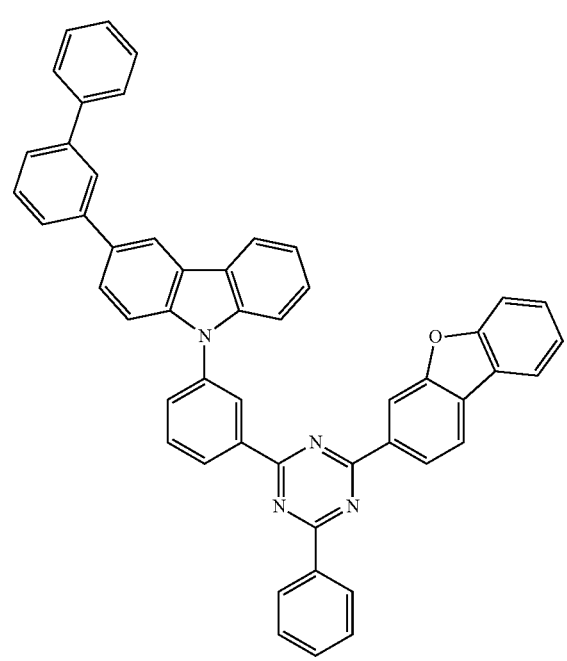
[A-48]
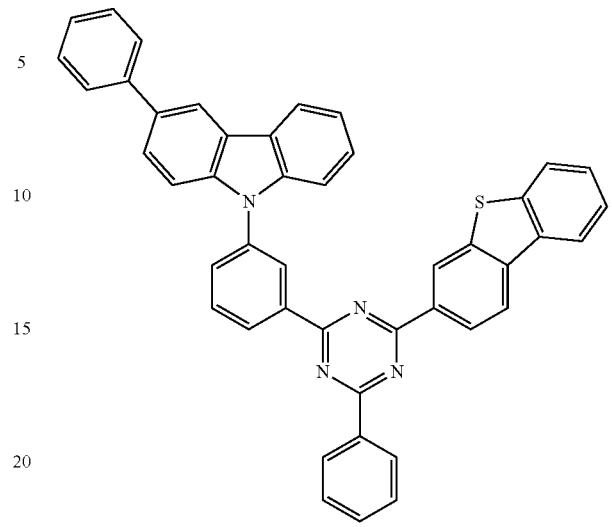
[A-51]
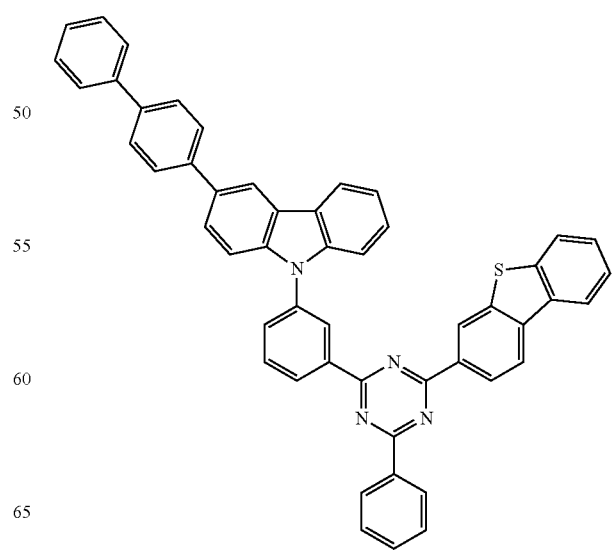
[A-52]

[A-54]

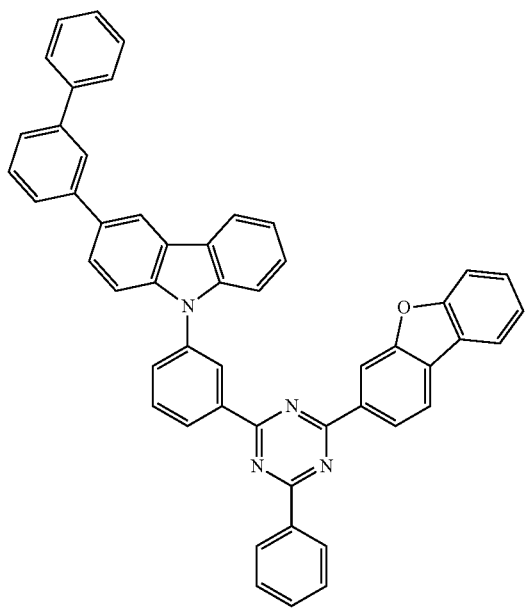

[Group II]

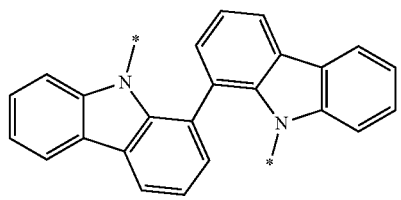
C-1

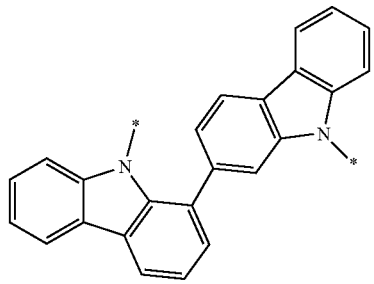
C-2

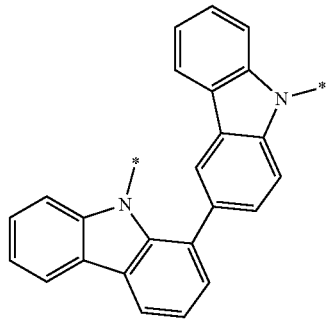
C-3

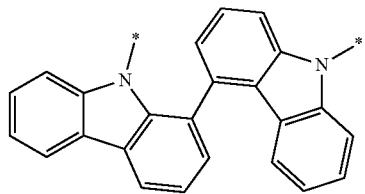
C-4

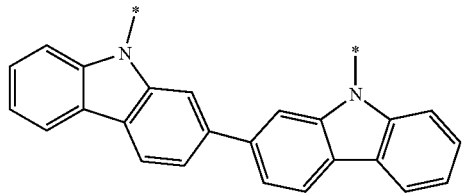
C-5

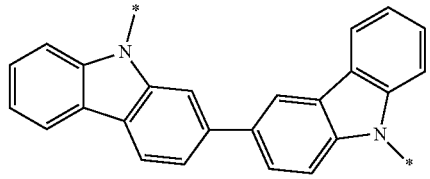
C-6

6. The organic optoelectronic device of claim 1, wherein the compound represented by Chemical Formula 1-1 is present as a first compound in a composition that further includes second compound represented by Chemical Formula 2:

[Chemical Formula 2]

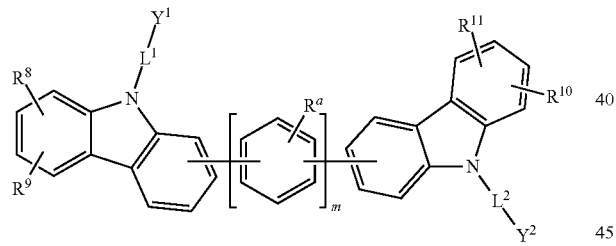

wherein, in Chemical Formula 2, $Y^1$ and $Y^2$ are each independently a substituted or unsubstituted C6 to C20 aryl group, or a substituted or unsubstituted C2 to C30 heterocyclic group, $L^1$ and $L^2$ are each independently a single bond, or a substituted or unsubstituted C6 to C20 arylene group, $R^a$ and $R^8$ to $R^{11}$ are each independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group, and m is 0, 1, or 2.

7. The organic optoelectronic device of claim 6, wherein:

Chemical Formula 2 includes one of structures of Group II, and $Y^1$, $Y^2$, $L^1$, and $L^2$ forming moieties *-$L^1$-$Y^1$ and *-$L^2$-$Y^2$ of Chemical Formula 2 are selected to form one of substituents of Group III:

-continued
C-7
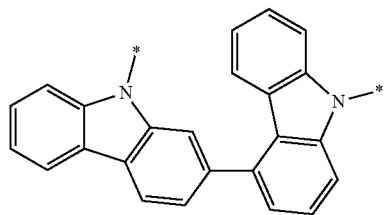
C-8
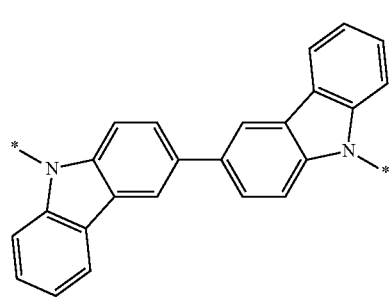
C-9
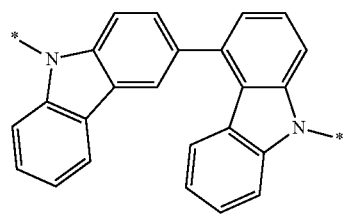
C-10
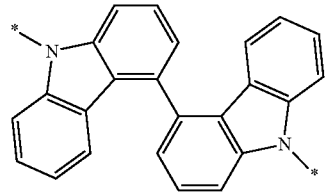
C-11
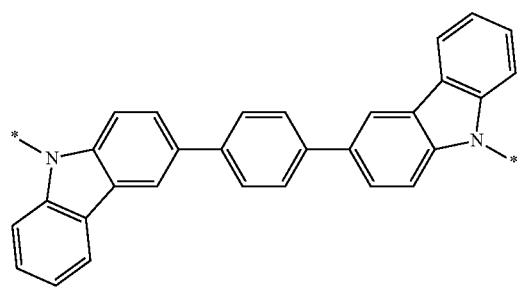
C-12
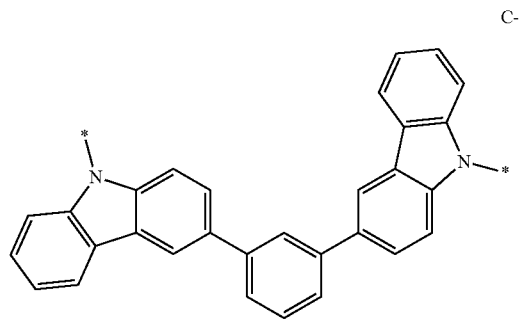
-continued
C-13
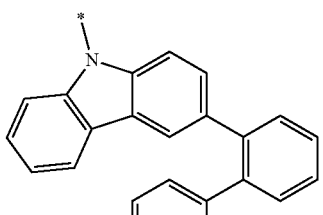
C-14
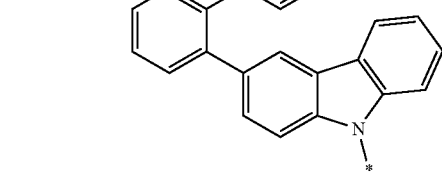
C-15
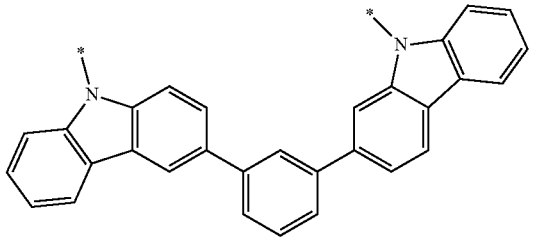
C-16
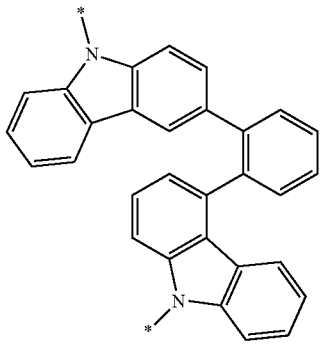
C-17
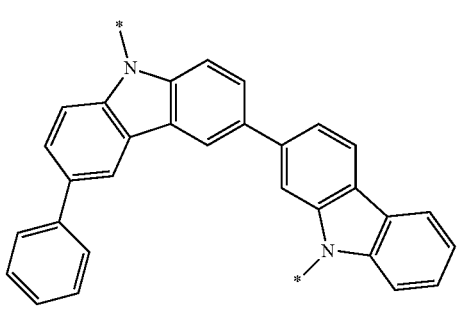
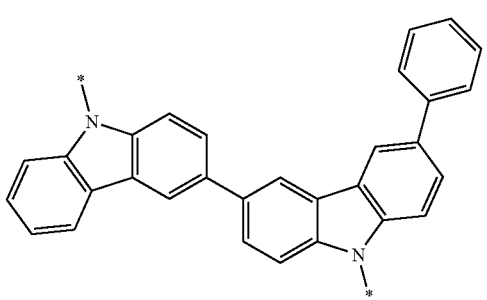

C-18
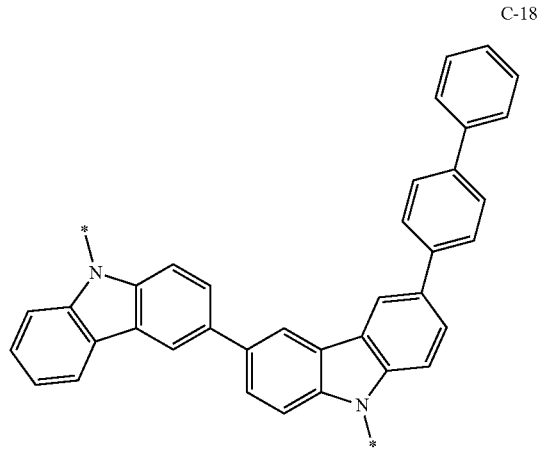
[Group III]
B-1
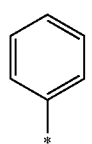
B-2
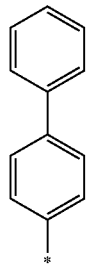
B-3
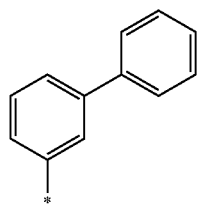
B-4
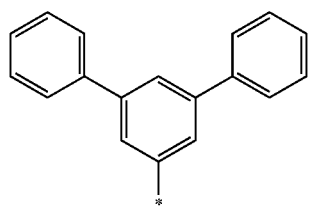
B-5
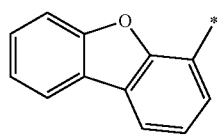
B-6
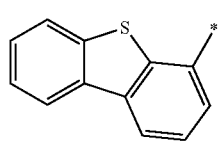
B-7
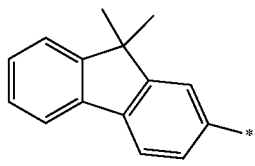
B-8
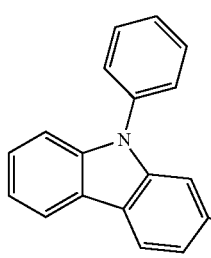
B-9
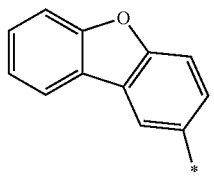
B-10
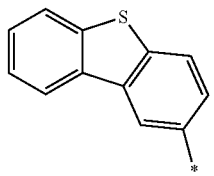
B-11
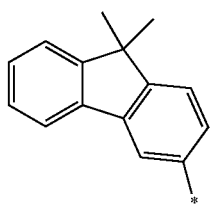
B-12
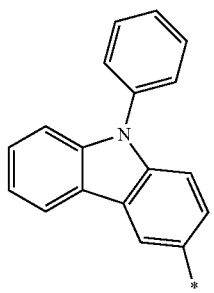
B-13
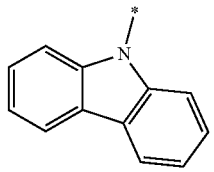
B-14
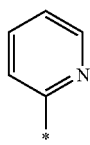

B-15 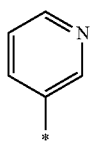
B-16 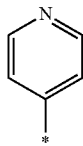
B-17 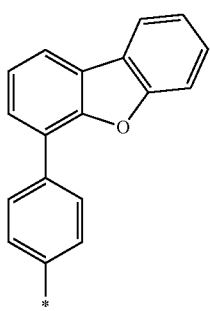
B-18 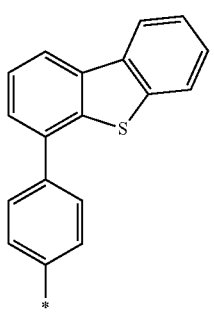
B-19 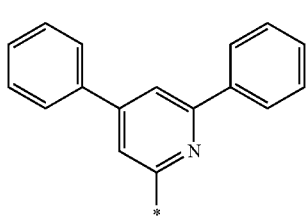
B-20 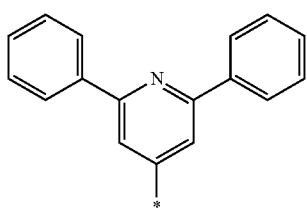
B-21 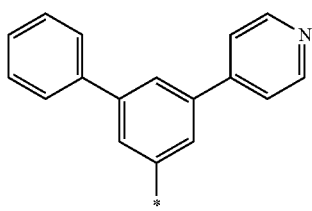
B-22 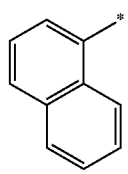
B-23 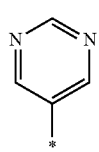
B-24 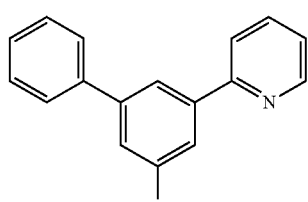
B-25 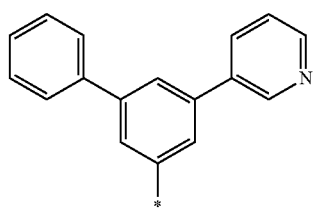
B-26 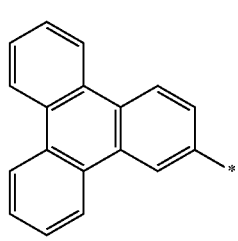
B-27 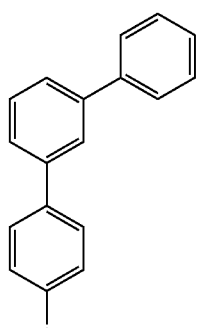
B-28 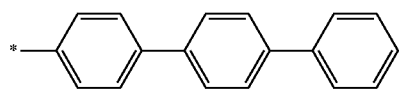

B-29

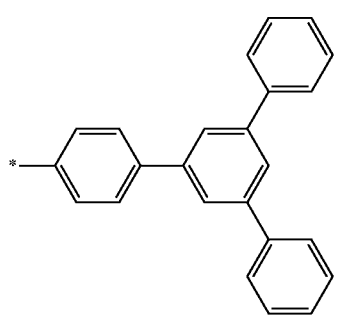

wherein, in Group II and Group III, * is a linking point.

8. The organic optoelectronic device of claim 7, wherein Chemical Formula 2 includes a structure represented by Chemical Formula C-8 or Chemical Formula C-17 of Group II.

9. The organic optoelectronic device of claim 8, wherein the moieties *-L$^1$-Y$^1$ and *-L$^2$-Y$^2$ of Chemical Formula 2 are each independently selected from substituents B-1, B-2, and B-3 of Group III.

10. The organic optoelectronic device of claim 6, wherein:
Chemical Formula 2 is represented by Chemical Formula 2A:

[Chemical Formula 2A]

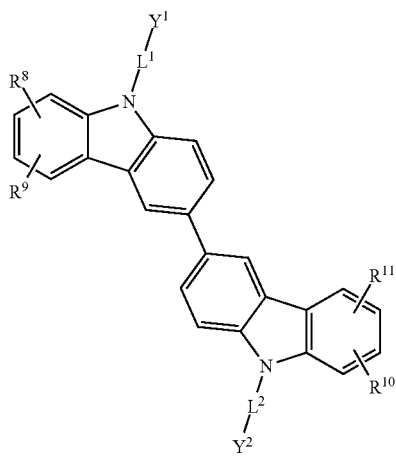

wherein, in Chemical Formula 2A,
Y$^1$ and Y$^2$ are each independently a substituted or unsubstituted C6 to C20 aryl group, or a substituted or unsubstituted C2 to C30 heterocyclic group,
L$^1$ and L$^2$ are each independently a single bond, or a substituted or unsubstituted C6 to C20 arylene group, and
R$^8$ to R$^{11}$ are each independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group.

11. A display device comprising the organic optoelectronic device of claim 1.

* * * * *